United States Patent
Thippeswamy et al.

(10) Patent No.: US 11,000,524 B2
(45) Date of Patent: May 11, 2021

(54) TYROSINE KINASE INHIBITION AS A TREATMENT FOR EPILEPSY

(71) Applicant: Iowa State University Research Foundation, Inc., Ames, IA (US)

(72) Inventors: Thimmasettappa Thippeswamy, Ames, IA (US); Anumantha G. Kanthasamy, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 100 days.

(21) Appl. No.: 15/829,608

(22) Filed: Dec. 1, 2017

(65) Prior Publication Data

US 2018/0153891 A1 Jun. 7, 2018

Related U.S. Application Data

(60) Provisional application No. 62/429,333, filed on Dec. 2, 2016.

(51) Int. Cl.
| | |
|---|---|
| *A61K 31/517* | (2006.01) |
| *A61K 31/18* | (2006.01) |
| *A61K 31/19* | (2006.01) |
| *A61K 31/325* | (2006.01) |
| *A61K 31/4015* | (2006.01) |

(Continued)

(52) U.S. Cl.
CPC .......... *A61K 31/517* (2013.01); *A61K 9/0053* (2013.01); *A61K 31/18* (2013.01); *A61K 31/19* (2013.01); *A61K 31/325* (2013.01); *A61K 31/4015* (2013.01); *A61K 31/4166* (2013.01); *A61K 31/515* (2013.01); *A61K 31/53* (2013.01); *A61K 31/5513* (2013.01); *A61K 31/7024* (2013.01); *A61K 45/06* (2013.01); *A61P 25/08* (2018.01)

(58) Field of Classification Search
CPC .... A61K 31/517; A61K 31/18; A61K 31/325; A61K 31/515; A61K 45/06; A61P 25/08
See application file for complete search history.

(56) References Cited

U.S. PATENT DOCUMENTS 6,110,499 A * 8/2000 Shivanand ......... A61K 31/4166
424/464

FOREIGN PATENT DOCUMENTS

WO  WO 2015/069217  *  5/2015

OTHER PUBLICATIONS

Dorwald (Side Reactions in Organic Synthesis: A Guide to Successful Synthesis Design, Weinheim: WILEY-VCH Verlag GmbH & Co. KGaA, 2005, Preface).*

(Continued)

*Primary Examiner* — Anna Pagonakis
(74) *Attorney, Agent, or Firm* — McKee, Voorhees & Sease, PLC

(57) ABSTRACT

The present invention describes novel pharmaceutical compositions and methods for treatment of diseases, disorders, or conditions characterized by recurrent seizures, particularly, epilepsy. According to the invention, compounds which inhibit the activity or expression of non-receptor Fyn tyrosine kinase can prevent activation epileptic pathophysiology and provide protection from and treatment of epilepsy. Particularly preferred is the class of small molecule Fyn kinase inhibitors such as sacaratinib and its prodrugs, derivatives, analogs and the like.

12 Claims, 47 Drawing Sheets
(10 of 47 Drawing Sheet(s) Filed in Color)

(51) Int. Cl.
*A61K 31/4166* (2006.01)
*A61K 31/515* (2006.01)
*A61K 31/5513* (2006.01)
*A61K 31/7024* (2006.01)
*A61K 9/00* (2006.01)
*A61K 45/06* (2006.01)
*A61P 25/08* (2006.01)
*A61K 31/53* (2006.01)

(56) References Cited

OTHER PUBLICATIONS

Nygaard et al. A phase llb multiple ascending dose study of the safety, tolerability, and central nervous system availability of AZD0503 (saracatinib) in Alzheimer's disease. Alzheimer's Research & Threapy, 2015, 7:35.*
McNamara et al. Molecular mechanisms underlying epileptogenesis. Sciene's STKE, Oct. 10, 2006, vol. 2006, Issue 356.*
Remington's Pharmaceutical Sciences (Sixteenth Edition; 1980, p. 420-425).*
Berge et al. ("Pharmaceutical Salts", Journal of Pharmaceutical Sciences, 66(1); 1977:1-19).*
Pitkanen et al. Epileptogenesis. Cold Spring Harb. Perspect. 2015; 5:a022822.*
Noe et al. Pharmacological blockade of IL-1beta/IL-1 receptor type 1 axis during epileptogenesis provides neuroprotection in two rate modesl of temporal lobe epilepsy. Neurobiology of Diseases, 59, 2013, 183-193.*
Cain, Donald P., et al., "Fyn Tyrosine Kinase is Required for Normal Amygdala Kindling", Epilepsy Research, pp. 107-114. Apr. 3, 1995.

* cited by examiner

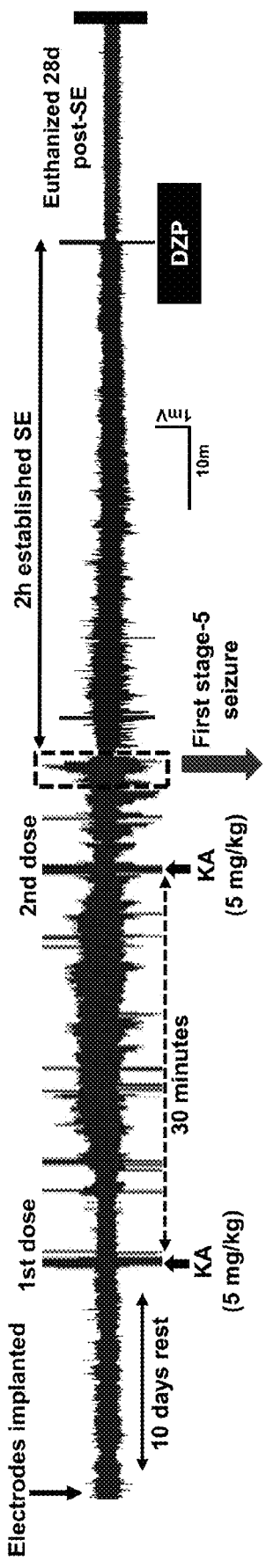
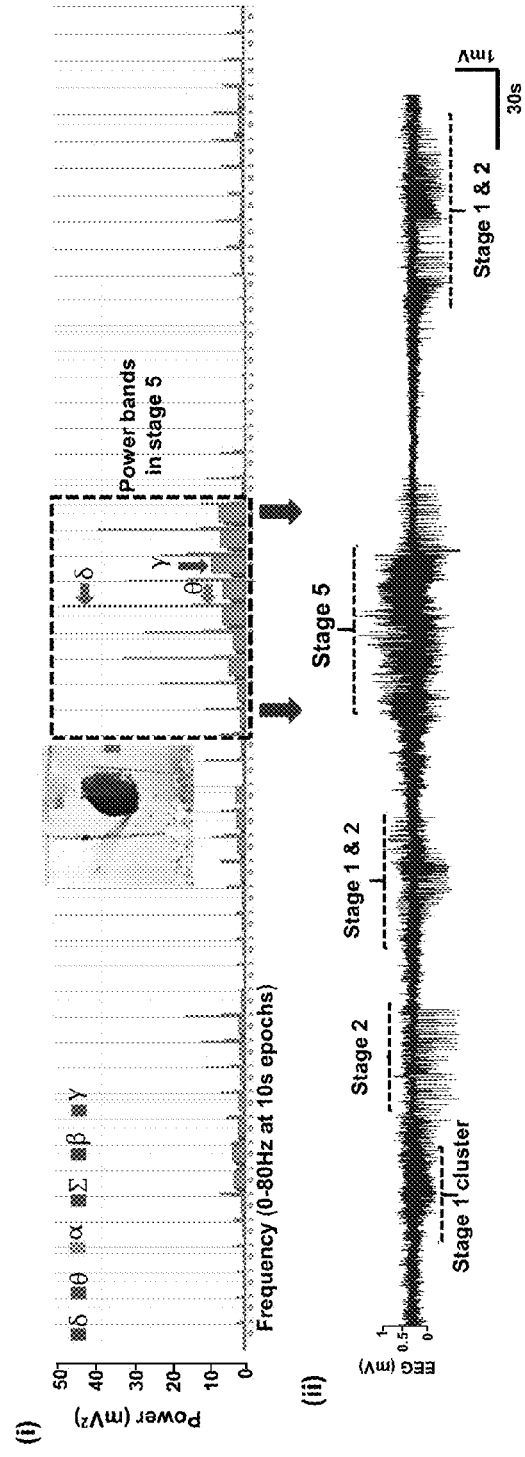
FIG. 3A
FIG. 3B

TYROSINE KINASE INHIBITION AS A TREATMENT FOR EPILEPSY

CROSS REFERENCE TO RELATED APPLICATION

This application claims priority under 35 U.S.C. § 119 of a provisional application Ser. No. 62/429,333, filed Dec. 2, 2016 which application is hereby incorporated by reference in its entirety.

GRANT REFERENCE

This invention was made with government support under Grant No. NS088206 awarded by NIH. The government has certain rights in the invention.

FIELD OF THE INVENTION

The present invention is directed to a pharmaceutical composition and methods for treating or preventing epilepsy in a subject in need thereof.

BACKGROUND OF THE INVENTION

Epilepsy is the most common neurological disorder, affecting about 1% of the population worldwide. Epilepsy describes a condition in which a person has recurrent seizures due to a chronic, underlying process. Epilepsy refers to a clinical phenomenon rather than a single disease entity, since there are many forms and causes of epilepsy. Using a definition of epilepsy as two or more unprovoked seizures, the incidence of epilepsy is estimated at 5 to 10 people per 1000. An essential step in the diagnosis and treatment of a patient with a seizure is to determine the type of seizure that has occurred. The main characteristic that distinguishes the different categories of seizure is whether the seizure activity is partial or generalized or unclassified.

For the general population there are approximately 20-70 new cases per 100,000 diagnosed each year with a 3-5% lifetime probability of developing the disease. The older established antiepileptic drugs (AEDs) phenytoin, carbamazepine, clonazepam, ethosuximide, valproic acid and barbiturates are widely prescribed but suffer from a range of side effects. Furthermore, there is a significant group of patients (20-30%) that are resistant to the currently available therapeutic agents. Since 1989 several new drugs have been launched, including felbamate, gabapentin, lamotrigine, oxcarbazepine, tiagabine, topiramate, vigabartrin, zonisamide and levetiracetam. While many of new AEDs show improved efficacies and side-effect profiles, about 30% of patients with epilepsy remain untreated. Additionally, new antiepileptic drugs based on their action on the ion-channels have started to be developed (Bialer and White, 2010; Rogawaski and Loscher, 2004; Schmidt, 2009). However, the majority of the current AEDs (including 47 failed drugs in human trials) are less effective, or do not cure the disease, and some even require lifelong administration with some potential side-effects (Kwan et al., 2011; Varvel et al., 2015). This suggests the need for development of more effective drugs that target alternative pathways to prevent/treat epilepsy. There is clearly a need for improved medication.

Neuroinflammation is emerging as a new mechanistic target for drug development, and it also serves as a biomarker for neuroimaging in various neurodegenerative diseases (Abi-Dargham and Horga, 2016; Albrecht et al., 2016; French 2016; Gershen et al., 2015). The microglia are considered as resident macrophages and they mediate neuroinflammation and hyperexcitability in neurons (Block, 2014; Davis and Carson, 2012; Devinsky et al., 2013). The reactive glia are known to produce proinflammatory cytokines, reactive oxygen and nitrogen species (ROS/RNS), lipid peroxidation, hippocampal neurodegeneration, reorganization of neural circuits, and hyper-synchronicity (Bertram 2013; Goldberg and Coulter, 2013; Ryan et al., 2014; Scharfman and Binder, 2013; Vezzani et al., 2011 and 2013). The microglia become reactive in response to SE insult (Avignone et al., 2008; Puttachary et al., 2016a and b). Increased levels of proinflammatory cytokines and nitrooxidative stress molecules are known to cause neurodegeneration (Glass et al., 2010; Vezzani et al., 2011 and 2013), altered synaptic plasticity, and decreased seizure threshold in epilepsy models (Bozzi et al., 2011; Reddy and Kuruba, 2013). However, the mechanism of microglial activation following seizures is largely unknown. Therefore, understanding the mechanism of activation of microglia will reveal its impact on epileptogenesis.

There are nine members of Src family of intracellular non-receptor tyrosine kinases (SFK). Five of them (Src, Fyn, Lck, Lyn, and Yes) are expressed in the central nervous system, but Src and Fyn are most highly expressed in the brain. Fyn activity, like that of other Src family kinases, is regulated by intramolecular interactions that depend on an equilibrium between tyrosine phosphorylation and dephosphorylation (Thomas et al., 1997, Ann. Rev. Cell & Dev. Biol. 13:513-609). In the basal state, catalytic activity is constrained by intramolecular interactions, such as engagement of the SH2 domain by a phosphorylated C-terminal Tyr 527. Disruption of these interactions by phosphorylation at Tyr 416 in the activation loop of the kinase domain and/or by dephosphorylation of Tyr 527 results in Fyn activation (Hunter, 1987, Cell, 49: 1-4).

The Fyn is associated with both excitatory and inhibitory ion channels, and its role in pathophysiology of synaptic transmission, plasticity, neurodevelopment, and brain injury are well known (Knox and Jiang, 2015; Kojima et al., 1998; Lu et al., 1999; Nygaard et al., 2014; Salter and Kalia, 2004). The neuronal Fyn has been known to modulate both NMDA and GABAA receptors (Kojima et al., 1998; Lu et al., 1999), and the role of Fyn in normal amygdala kindling (Cain et al., 1995) suggests its potential association with acute seizure onset. However, its role in chronic seizures are not well known. Likewise, the roles of Fyn kinase and one of its downstream targets, the protein kinase C delta (PKCδ), in microglia that mediate neuroinflammation and epileptogenesis are also not well known. Their role in microglia in experimental disease models is however beginning to emerge as has been described in Parkinson's disease (PD) models (Nygaard et al., 2015; Panicker et al., 2015). Therefore, the Fyn-PKCδ signaling pathway may also mediate microglial activation in seizures, and disabling the Fyn kinase will suppress epileptiform activity and seizures by dampening neuroinflammation and neurodegeneration.

In a cell culture and animal model of Parkinson's disease (PD), it has been shown that phosphorylated Fyn activates PKCd in microglia, which in turn translocates to the nucleus (Saminathan et al., 2011) and initiates transcription of proinflammatory cytokines either directly or in association with c-Abl or NF-κB signaling components (Buj or et al., 2011; Gordon et al., 2016). It was shown that shRNA-mediated knockdown or genetic ablation of PKCd in primary microglia abolished inflammogens-induced proinflammatory response in microglia, and also suppressed ROS and RNS production, and proinflammatory cytokines release (Gordon et al., 2016). Phosphorylated PKCd also activates cytoplasmic subunit of the NOX2, which forms a functional complex with the membrane associated gp91$^{phox}$ to activate NOX2 signaling pathway and drives ROS and RNS production (Bedard and Krause, 2007; Fontayne et al., 2002; Gordon et al., 2016).

Inhibitors of SFK, such as dasatinib, bosutinib, saracatinib or ponatinib, are used in the treatment of cancer, in particular lung cancer. Approximately 85% of all lung cancer incidences are non-small cell lung cancer (NSCLC) (Jemal, Siegel et al., 2008). Non-small cell lung cancer (NSCLC) is one of the two main types of lung carcinoma, non-small cell (80.4%) and small-cell (16.8%) lung carcinoma, the classification being based on histological criteria. The non-small cell lung carcinomas have a similar prognosis and similar management and comprise three sub-types: squamous cell lung carcinoma, adenocarcinoma and large cell lung carcinoma. Squamous cell lung carcinoma (31.1% of lung cancers) often starts near a central bronchus and commonly shows cavitation and necrosis within the center of the cancer. Adenocarcinoma (29.4% of lung cancers) mostly originates in peripheral lung tissue and is usually associated with smoking. Large cell lung carcinoma (10.7% of lung cancers) is a fast-growing form that develops near the surface of the lung. Common treatments of NSCLC include surgery, chemotherapy, and radiation therapy. In particular, NSCLC is treated with adjuvant chemotherapy (i.e. chemotherapy after surgery). Wu (2009) describes phosphorylation patterns in lung cancer (see Wu (2009) PloS ONE 4 (11) e7994).

Previous studies have shown that SFK inhibitor, PP2 reduces frequency of epileptiform discharges in the hippocampal in vitro model (Salter and Kalia, 2004; Sanna et al., 2000). Saracatinib is more potent than other SFK inhibitors, and has been in clinical trials for Alzheimer's disease (AD) (Nygaard et al., 2015) and breast cancer (Gucalp et al., 2011). Saracatinib is an anilinoquinazoline compound which has high specificity for the tyrosine kinase domains of SFK (Hennequin et al., 2006). In these enzymes, an adenine moiety of ATP is bound to Src kinase domains through hydrogen bond networks. This allows chlorobenzodioxide moiety of quinazoline compounds to sit deep inside the hydrophobic pocket of SFK making number of hydrophobic contacts forming stronger inhibitor-enzyme complex. Moreover, the presence of C5 position on the quinazoline ring, which fits well into enzyme's ribose pocket, makes them even more selective for SFKs thereby increasing their binding affinity and potency (Ballard et al., 2005; Gibson et al., 2002; Hennequin et al., 2006). Furthermore, the SFKs has some enzyme residues present at the entrance of their pocket site, also known as gatekeepers, is another potential feature for the selectivity of quinazolines as inhibitors of SFKs. In contrast to SFKs, the ribose pocket in other kinases is open to wide range of compounds that makes them less selective in nature (Hennequin et al., 2006).

BRIEF SUMMARY OF THE INVENTION

In certain embodiments, methods and pharmaceutical compositions comprising an effective, orally active amount of the Fyn tyrosine kinase inhibitor, for use in preventing or treating epilepsy are provided.

In another embodiment, a method of treating or preventing epilepsy in a mammal in need thereof, the method comprising administering to the mammal a therapeutically effective amount of a Fyn inhibitor. The present invention further provides a method of preventing neuro-inflammation or further neurodegeneration in a mammal in need thereof, the method comprising administering to the mammal a therapeutically effective amount of a Fyn inhibitor.

In certain embodiments, the Fyn inhibitor is selected from the group consisting of a nucleic acid, siRNA, antisense nucleic acid, ribozyme, peptide, antibody, small molecule, antagonist, aptamer, peptidomimetic, and any combinations thereof. In preferred embodiments, the Fyn small molecule inhibitor is selected from the group consisting of saracatinib (AZD0503), bosutinib, dasatinib, ponatinib, PP2, a salt, prodrug or solvate thereof, a derivative thereof, and any combinations thereof.

In certain embodiments, the composition is administered to the mammal by at least one route selected from the group consisting of nasal, inhalational, topical, oral, buccal, rectal, pleural, peritoneal, vaginal, intramuscular, subcutaneous, transdermal, epidural, intratracheal, otic, intraocular, intrathecal, and intravenous routes. In a preferred embodiment administration is oral.

In certain embodiments, the method further comprises administering to the mammal at least one additional agent that treats or prevents epilepsy, or other Fyn tyrosine kinase modulated diseases or disorders in the mammal. In yet other embodiments, the method further comprises administering to the mammal at least one additional agent that improves or prevents epilepsy in the mammal. In yet other embodiments, the composition and at least one additional agent are co-formulated.

In other embodiments, a kit for preventing or treating epilepsy is provided, wherein the kit comprises a pharmaceutical composition of the invention, an applicator, and an instructional material for use thereof. In certain embodiments, the instructional material recites the amount of, and frequency with which, the composition is to be administered to the mammal.

In the preceding embodiments, inhibitors of Fyn tyrosine kinase can be included in pharmaceutical compositions and administered to a mammal suffering from or at risk of a disease, disorder, or condition associated with Fyn tyrosine kinase activation, including but not limited to Parkinson's disease, Alzheimer's disease, Tourette's syndrome, schizophrenia, Huntington's disease, symptoms of attention deficit hyperactivity disorder, drug abuse and clinical depression. In a still further aspect, the invention concerns a method for treating degeneration of neurons in a mammal in need thereof comprising administering to a mammal in need thereof a Fyn tyrosine kinase inhibitor, thereby providing neuroprotection. In another aspect, the pharmaceutical composition may be used in the treatment of diseases, disorders, or conditions associated with neuro-inflammation or neurodegeneration wherein the supporting cells (microglia or glial cells) are hyper-activated as a result of injury. In one aspect, the neuron is a sympathetic, parasympathetic, or enteric, e.g. dorsal root ganglia neurons, motor neurons, and central neurons, e.g. neurons from the spinal cord.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

FIG. 1 is a graphical representation of saracatinib (SAR) crossing the blood brain barrier (BBB), increasing the latency of seizure onset, and reducing seizure severity and morality rate in C57LB/6J mice. The SAR (25 mg/kg) was administered orally 4 h prior to a SHD of kainate (25 mg/kg, i.p.). In FIG. 1B, each dot represents individual animal (*$p<0.0001$, Mann-Whitney).

FIG. 3 is a graphical representation of real-time video-EEG recording and analyses of epileptiform spike and spontaneous non-convulsive seizure (NCS). FIG. 3A shows a representative EEG trace recorded during the SE induced by a RLD of kainate is presented. The behavioral SE was terminated by diazepam (10 mg/kg, i.p.), 2 h after the onset of first convulsive seizure (CS). FIG. 3B shows a segment of the EEG trace covering the stages of seizures before and after the stage 5 seizure and the associated seizure stage-specific power bands are illustrated. The theta and delta power were increased in NCS, while the gamma power was increased during the stage 5 seizure, and the image represents the stage 5 behavior (jumping). (FIG. 3I, *$p<0.0001$, two-way ANOVA between 1 and 119 degrees of freedom, F=70.61; FIG. 3J, $p=0.002$, *$p=0.0006$, Mann-Whitney test).

FIG. 4 is a pictorial and graphical representation of Fyn and pSrc-416 levels in the hippocampus during epileptogenesis. FIG. 4H-iii, vii). In fyn$^{-/-}$ mice, there were also M1 like microglia, but without Fyn (FIG. 4G, x). FIG. 4I shows the M1-like microglia cell quantification. Fyn$^{+/+}$ mice showed a significantly higher percentage of total M1-like phenotype, "reactive" microglia, at all time points when compared to their respective controls. However, a similar increase was observed in the percentage of M1-like microglia in fyn$^{-/-}$ compared to the controls but this difference was not significant at 7d post-SE.

FIG. 5 is a pictorial and graphical representation of the PKCδ (cytosolic and nuclear) and pPKCδ-507 protein levels in the hippocampus during epileptogenesis.

FIG. 6 is a pictorial and graphical representation of caspase-3 and cleaved caspase-3 levels in the hippocampus of $fyn^{+/+}$ and $fyn^{-/-}$ mice during epileptogenesis.

FIG. 7 is a graphical representation of THF-α, IL-1β, and iNOS mRNA expression levels in the hippocampus, and serum IL-6 and IL-12 levels in $fyn^{+/+}$ and $fyn^{-/-}$ mice during epileptogenesis.

FIG. 8 is a pictorial and graphical representation of the Western blot analyses of 4-HNE, gp91$^{phox}$ and 3-NT in the hippocampus of $fyn^{+/+}$ and $fyn^{-/-}$ mice during epileptogenesis.

FIG. 10 is a graphical representation of saracatinib post-treatment in rats significantly reducing the number of spontaneous CS and the epileptiform spiking activity during 28 days of post-SE period. FIG. 10B, *$p=0.017$, Mann-Whitney). FIG. 10E, *$p=0.0003$, Mann-Whitney test).

FIG. 13 shows a graphical representation of the comparison of spontaneous seizure frequency between the vehicle (Veh) and saracatinib (SAR) treated rats (n=8 for control and 7 for SAR). Seizure event (SE) was induced with kainic acid (KA) in both groups, and they were continuously video-EEG monitored for four months.

DETAILED DESCRIPTION OF THE INVENTION

Figure 1A:
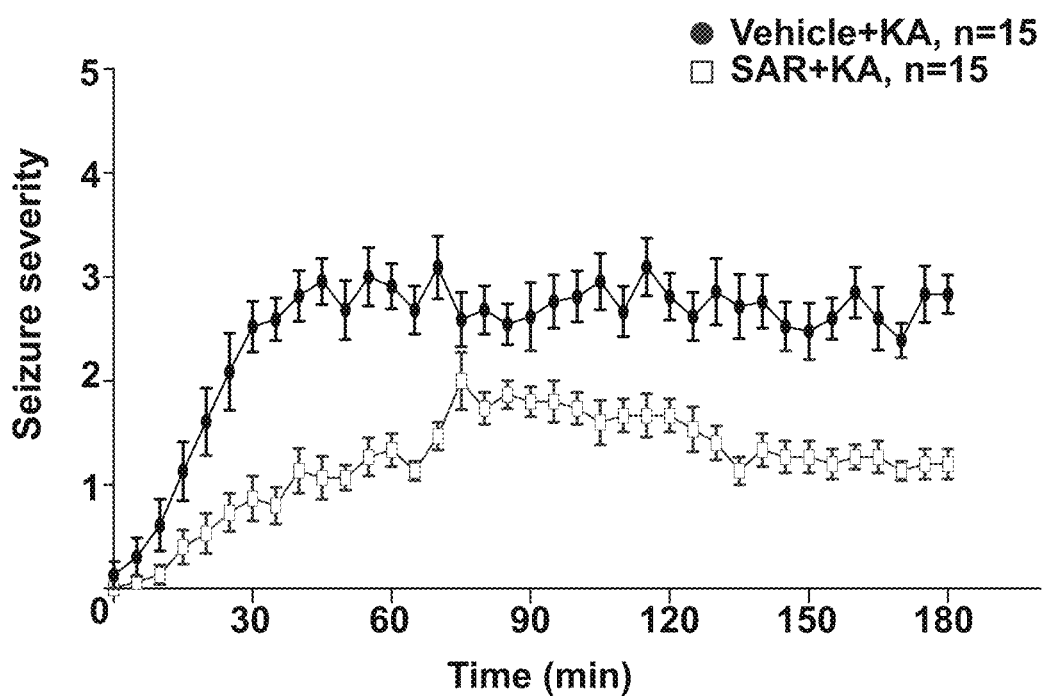
FIGS. 1A and 1B show the comparison of the time course of behavioral seizure event between the groups (FIG. 1A) during the first 3 h after kainate injection (*$p<0.0001$, two-way ANOVA between 1 and 1271 degrees of freedom, F=502.65, n=15 for each group).

The following definitions and introductory matters are provided to facilitate an understanding of the present invention.

Numeric ranges recited within the specification, including ranges of "greater than," "at least," or "less than" a numeric value, are inclusive of the numbers defining the range and include each integer within the defined range.

The singular terms "a", "an", and "the" include plural referents unless context clearly indicates otherwise. Similarly, the word "or" is intended to include "and" unless the context clearly indicate otherwise. The word "or" means any one member of a particular list and also includes any combination of members of that list.

As used herein, the term "Fyn tyrosine kinase inhibitor" includes any compound capable of downregulating, decreasing, reducing, suppressing or inactivating the amount and/or activity of Fyn tyrosine kinase. Generally, said inhibitors may be proteins, oligo- and polypeptides, polynucleotides, genes, lipid, polysaccharide, drugs, small chemical molecules, or other chemical moieties. Inhibitors for use with the invention may function to inhibit Fyn tyrosine kinase by any number of ways, including decreasing Fyn tyrosine kinase mRNA or protein levels or by blocking the activation of Fyn tyrosine kinase or its activity, for example, through inhibiting or decreasing proteolytic cleavage of Fyn tyrosine kinase using a Fyn tyrosine kinase peptide cleavage inhibitor. Compounds that decrease activity of Fyn tyrosine kinase downstream of Fyn tyrosine kinase in its pathway and decrease products or activity of Fyn tyrosine kinase targets, for example, PP2A and TH, or decrease activity upstream of Fyn tyrosine kinase are also within the scope of Fyn tyrosine kinase inhibitors of the present invention.

In one embodiment, the epilepsy can be classified according the electroclinical syndromes following the Classification and Terminology of the International League Against Epilepsy (ILAE) (Berg et al., 2010). These syndromes can be categorized by age at onset, distinctive constellations (surgical syndromes), and structural-metabolic causes: (A) age at onset: (i) neonatal period includes Benign familial neonatal epilepsy (BFNE), Early myoclonic encephalopathy (EME), Ohtahara syndrome. (ii) Infancy period includes Epilepsy of infancy with migrating focal seizures, West syndrome, Myoclonic epilepsy in infancy (MEI), Benign infantile epilepsy, Benign familial infantile epilepsy, Dravet syndrome, Myoclonic encephalopathy in nonprogressive disorders. (iii) Childhood period includes Febrile seizures plus (FS+), Panayiotopoulos syndrome, Epilepsy with myoclonic atonic (previously astatic) seizures, Benign epilepsy with centrotemporal spikes (BECTS), Autosomal-dominant nocturnal frontal lobe epilepsy (ADNFLE), Late onset childhood occipital epilepsy (Gastaut type), Epilepsy with myoclonic absences, Lennox-Gastaut syndrome, Epileptic encephalopathy with continuous spike-and-wave during sleep (CSWS), Landau-Kleffner syndrome (LKS), Childhood absence epilepsy (CAE). (iv) Adolescence Adult period includes Juvenile absence epilepsy (JAE) Juvenile myoclonic epilepsy (JME), Epilepsy with generalized tonic—clonic seizures alone, Progressive myoclonus epilepsies (PME), Autosomal dominant epilepsy with auditory features (ADEAF), Other familial temporal lobe epilepsies. (v) Variable age onset includes Familial focal epilepsy with variable foci (childhood to adult), Reflex epilepsies. (B) Distinctive constellations (surgical syndromes) include Mesial Temporal Lobe Epilepsy (MTLE), Rasmussen syndrome, Gelastic seizures with hypothalamic hamartoma, Hemiconvulsion-hemiplegia-epilepsy. (C) Epilepsies attributed to and organized by structural-metabolic causes include Malformations of cortical development (hemimegalencephaly, heterotopias, etc.), Neurocutaneous syndromes (tuberous sclerosis complex, Sturge-Weber, etc.), Tumor, Infection, Trauma, Angioma, Perinatal insults, Stroke, Etc.

In another embodiment, the epilepsy may be a benign Rolandic epilepsy, a frontal lobe epilepsy, an infantile spasms, a juvenile myoclonic epilepsy, a juvenile absence epilepsy, a childhood absence epilepsy (pyknolepsy), a hot water epilepsy, a Lennox-Gastaut syndrome, a Landau-Kleffner syndrome, a Dravet syndrome, a progressive myoclonus epilepsies, a reflex epilepsy, a Rasmussen's syndrome, a temporal lobe epilepsy, a limbic epilepsy, a status epilepticus, an abdominal epilepsy, a massive bilateral myoclonus, a catamenial epilepsy, a Jacksonian seizure disorder, a Lafora disease or photosensitive epilepsy.

In a particular embodiment, the epilepsy is a temporal lobe epilepsy.

In one embodiment, the epilepsy is a chronic epilepsy.

In another embodiment, the epilepsy can be a refractory epilepsy.

As used herein, the term "refractory epilepsy" denotes an epilepsy which is refractory to current pharmaceutical treatment that is to say that current pharmaceutical treatment does not allow a treatment of patients (see for example Daria J. Englot et. al., 2013).

In a particular embodiment, the refractory epilepsy is a chronic refractory epilepsy.

As used herein the term "Temporal Lobe Epilepsy" or "TLE" denotes a chronic neurological condition characterized by chronic and recurrent seizures (epilepsy) which originate in the temporal lobe of the brain. This disease is different from acute seizures in naive brain tissue since in TLE morpho-functional re-organization of neuronal network and sprouting of hippocampal mossy fibers appears whereas in acute seizures such re-organization does not occur.

As used herein, the term "neurodegeneration" refers the damage, for example, through inflammation, or death of a cell in the central nervous system, for example, a neuron. Neurodegeneration refers to any pathological changes in neuronal cells, including, without limitation, death or loss of neuronal cells and any changes that precede cell death. The pathological changes may be spontaneous or may be induced by any event and include, for example, pathological changes associated with inflammation or apoptosis. The neurons may be any neurons, including without limitation sensory, sympathetic, parasympathetic, or enteric, e.g. dorsal root ganglia neurons, motor neurons, and central neurons, e.g. neurons from the spinal cord.

As used herein, the terms "neurodegenerative disorder" or "neurodegenerative disease" refer broadly to disorders or diseases that affect the nervous system having damage or death of a cell of the central nervous system, including but not limited to Parkinson's disease, Alzheimer's disease, Huntington's disease and amyotrophic lateral sclerosis.

As used herein, the term "compound" refers to a polynucleotide, a protein, a polypeptide, a peptide, an antibody, an immunoglobulin, a ligand, a cytokine, a growth factor, a nucleic acid, a lipid, membrane, a carbohydrate, a drug, a prodrug, or a small molecule or a fragment thereof.

As used herein, the term "modulates" refers to the ability of a compound to alter the mRNA or protein expression level or kinase activity or phosphatase activity of a protein.

As used herein, the term "pharmaceutically acceptable carrier" refers to any carrier, diluent, excipient, wetting agent, buffering agent, suspending agent, lubricating agent, adjuvant, vehicle, delivery system, emulsifier, disintegrant, absorbent, preservative, surfactant, colorant, flavorant, or sweetener, preferably non-toxic, that would be suitable for use in a pharmaceutical composition.

As used herein, the terms "pharmaceutically effective" or "therapeutically effective" shall mean an amount of a Fyn tyrosine kinase inhibitor that is sufficient to show a meaningful patient benefit, i.e., treatment, prevention, amelioration, or a decrease in the frequency of the condition or symptom being treated. The Fyn tyrosine kinase inhibitor may be administered in the form of a pharmaceutical composition with a pharmaceutically acceptable carrier.

As used herein, the term "treating" refers to: (i) preventing a disease, disorder or condition from occurring in an animal or human that may be predisposed to the disease, disorder and/or condition but has not yet been diagnosed as having it; (ii) inhibiting the disease, disorder or condition, i.e., arresting its development; and/or (iii) relieving the disease, disorder or condition, i.e., causing regression of the disease, disorder and/or condition. For example, with respect to epilepsy, treatment may be measured by quantitatively or qualitatively to determine the presence/absence of epileptic symptoms, or its progression or regression using, for example, symptoms associated with the disease or clinical indications associated with the pathology.

As used herein, the term "polypeptide" is interpreted to mean a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer. The term "protein" typically refers to large polypeptides. The term "peptide" typically refers to short polypeptides. "Polypeptide(s)" refers to any peptide or protein comprising two or more amino acids joined to each other by peptide bonds or modified peptide bonds. "Polypeptide(s)" refers to both short chains, commonly referred to as peptides, oligopeptides and oligomers and to longer chains generally referred to as proteins. Polypeptides may contain amino acids other than the 20 gene encoded amino acids. "Polypeptide(s)" include those modified either by natural processes, such as processing and other post-translational modifications, but also by chemical modification techniques. Such modifications are well described in basic texts and in more detailed monographs, as well as in a voluminous research literature, and they are well-known to those of skill in the art. It will be appreciated that the same type of modification may be present in the same or varying degree at several sites in a given polypeptide. Also, a given polypeptide may contain many types of modifications. Modifications can occur anywhere in a polypeptide, including the peptide backbone, the amino acid side-chains, and the amino or carboxyl termini. Modifications include, for example, acetylation, acylation, ADPribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-link formation of cysteine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxylation and ADP-ribosylation, selenoylation, sulfation, transfer-RNA mediated addition of amino acids to proteins, such as arginylation, and ubiquitination. See, for instance, PROTEINS—STRUCTURE AND MOLECULAR PROPERTIES, 2nd Ed., T. E. Creighton, W. H. Freeman and Company, New York (1993) and Wold, F., Posttranslational Protein Modifications: Perspectives and Prospects, pgs. 1 12 in POSTTRANSLATIONAL COVALENT MODIFICATION OF PROTEINS, B. C. Johnson, Ed., Academic Press, New York (1983); Seifter et al., Meth. Enzymol. 182:626 646 (1990) and Rattan et al., Protein Synthesis: Posttranslational Modifications and Aging, Ann. N.Y. Acad. Sci. 663: 48 62 (1992). Polypeptides may be branched or cyclic, with or without branching. Cyclic, branched and branched circular polypeptides may result from post-translational natural processes and may be made by entirely synthetic methods, as well.

As used herein, the term "polynucleotide" is interpreted to mean a polymer composed of nucleotide units. Polynucleotides include naturally occurring nucleic acids, such as deoxyribonucleic acid ("DNA") and ribonucleic acid ("RNA") as well as nucleic acid analogs. Nucleic acid analogs include those which include non-naturally occurring bases, nucleotides that engage in linkages with other nucleotides other than the naturally occurring phosphodiester bond or which include bases attached through linkages other than phosphodiester bonds. Thus, nucleotide analogs include, for example and without limitation, phosphorothioates, phosphorodithioates, phosphorotriesters, phosphoramidates, boranophosphates, methylphosphonates, chiral-methyl phosphonates, 2-O-methyl ribonucleotides, peptide-nucleic acids (PNAs), and the like. Such polynucleotides can be synthesized, for example, using an automated DNA synthesizer. The term "nucleic acid" typically refers to large polynucleotides. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces T.

As used herein, the term "proinflammatory marker" is a molecule, including a polynucleotide or polypeptide sequence, that is associated with the activation or maintenance of an inflammatory response. A multitude of such markers are known in the art, such as, but not limited to TNF-α, IL-β, IL-6, IL-12, and iNOS. See for example the reference NF-κB signaling pathway map at KEGG (Kyoto Encyclopedia of Genes and Genomes: http://www.genome.jp/kegg-bin/show_pathway?org_name=ko&mapno=04064&mapscale=&show_description=hide).

As used herein, the term "nitro-oxidative stress marker" is a molecule involved in redox signaling to create reactive nitrogen species (RNS) or reactive oxygen species (ROS). Examples of nitro-oxidative stress markers are known in the art and include, but are not limited to, 4-HNE, gp91$^{Phox}$, superoxide dismutase, and 3-NT.

Methods for Treating or Preventing Epilepsy

Certain embodiments relate generally to compositions and methods for treating and preventing Fyn kinase-modulated disease in a subject in need thereof. The invention is useful, for example, for slowing, protecting from the effects of, or halting epilepsy. In certain embodiments, the disease or disorder contemplated within the invention is associated with pathological Fyn kinase-mediating signaling. Non-limiting examples of Fyn kinase-modulated disease that are treatable or preventable with the compositions and methods of the present invention include, but are not limited to, epilepsy, Parkinson's Disease (PD), Alzheimer's Disease (AD), amnestic mild cognitive impairment (MCI), Down syndrome dementia, traumatic brain injury, Lewy body dementia, fronto-temporal dementia, and after stroke aphasia. It should be noted that the present invention is not limited to a particular type of Fyn kinase-modulated disease. The subject may be an animal, preferably a mammal or human.

Other embodiments also provide a pharmaceutical composition for treating a Fyn kinase-modulated disease in a subject, wherein the composition comprises an inhibitor of Fyn receptor kinase activity and a carrier. For example, in certain embodiments, the composition comprises an isolated nucleic acid, isolated peptide, antibody, small molecule, antagonist, aptamer, or peptidomimetic that reduces the activity of Fyn.

In other embodiments, a composition for treating a Fyn kinase-modulated disease in a subject, wherein the composition comprises an inhibitor of Fyn tyrosine receptor kinase expression and a carrier are provided. For example, in certain embodiments, the composition comprises an isolated nucleic acid (e.g., siRNA, ribozyme, antisense RNA, etc.) that reduces the expression level of Fyn receptor kinase in a cell.

In certain embodiments, the Fyn receptor kinase inhibitor is prepared as a prodrug. A prodrug is an agent converted into the parent drug in vivo. In one embodiment, upon in vivo administration, a prodrug is chemically converted to the biologically, pharmaceutically or therapeutically active form of the compound. In other embodiments, a prodrug is enzymatically metabolized by one or more steps or processes to the biologically, pharmaceutically or therapeutically active form of the compound. Prodrugs are known to those skilled in the art, and may be prepared using methodology described in the art. Compounds described herein also include isotopically labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to 2H, 3H, 11C, 13C, 14C, 36Cl, 18F, 123I, 125I, 13N, 15N, 15O, 17O, 18O, 32P, and 35S. In one embodiment, the isotope comprises deuterium. In certain embodiments, isotopically labeled compounds are useful in drug and/or substrate tissue distribution studies. In another embodiment, substitution with heavier isotopes such as deuterium affords greater metabolic stability (for example, increased in vivo half-life or reduced dosage requirements). In yet another embodiment, substitution with positron emitting isotopes, such as 11C, 18F, 15O and 13N is useful in Positron Emission Topography (PET) studies for examining substrate receptor occupancy. Isotopically labeled compounds are prepared by any suitable method or by processes using an appropriate isotopically-labeled reagent in place of the non-labeled reagent otherwise employed.

In one embodiment, the compounds described herein are labeled by other means, including, but not limited to, the use of chromophores or fluorescent moieties, bioluminescent labels, or chemiluminescent labels.

In one embodiment the inhibitor is a small molecule inhibitor of Fyn tyrosine selected from the group consisting of saracatinib, bosutinib, dasatinib, ponatinib, PP2, a pharmaceutically acceptable salt thereof, a derivative thereof, and any combinations thereof. In a preferred embodiment the small molecule inhibitor is saracatinib, otherwise known as AZD0530, or N-(5-chlorobenzo[d][1,3]dioxol-4-yl)-7-(2-(4-methyl piperazin-1-yl)ethoxy)-5-(tetrahydro-2H-pyran-4-yloxy)quinazolin-4-amine), or pharmaceutically acceptable salts, prodrugs, solvates or derivatives thereof.

Saracatinib (AZD0530), has the following chemical formula:

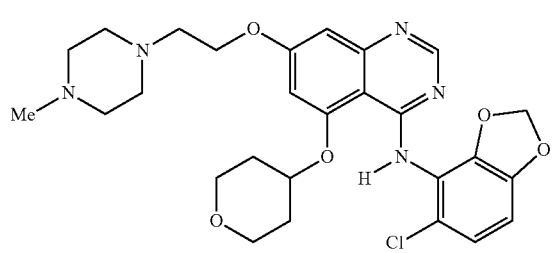 [SMILES: CN1CCN(CCOc2cc(OC3CCOCC3)c3c(Nc4c(Cl)ccc5c4OCO5)ncnc3c2)CC1]

N-(5-chloro-1,3-benzodioxol-4-yl)-7-[2-(4-methylpiperazin-1-yl)ethoxy]-5-(oxan-4-yloxy)quinazolin-4-amine and is commercially available through AstraZeneca. The compound is currently used to treat advanced solid tumors in pancreatic, ovarian, prostate, osteosarcoma, melanoma, and colon cancer.

Thus, the invention provides a pharmaceutical composition comprising an effective amount of saracatinib, or a pharmaceutically acceptable salt, solvate or prodrug thereof, and a carrier.

In some embodiments an effective amount can include an amount sufficient for a trough cerebral spinal fluid (CSF)

concentration of saracatinib in the mammal of at least about 0.9 nM. In other embodiments, the trough CSF concentration of saracatinib in the mammal is at least about 2.1 nM. In yet other embodiments, the trough CSF concentration of saracatinib in the mammal is at least about 2.5 nM. In yet other embodiments, the trough CSF concentration of saracatinib in the mammal ranges from about 0.9 nM to about 2.2 nM. In yet other embodiments, the trough CSF concentration of saracatinib in the mammal ranges from about 2.1 nM to about 8.3 nM. In yet other embodiments, the trough CSF concentration of saracatinib in the mammal ranges from about 2.5 nM to about 14.0 nM. In yet other embodiments, the trough CSF concentration of saracatinib in the mammal ranges from about 0.9 nM to about 14.0 nM. In yet other embodiments, the average brain concentration of saracatinib in the mammal is selected from the group consisting of at least about 3 nM, at least about 7 nM, and at least about 8 nM. In yet other embodiments, the average brain concentration of saracatinib in the mammal ranges from about 3 to about 46 nM.

In certain embodiments, the saracatinib is saracatinib free base. In other embodiments, the saracatinib is saracatinib difumarate. In yet other embodiments, the saracatinib is selected from the group consisting of saracatinib free base, saracatinib difumarate, and any combinations thereof.

In certain embodiments, the methods and compositions further comprise administering to the mammal at least one additional or a second agent that treats or prevents epilepsy or epileptic symptoms. In yet other embodiments, the method further comprises administering to the mammal at least one additional agent that improves or prevents further neurodegeneration in the mammal. Pharmaceutical compositions of the invention can include an additional agent that is co-formulated with the Fyn tyrosine receptor inhibitor.

Examples of additional agents that treat or prevent epilepsy and/or neurodegeneration and may be co-administered according to the invention include but are not limited to:

Antiepileptic drugs (AEDs) phenytoin, carbamazepine, clonazepam, ethosuximide, valproic acid, barbiturates, felbamate, gabapentin, lamotrigine, oxcarbazepine, tiagabine, topiramate, vigabartrin, zonisamide and levetiracetam;

Carbidopa—currently the most effective Parkinson's disease medication. It is a natural chemical that is converted to dopamine;

Levodopa which is combined with carbidopa (Rytary, Sinemet), which protects levodopa from premature conversion to dopamine outside of the brain, which prevents or lessens side effects such as nausea;

Carbidopa-levodopa infusion, Duopa, carbidopa and levodopa which is administered through a feeding tube that delivers the medication in a gel form directly to the small intestine;

Dopamine agonists. Agents which mimic dopamine effects in the brain. Examples of dopamine antagonists include pramipexole (Mirapex), ropinirole (Requip) and rotigotine (given as a patch, Neupro). A short-acting injectable dopamine agonist, apomorphine (Apokyn), is used for quick relief;

MAO-B inhibitors. These medications include selegiline (Eldepryl, Zelapar) and rasagiline (Azilect). They help prevent the breakdown of brain dopamine by inhibiting the brain enzyme monoamine oxidase B (MAO-B). This enzyme metabolizes brain dopamine;

Catechol-O-methyltransferase (COMT) inhibitors. Entacapone (Comtan) is the primary medication from this class. This medication mildly prolongs the effect of levodopa therapy by blocking an enzyme that breaks down dopamine.

Tolcapone (Tasmar) is another COMT inhibitor that is rarely prescribed due to a risk of liver damage; anticholinergic medications such as benztropine (Cogentin) or trihexyphenidyl; and Amantadine provides short-term relief of symptoms of mild, early-stage Parkinson's disease. It may also be given with carbidopa-levodopa therapy during the later stages of Parkinson's disease to control involuntary movements (dyskinesias) induced by carbidopa-levodopa.

In another aspect of the invention the Fyn kinase inhibitor may be combined with surgical procedures. One example is deep brain stimulation. In deep brain stimulation (DBS), surgeons implant electrodes into a specific part of the brain. The electrodes are connected to a generator implanted in the chest near the collarbone that sends electrical pulses to the brain and can reduce epileptic disease symptoms. DBS can stabilize medication fluctuations, reduce or halt involuntary movements (dyskinesias), reduce tremor, reduce rigidity, and improve slowing of movement.

In another aspect of the invention the Fyn tyrosine kinase inhibitor is a polynucleotide, polynucleotide that includes but is not limited to an antisense polynucleotide, ribozyme, RNA interference (RNAi) molecule, small hairpin RNA (shRNA), triple helix polynucleotide and the like, where the nucleotide sequence of such polynucleotides are the nucleotide sequences of DNA and/or RNA. Antisense technology may be used to achieve Fyn tyrosine kinase-specific interference, using for example, stoichiometric amounts of single-stranded nucleic acid complementary to the messenger RNA of Fyn tyrosine kinase which are introduced into the cell.

In one embodiment, an RNA interference (RNAi) molecule is used as a Fyn tyrosine kinase inhibitor, decreasing Fyn tyrosine kinase gene expression in a cell. In another aspect, the Fyn tyrosine kinase inhibitor is a siRNA molecule for targeting Fyn tyrosine kinase in a mammal, including without limitation, Fyn tyrosine kinase siRNA for a mouse, rat, monkey, or human.

In one embodiment, the compositions and methods of the present invention includes a Fyn tyrosine kinase inhibitor of at least one Fyn tyrosine kinase siRNA. In one aspect, the Fyn tyrosine kinase inhibitor includes a combination of differing Fyn tyrosine kinase siRNA molecules. Materials and methods to produce Fyn tyrosine kinase siRNA molecules are known in the art. The Fyn tyrosine kinase siRNA molecules may be produced by a number of methods, including the use of commercially available kits, for example, The SILENCER™ siRNA Construction Kit (Ambion, Austin, Tex.), a mammalian siRNA Fyn tyrosine kinase expression plasmid (Upstate Cell Signaling Solutions, Charlottesville, Va.), or obtained from MoleculA (Columbia, Md.).

The siRNA can be administered directly, for example, intracellularly, into a cell to mediate RNA interference (Elbashir et al., 2001, Nature 411:494 498) or administered extracellularly into a cavity, interstitial space, into the circulation of an organism, introduced orally, or may be administered by contacting the cell with a solution containing the RNA. Physical methods of introducing polynucleotides, for example, injection directly into the cell or extracellular injection into the organism, may also be used. Other methods known in the art for introducing polynucleotides to cells may be used, such as viral vectors, viruses, lipid-mediated carrier transport, chemical-mediated transport, such as calcium phosphate, electroporation, the like. siRNA can be made using, for example, chemical synthesis or in vitro or in vivo transcription. A number of expression vectors have also been developed to continually express siRNAs in transiently and stably transfected mammalian cells (Brummelkamp et al., 2002 Science 296:550 553; Sui et al., 2002, PNAS 99(6):5515 5520; Paul et al., 2002, Nature Biotechnol. 20:505 508).

In one embodiment, the Fyn tyrosine kinase inhibitor is a small hairpin RNA (shRNA), which is processed in vivo into siRNA-like molecules capable of carrying out gene-specific silencing. RNA duplex formation may be initiated either inside or outside the cell. The RNA may be introduced in an amount which allows delivery of at least one copy per cell. Higher doses (e.g., at least 5, 10, 100, 500 or 1000 copies per cell) of double-stranded material may yield more effective inhibition; lower doses may also be useful for specific applications. The RNA molecule may be at least 10, 12, 15, 20, 21, 22, 23, 24, 25, 30, nucleotides in length.

RNA containing a polynucleotide sequence identical to a portion of Fyn tyrosine kinase gene is preferred for inhibition. RNA sequences with insertions, deletions, and single point mutations relative to the target sequence of Fyn tyrosine kinase may also be effective for inhibition. Thus, one hundred percent sequence identity between the RNA and the target gene is not required to practice the present invention. Greater than 80% or 90% sequence identity or 100% sequence identity, between the inhibitory RNA and the portion of the Fyn tyrosine kinase is preferred. Thus, sequence identity may be optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group).

Fyn tyrosine kinase inhibitors can be delivered intracellularly using a lipid-mediated protein delivery system. Kaul S, Kanthasamy A, Kitazawa M, Anantharam V, Kanthasamy A G, Caspase-3 dependent proteolytic activation of Fyn tyrosine kinasemediates and regulates 1-methyl-4-phenylpyridinium (MPP+)-induced apoptotic cell death in dopaminergic cells: relevance to oxidative stress in dopaminergic degeneration. Eur J Neurosci. 2003 September; 18(6): 1387-401. The incomplete cleavage of PKCδ or PKCδ-mediated apoptotic inhibition can be measured using standard techniques known to one skilled in the art. Yoshimura S, Banno Y, Nakashima S, Takenaka K, Sakai H, Nishimura Y, Sakai N, Shimizu S, Eguchi Y, Tsujimoto Y, Nozawa Y. Ceramide formation leads to caspase-3 activation during hypoxic PC12 cell death. Inhibitory effects of Bcl-2 on ceramide formation and caspase-3 activation. J Biol Chem. 1998 Mar. 20; 273(12):6921-7 (describing a method to determine caspase activity). Kaul S, Kanthasamy A, Kitazawa M, Anantharam V, Kanthasamy A G, Caspase-3 dependent proteolytic activation of Fyn tyrosine kinasemediates and regulates 1-methyl-4-phenylpyridinium (MPP+)-induced apoptotic cell death in dopaminergic cells: relevance to oxidative stress in dopaminergic degeneration. Eur J Neurosci. 2003 September; 18(6):1387-401) (describing the use of PKCδ-specific antibodies). Reyland M E, Anderson S M, Matassa A A, Barzen K A, Quissell D O. Fyn tyrosine kinase is essential for etoposide-induced apoptosis in salivary gland acinar cells. J Biol Chem. 1999 Jul. 2; 274(27):19115-23.), Anantharam V, Kitazawa M, Wagner J, Kaul S, Kanthasamy A G. Caspase-3-dependent proteolytic cleavage of protein kinase C delta is essential for oxidative stress-mediated dopaminergic cell death after exposure to methylcyclopentadienyl manganese tricarbonyl. J Neurosci. 2002 Mar. 1; 22(5):1738-51, (describing assaying for Fyn tyrosine kinase enzymatic activity using an immunoprecipitation assay).

In another embodiment of the invention, other agents such as peptides, small molecules and the like may be screened to identify those that alter Fyn tyrosine kinase activity, particularly the ability of Fyn tyrosine kinase upregulation in response to inflammatory signals such as TNFα or LPB to identify additional treating agents. The Fyn tyrosine kinase inhibitor may directly alter the interaction of proteins in the Fyn tyrosine kinase pathway, for example, by inhibiting the activity of a kinase or phosphorylase in the pathway or by interfering with a step of the pathway.

The inhibition or reduction of Fyn tyrosine kinase activity can be determined using a variety of methods and assays routine to one skilled in the art, for example, determining the phosphorylation and/or activation of a Fyn tyrosine kinase kinase's target. Generally, a purified or partially purified Fyn tyrosine kinase is incubated with a peptide comprising the target sequence of Fyn tyrosine kinase under conditions suitable for the kinase to phosphorylate its target sequence of amino acids (i.e., protein, polypeptide). The particular requirements of the kinase may be determined empirically by one of skill in the art, or the conditions that have been published for a particular kinase may be used. The extent of phosphorylation of the target peptide is determined in the presence and absence of the test compound and may be determined in the presence of varying concentrations of the test compound. The phosphorylation rate may be determined by any means known in the art including electrophoretic assays, chromatographic assays, phosphocellulose assays and the like.

In an electrophoretic assay, a radiolabeled phosphate donor such as ATP or GTP is incubated with the peptide substrate in the presence of a kinase. The phosphorylated substrate versus the phosphate donor (e.g., ATP, GTP) is separated via thin-layer electrophoresis (Hunter J. Biol. Chem. 257:4843, 1982; incorporated herein by reference). Any matrix may be used in the electrophoresis step including polyacrylamide, cellulose, etc. The extent of phosphorylation may then be determined by autoradiography or scintillation counting.

The labeled phosphate donor may be separated from the phosphorylated amino acid sequence by standard chromatography techniques. Any matrix may be used to affect the separation including ion exchange resins, PEI cellulose, silica gel, etc. Standard column chromatography methods may be used, or HPLC methods may be used for faster cleaner separations. The radio-labeled peptides are detected by scintillation counting to determine the phosphorylation rate.

Another method which is historically the most popular is the phosphocellulose paper assay, first described by Witt et al. (Witt et al. Anal. Biochem. 66:253, 1975; incorporated herein by reference). Immunological methods may also be used to detect the phosphorylation of a peptide or protein substrate. For example, anti-phosphotyrosine or anti-phosphoserine antibodies may be used in the detection or precipitation of phosphorylated amino acid sequences. For example, multiple Fyn tyrosine kinase antibodies that detect the phosphorylated and unphosphorylated forms of Fyn tyrosine kinase are commercially available. (Cell signaling, Beverly, Mass. and Santa Cruz, Santa Cruz, Calif.).

In comparing the rates of phosphorylation in the presence and absence of the test compound, the compound should lead to at least a 10% decrease in the rate of phosphorylation, more preferably at least 25%, and most preferably at least 40%. These decreases are preferably obtained at micromolar concentrations of the compound and more preferably nanomolar concentrations (e.g., less than 100 nM).

In another aspect, the invention includes determining whether a potential Fyn tyrosine kinase inhibitor inhibits Fyn tyrosine kinase activity. The ability of a Fyn tyrosine kinase inhibitor to decrease Fyn tyrosine kinase activity, for example, neurodegeneration can be assessed using standard techniques known to one skilled in the art, including commercially available assays. These include apoptotic DNA Ladder assays, Cell Death Detection ELISAPLUS (from Roche Applied Sciences), Caspase-3 Activity Assay PLUS (from Roche Applied Sciences), terminal deoxynucleotidyl transferase-mediated dUTP [deoxy-uridine triphosphate] nick end labeling (TUNEL) assays. DNA-binding dyes or stains such as Hoechst 3342 or DAPI or propidium iodide may be used to assess nuclear morphology and DNA damage. Kaul S, Kanthasamy A, Kitazawa M, Anantharam V, Kanthasamy A G, Caspase-3 dependent proteolytic activation of Fyn tyrosine kinasemediates and regulates 1-methyl-4-phenylpyridinium (MPP+)-induced apoptotic cell death in dopaminergic cells: relevance to oxidative stress in dopaminergic degeneration. Eur J Neurosci. 2003 September; 18(6): 1387-401.

In one aspect, the method includes administering a Fyn tyrosine kinase inhibitor. A Fyn tyrosine kinase inhibitor may be administered to an individual by various routes including, for example, orally or parenterally, such as intravenously, intramuscularly, subcutaneously, intraorbitally, intracapsularly, intraperitoneally, intrarectally intracisternally or by passive or facilitated absorption through the skin using, for example, a skin patch or transdermal iontophoresis, respectively. Furthermore, a composition comprising a Fyn tyrosine kinase inhibitor can be administered by injection, intubation, orally or topically, the latter of which can be passive, for example, by direct application of an ointment or powder, or active, for example, using a nasal spray or inhalant. A Fyn tyrosine kinase inhibitor also can be administered as a topical spray or an inhalant, in which case one component of the composition is an appropriate propellant.

The skilled artisan can readily perform the in vivo tests to determine, the amount or dose of Fyn tyrosine kinase inhibitor to administer, the formulation of the Fyn tyrosine kinase inhibitor, the route of administration of the Fyn tyrosine kinase inhibitor, and the time at which neurodegeneration or neuroprotection and dopamine synthesis or levels should be assessed.

Toxicity and efficacy of the prophylactic and/or therapeutic protocols of the instant invention can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Prophylactic and/or therapeutic agents that exhibit large therapeutic indices are preferred. While prophylactic and/or therapeutic agents that exhibit toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of the prophylactic and/or therapeutic agents for use in humans. The dosage of such agents lies preferably within a range of circulating concentrations that include the ED50 with little or no toxicity. The dosage may vary within this range depending upon the dosage form employed and the route of administration utilized. For any agent used in the method of the invention, the therapeutically effective dose can be estimated initially from cell culture assays. A dose may be formulated in animal models to achieve a concentration range that includes the IC50 (i.e., the concentration of the test compound that achieves a half-maximal inhibition of symptoms) as determined in cell culture. Such information can be used to more accurately determine useful doses in humans. Levels in plasma and cerebral spinal fluid may be measured, for example, by high performance liquid chromatography.

Neurodegeneration or neuroprotection can be detected using any number of methods. Histological, neurochemical and biochemical markers of dopamine producing cells. These techniques are routine and well-known to one skilled in the art. They include, for example, terminal deoxynucleotidyl transferase-mediated dUTP-X3' nick end-labeling (TUNEL) assays that detect the free 3' OH strand breaks resulting from DNA degradation which is associated with apoptosis (J Cell Biol 199: 493, 1992). In addition, kits that measure apoptotic cell death are also commercially available and include, for example, In Situ Cell Death Detection kit; Boehringer Mannheim, Mannheim or ApoTag, Oncor, Gaithersburg, Md.). Preparation of neuronal sections for apoptosis staining using the TUNEL technique is described in (Gorczyca, (1993) Cancer Res 53:1945-51). Apoptosis can also be detected using electrophoresis of the soluble DNA fraction isolated from neuronal cells by quantifying the ladder-like appearance as described in (PNAS 95: 2498, 1998) or using DNA binding dyes Hoechst 33342 and propidium iodide flow cytometry assay described in Dengler et al., (1995) Anticancer Drugs. 6:522-32.

The present invention also provides kits that can be used in the above methods. In one embodiment, a kit comprises at least one Fyn tyrosine kinase inhibitor, and optimally a second treating agent, in one or more containers, useful for the treatment of a disorder, disease, or condition associated with epilepsy. Optionally associated with such container(s) can be a notice in the form prescribed by a governmental agency regulating the manufacture, use or sale of pharmaceuticals or biological products, which notice reflects approval by the agency of manufacture, use or sale for human administration.

All publications, patents and patent applications identified herein are incorporated by reference, as though set forth herein in full. The invention being thus described, it will be apparent to those skilled in the art that the same may be varied in many ways without departing from the spirit and scope of the invention. Such variations are included within the scope of the following claims.

The invention is further illustrated by the following specific examples which are not intended in any way to limit the scope of the invention.

EXAMPLES

Example 1

Chemoconvulsant-induced status epilepticus in rodents can lead to the development of temporal lobe epilepsy (TLE). This may be due to sustained microglial activation causing neuro-inflammation resulting in lipid peroxidation, reactive gliosis, hippocampal neurodegeneration, reorganization of neural circuits, and hyper-synchronicity. We unexpectedly found fyn kinase, a non-receptor tyrosine kinase, upregulation in microglial cells in a mouse kainate (KA) model of TLE.

Materials and Methods

We tested Fyn knockout mice (fyn$^{-/-}$), bred on C57BL/6J hybrid background mouse (fyn$^{+/+}$), and in wildtype C57BL/6J mice treated with the fyn kinase inhibitor, Saracatinib (AZ0305, 25 mg/kg, oral, single dose) 4 h prior to the induction of SE with KA (5 mg/kg, i.p. at 30 min intervals or as a single high dose of 25 mg/kg). Two hours after the established SE, the behavioral SE was terminated with diazepam (10 mg/kg, i.p.). The animals were euthanized with pentobarbitone (100 mg/kg, i.p.) at 4 h, 24 h and 7d (for IHC & WB) and 4 weeks (video-EEG group) post-SE. The brain, serum, and cerebrospinal fluid (CSF) were collected for various analyses. The brain tissues were processed for IHC and Western blot using the standard methodology described in Puttachary et al., 1400W, a highly selective inducible nitric oxide synthase inhibitor is a potential disease modifier in the rat kainite model of temporal lobe epilepsy, *Neurobiol Dis;* 2016; 93:184-200. We examined the time-dependent activation of fyn in microglial cells and initiation of neuro-inflammatory and neurodegenerative mechanisms in the hippocampus at 4 h, 24 h and 7 day time points post-SE. We also performed electroencephalographic (EEG) analysis to determine the spike rate and SRS frequency.

Results

The behavioral studies revealed a significant reduction in the severity of the seizures and the time spent in convulsive motor seizures (CMS) stages in the fyn$^{-/-}$ mice and saracatinib treated mice when compared to the control groups during the 2 h established SE. The mortality rate in the fyn$^{-/-}$ mice was lower than the fyn$^{+/+}$ mice. The number of spontaneous electrographic non-convulsive seizures, the duration of CMS, and the spike frequency were also reduced in the fyn$^{-/-}$ mice. The epileptiform spike rate was higher in fyn$^{+/+}$ mice during the first 7 days, but they decreased thereafter. IHC analysis of brain sections revealed a significant increase in fyn, PKC-δ, oxidative and nitrative stress markers (gp91$^{phox}$, 4-HNE, 3NT) in the microglia in the dentate gyrus, CA3 and CA1 at 4 h and 24 h post-SE in fyn$^{+/+}$ mice. These levels were significantly reduced in the fyn$^{-/-}$ mice. We also observed a significant increase in the fyn and PKC-δ nuclear translocation in reactive microglia at 24 h post SE in the fyn$^{+/+}$ mice compared to the fyn$^{-/-}$ suggesting their role in the pro-inflammatory responses. Quantitative RT-PCR analysis revealed an increase in the TNF-α, IL-1β and iNOS mRNA levels in controls when compared with the fyn$^{-/-}$ mice. In the 24 h group, hippocampal Western blots revealed downregulation of fyn, PKC-δ, phospho Src-416, phospho PKCδ-507, gp91$^{phox}$, 4-HNE and caspase-3 levels in fyn$^{-/-}$ mice compared to fyn$^{+/+}$ mice. Moreover, a significant increase in the numbers of FJB-positive neurons were also observed in CA3 and CA1 regions of hippocampus at 24 h post-SE in fyn$^{+/+}$ mice compared to fyn$^{-/-}$.

CONCLUSIONS

Collectively, our data suggest that knocking out fyn gene or inhibiting its activity with a pharmacological inhibitor reduces the severity of SE. Fyn kinase absence, prevented neurodegeneration, perhaps by polarizing the microglia and by decreasing the expression of reactive oxygen and nitrogen species such as GP-91phox, 4-HNE and 3NT levels in the hippocampus. These findings suggest that fyn could be a potential therapeutic target for disease modification in epilepsy.

Example 2

The Fyn/SFK Inhibitor, Saracatinib, Significantly Reduced the Severity of SE and Prevented Mortality During SE Materials and Methods We used young adult (8 weeks) male C57BL/6J mice from Jackson laboratory (ME, USA), young adult male Sprague Dawley rats from Charles River (MA, USA) and fyn$^{+/+}$ and fyn$^{-/-}$ mice (8 weeks) for our experiments. The fyn$^{+/+}$ and fyn$^{-/-}$ mice were bred on C57BL/6J and Balb-c genetic background in Dr. Kanthasamy's animal breeding facility, Laboratory Animal Resources (LAR), Iowa State University (ISU). The fyn$^{+/+}$ mice were used as control for fyn$^{-/-}$ mice. The fyn$^{+/+}$ mice neither overexpress Fyn nor contain constitutively active Fyn. The fyn$^{-/-}$ mice were originally obtained from Dr. Dorit Ron's laboratory (by Dr. Kanthasamy) at the University of California, San Francisco, and are now available from the Jackson Laboratory (stock #002271). The fyn$^{-/-}$ mice were genotyped routinely by qRT-PCR to confirm fyn knockout. The fyn$^{-/-}$ mice used in this study had normal phenotype and no obvious differences were observed in their sexual and exploratory behaviors, body weight, brain structure (gross weight and histology) when compared to the wildtype control mice (fyn$^{+/+}$ mice). All animals were maintained at the LAR at ISU under controlled environmental conditions (19° C.-23° C., 12 h light: 12 h dark), with ad libitum access to food and water. Animals purchased from Jackson laboratory and Charles River were used for experiments after four days of quarantine. All experiments were carried out in accordance with Institutional Animal Care and Use Committee (IACUC), ISU, USA (protocol number 10-12-7446/8090-MR). All surgical procedures were carried out in sterile and aseptic conditions under gaseous isoflurane anesthesia. The pre- and post-operative care were given to all animals to minimize pain and discomfort during and after surgery. Animals were monitored and weighed daily after surgery till they were used in the experiments. At the end of each experiment, the animals were euthanized by intraperitoneal (i.p.) administration of 100 mg/kg pentobarbital sodium as per the recommendations of the American Veterinary Medical Association (AVMA) Guidelines for Euthanasia of Animals.

Kainate (Tocris) was prepared in sterile water at the concentration of 2 mg/mL. It was always prepared fresh prior to its use. Saracatinib was purchased from Selleck Chemicals, PA, USA, and was prepared fresh in 0.5% (w/v) hydroxypropyl methylcellulose (CMC) and 0.1% tween 80 (Sigma Aldrich, USA) at the concentration of 5 mg/mL. After CMC is evenly dispersed in sterile water at 90° C., the temperature of the solution was decreased by adding cold sterile water and stored at 20° C. to prevent it from precipitating at higher temperature.

For the LC-MS the optimum dose of saracatinib for our experiment was based on the published literature (Green et al., 2009; Hannon et al., 2010; Liu et al., 2012; Yang et al., 2010). However, to confirm whether it crossed the BBB and whether its levels persisted for a reasonable amount of time after the drug administration, we tested the brain concentrations of saracatinib at 8 h using liquid chromatography-mass spectrometry (LC-MS). The mice hippocampal tissues were homogenized in ~0.2 mL 1:1 methanol:water using bullet blender. An additional 125 μL HPLC grade water was added to the homogenized samples. This was followed by three similar successive extractions with 375 μL 3:1 acetonitrile:water. The homogenate was sonicated for 10 min in a sonication water bath. The sample was pelleted by centrifugation at 13,000 g for 7 min and the supernatant was collected after each extraction and the samples were pooled. The pooled supernatant was dried under a dry nitrogen gas stream. The dried sample was then re-suspended in 200 μL of 5% acetonitrile in water, filtered through a 0.2 m PTFE syringe filter, and then subjected to LC-MS analysis.

The LC-MS analysis for saracatinib was conducted using an Agilent Technologies 1290 Infinity Binary Pump UHPLC system coupled to an Agilent Technologies 6540 UHD Accurate-Mass Q-TOF mass spectrometer in high resolution mode (4 Gz) and scanning m/z 100-1700. LC separations were performed with Agilent Technologies Eclipse C18 1.8μ 2.1 mm×50 mm analytical column using an 18 min gradient from 100% buffer A (0.1% formic acid in HPLC grade water with 1% HPLC grade acetonitrile) to 100% buffer B (0.1% formic acid in HPLC grade acetonitrile with 1% HPLC grade water) followed by a 2 min hold in 100% buffer B and a 3 min equilibration in 100% buffer A. Saracatinib was detected as M+H$^+$ ions while using electrospray ionization in positive mode. Saracatinib detection is represented by extracted ion chromatogram (EIC) using a 10 ppm extraction window and was analyzed (FIG. 1E) using Agilent Mass Hunter Qualitative Analysis B.07.00 software. The X-axis on the EIC represents retention time and the Y-axis represents the abundance of ions detected. Saracatinib concentrations were observed as the area of the EIC peaks and was calculated based on the linear curve of the observed peak areas of standards. The standard concentrations ranged from 10 femtograms/mL to 1 micrograms/mL.

Thirty C57BL/6J mice were used for the saracatinib experiment. In this experiment, 15 mice were treated with saracatinib (25 mg/kg, oral gavage as a single dose) at 4 h prior to a single high dose (SHD) of kainate (25 mg/kg, i. p), while the remaining 15 mice were given the vehicle [0.5% hydroxypropyl methylcellulose in 0.1% tween 80] 4 h prior to kainate.

All animals administered with kainate were subjected to video recording. The seizures were staged and the SE was scored by direct observation of animals during the 2 h SE and exact duration of each stage of seizure was calculated. The video recordings were used for secondary analysis and for independent verification of seizures by two different personnel who were not involved in direct scoring during the experiments. The personnel who did the behavioral analysis were blind to the experimental groups. The behavioral seizures were scored based on modified Racine scale from stage 1 to 5 as described previously (Beamer et al., 2012; Puttachary et al., 2015b; Racine, 1972; Tse et al., 2014). Briefly, the staging was as follows: stage 1, absence-like immobility; stage-2, hunching with facial or manual automatisms evident from brisk movement of vibrissae and repeated grooming of the face; stage 3, rearing with forelimb clonus and facial or manual automatisms; stage 4, repeated rearing with continuous forelimb clonus and falling; and stage-5, generalized tonic clonic convulsions with lateral recumbence or jumping and/or wild running followed by generalized convulsions. Stage 1 and stage 2 were categorized as non-convulsive seizures (NCS) and stage ≥3 as convulsive seizures (CS) (Beamer et al., 2012; Puttachary et al., 2015b; Tse et al., 2014). The latency to the onset of CS and the duration of seizures were analyzed for each animal within a group as described previously (Puttachary et al., 2015b; Tse et al., 2014). The duration of CS is the total time spent by an animal in stage ≥3 during the 2 h of established SE until the diazepam was administered. Since a very few animals reached stage 5 in the saracatinib pretreated group and in the fyn$^{-/-}$ mice, we considered stage ≥3 as the starting point for 2 h established SE. The data were analyzed and the severity of seizures, duration of CS, latency to CS onset, and mortality rate were compared between the groups.

In all kainate-treated animals, the behavior seizures were terminated with diazepam (10 mg/kg, i.p.) at 2 h after the first onset of convulsive seizure. The 2 h duration between the onset of convulsive seizure and the diazepam treatment was considered as 2 h established SE. During this period, all wildtype control mice had continuous convulsive seizures for >30 min. All kainate-treated animals received 1 mL of Ringer's lactate solution (s.c.) twice a day for three days to enable them to recover from dehydration and the lost bodyweight due to SE.

Results

Figure 1B:
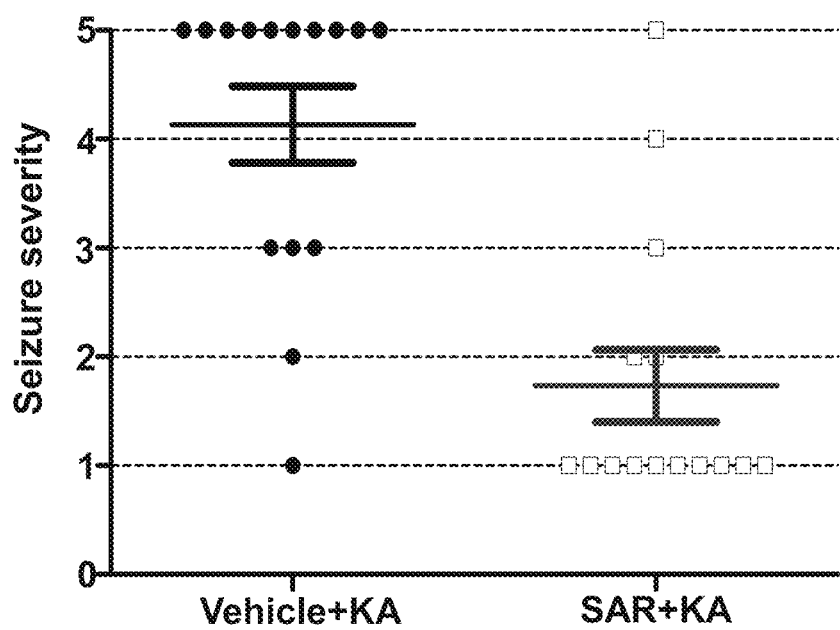
Figure 1C:
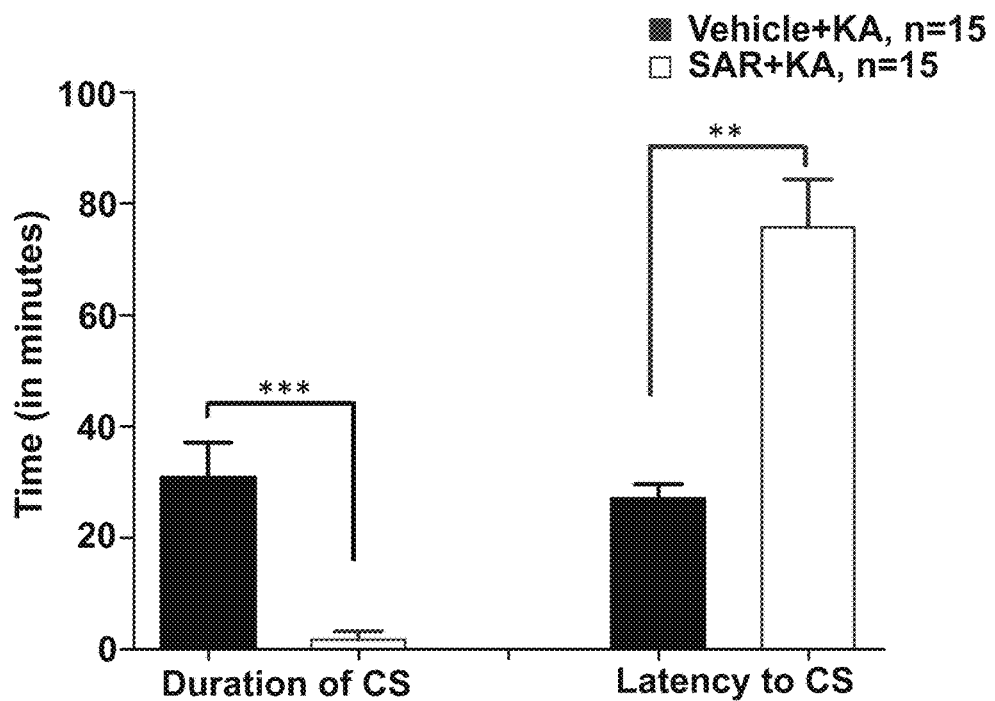
FIG. 1C show the SAR treated group showed a significant reduction in the duration of CS (*$p<0.0001$), and a very few mice reached stage ≥3 seizure after a prolonged period when compared with the vehicle treated group ($p<0.01$).
Figure 1D:
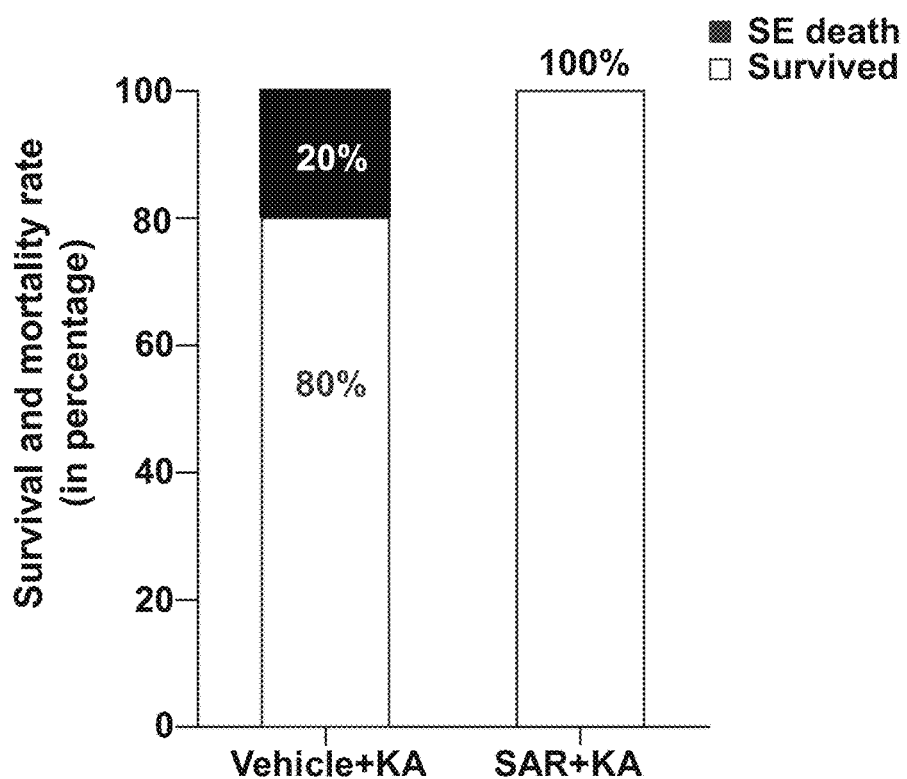
FIG. 1D shows the survival and mortality rate in SAR and the vehicle treated mice (Fisher's exact test).
Figure 1E:
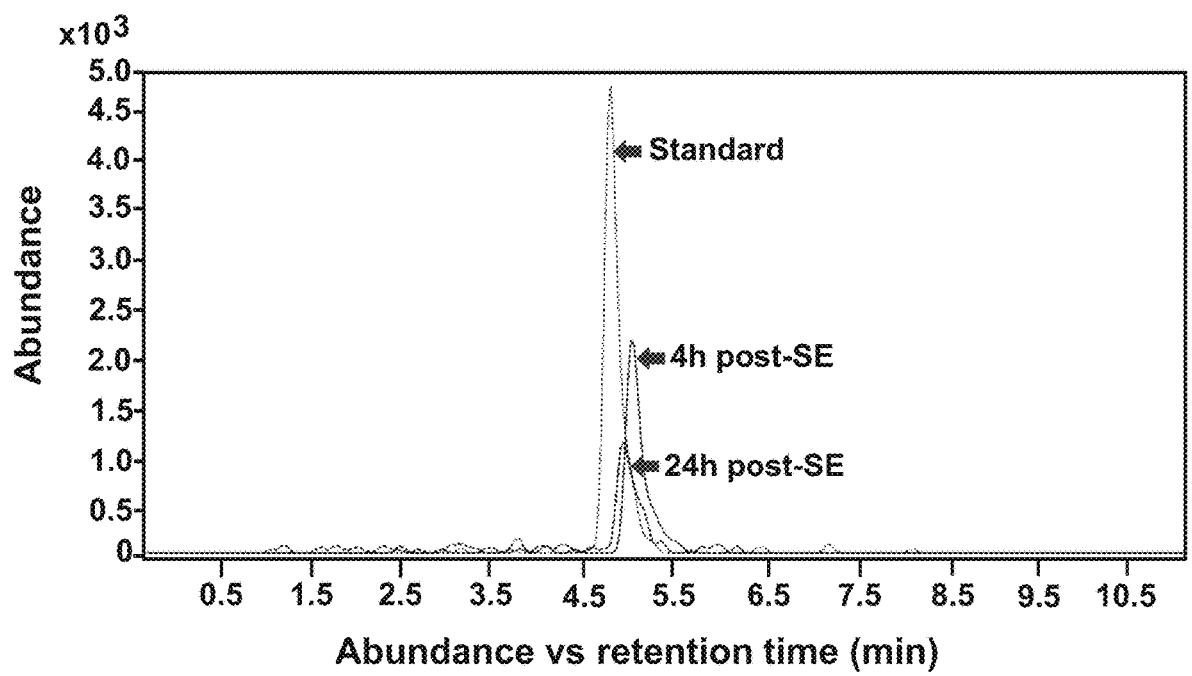
FIGS. 1E and 1F shows the ion chromatogram showing the relative abundance of the SAR in the hippocampus. The LC-MS analysis confirmed that the SAR crossed the BBB and the SAR was persisted in the hippocampus at higher levels at 8 h post-SE when compared to 28 h post-administration (***$p<0.001$). *$p<0.05$, $p<0.01$, *$p<0.001$; Mann-Whitney test for FIGS. 1B, 1C, and 1F.
Figure 1F:
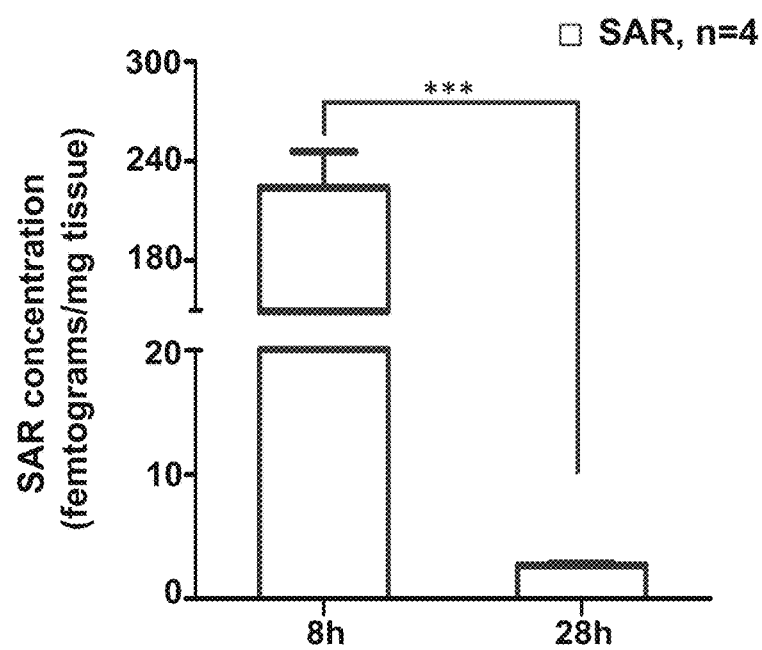

The saracatinib is a broad spectrum SFK inhibitor (Green et al., 2009; Hennequin et al., 2006), and is in the clinical trials for treating Alzheimer's disease (Nygaard et al., 2015). Since saracatinib also targets the hippocampus, an important ictogenic foci of the brain, we tested its impact on SE onset. Saracatinib (25 mg/kg) or the vehicle was administered orally as a single dose at 4 h prior to the induction of SE with kainate. The dose was selected based on the published literature (Green et al., 2009; Hennequin et al., 2006). We tested the effect of a SHD of kainate (25 mg/kg) on behavioral seizures onset, and compared the seizure severity, duration of convulsive seizures, latency, and survival rate between the groups. The studies revealed a significant reduction in seizure severity and the duration of CS, and increased latency to the onset of first CS in the saracatinib treated mice when compared to the vehicle control group during the 2 h established SE (FIGS. 1A to 1C). There was no mortality in the saracatinib treated group due to a significant reduction in the severity of seizures. As expected, about 20% mortality occurred in the vehicle-treated control group due to severity of kainate-induced seizures (FIG. 1D). In the SHD of kainate group, 67% of the mice reached stage 5 seizure in the vehicle group, while only 7% reached stage 5 and they spent less time in CS stages in the saracatinib group (FIG. 1B) suggesting the role of Fyn and other SFK in seizure modulation. LC-MS analysis of the hippocampi confirmed that the saracatinib crossed the BBB and it persisted at high levels at 8 h (223.8±22.01), and were also detected at 28 h post administration (2.693±0.1714) ($r^2$=0.9665; ***p<0.0001) (FIGS. 1E and 1F).

Example 3

Fyn Knockout Reduced SE Severity, Mortality, Epileptiform Spikes, and Spontaneous NCS and CS During the First 4 Weeks of Post-SE Materials and Methods The same lines of mice as used in Example 2 were also used for this example. Saracatinib and vehicle was also prepared in the same way as in Example 2. Diazepam was also administered as in Example 2. SE qualification is was also performed as in Example 2.

Twenty mice (n=10 each of fyn$^{+/+}$ and fyn$^{-/-}$ mice) were tested for effectiveness of SHD method of kainate (25 mg/kg, i.p) administration to induce SE. We observed 80% mortality in the fyn$^{+/+}$ and 40% in the fyn$^{-/-}$ mice with SHD of kainate, therefore for the rest of the experiments we followed a repeated low dose (RLD) method of SE induction with kainate (5 mg/kg, i.p., given at 30 min intervals until they showed convulsive seizures) as described previously (Puttachary et al., 2015b; Tse et al., 2014).

Twelve mice (n=6 each, fyn$^{+/+}$ and fyn$^{-/-}$) were used for video-EEG telemetry experiments. In this group, SE was induced 10 days after the transmitter implant after they animals recovered bodyweight. During the 10 day period of post-surgery, the baseline EEG was recorded continuously to cover both day and night cycles. The EEG recording during this period was used to evaluate the impact of surgery on spontaneous epileptiform spiking activity or seizures. The telemetry devise has a built-in temperature monitoring module which gives information about their body temperature and its impact on EEG outcome.

The fyn$^{+/+}$ and fyn$^{-/-}$ mice (n=6 each) were implanted with the ETA-F20 (for mice) PhysioTel™ telemetry device (Data Science International, Minneapolis, USA) for video-EEG recording. The animals received analgesic buprenorphine (0.3 mg/kg, s.c.) prior to surgery. The animals were anesthetized with gaseous isoflurane and the mid-dorsal aspect of the head and neck was shaved and chlorhexidine scrub followed by 70% ethanol were applied using a Q-tip. The eyes were lubricated with artificial tears ointment during surgery. The surgery was performed under sterile condition while the animal was placed on a heating mat. A mid-dorsal incision was made on the head extending from just above the mid-point of the eyes to the middle of the neck. The connective tissue was separated between the skin and muscles and a subcutaneous pocket was created along the spine and flank region, which was irrigated with sterile saline before the transmitter was inserted subcutaneously. The frontalis muscle was scraped off from the bone and bilateral burr holes were drilled (2.5 mm caudal to the bregma and 2 mm lateral to the midline) without damaging the dura matter. Insulation from the tips of the electrode wires was removed, and the exposed electrodes were bent into a "V" shape and inserted into the holes to rest on the surface of the dura matter over each cerebral hemisphere. The wires were secured in place with dental cement (mixed with methyl methacrylate liquid compound, A-M systems, WA, USA), and the exposed electrodes were completely covered with dental cement to avoid them contacting the surrounding tissues. The incision was closed with sterile surgical clips. The triple antibiotic ointment, Vetropolycin, was applied, antibiotic Baytril (Bayer pharma, PA, 5 mg/kg, s.c.) and 1 mL of dextrose normal saline were administered subcutaneously after the procedure. The nails were trimmed to prevent skin laceration and removal of clips. The telemetry device implanted animals were individually caged and placed on the PhysiolTel receivers RPC-1 connected to the data exchange matrix (specific to Dataquest A.R.T. system). The receivers detect previously matched transmitters and transmit information such as video-integrated EEG, body temperature, and activity counts from the receiver pads to the matrix and finally to the PC.

About 10 days of baseline EEG was recorded from each animal, prior to kainate treatment, which was used to normalize the EEG from post-SE period and to detect spontaneous spiking activity after surgery. The artifacts (electrical noise, exploratory behavior, grooming) were identified and excluded from epileptiform spike rate analysis. The epileptiform spikes were distinguished from artifacts based on the amplitude, duration of spikes and inter spike interval, as described in our previous publications on the mouse and rat models (Puttachary et al., 2015b and 2016b; Tse et al., 2014). After filtering the artifacts, the raw EEG was divided into 10s epochs for fast-fourier transformation (FFT) to generate power bands. The epileptiform spikes that we quantified included the spikes from the spike trains and the NCS. The spike train consisted of both spike clusters and individual epileptiform spikes including isolated pre-ictal and inter-ictal spikes. The spike clusters (<12s) included the epileptiform spikes of various amplitudes above the baseline. The electrographic NCS (>12s), associated with increased theta and delta power were quantified separately and compared between the groups. The spontaneous NCS and CS were identified and verified against real-time video and power spectrum and quantified as described in our previous publications (Puttachary et al., 2015b and 2016b; Tse et al., 2014). The identified seizures were subjected to a secondary validation by two independent observers. The number of seizure episodes and the spike rate were quantified using NeuroScore 3.2.0 software and were expressed as standard error mean (SEM) values.

Results

Figure 2A:
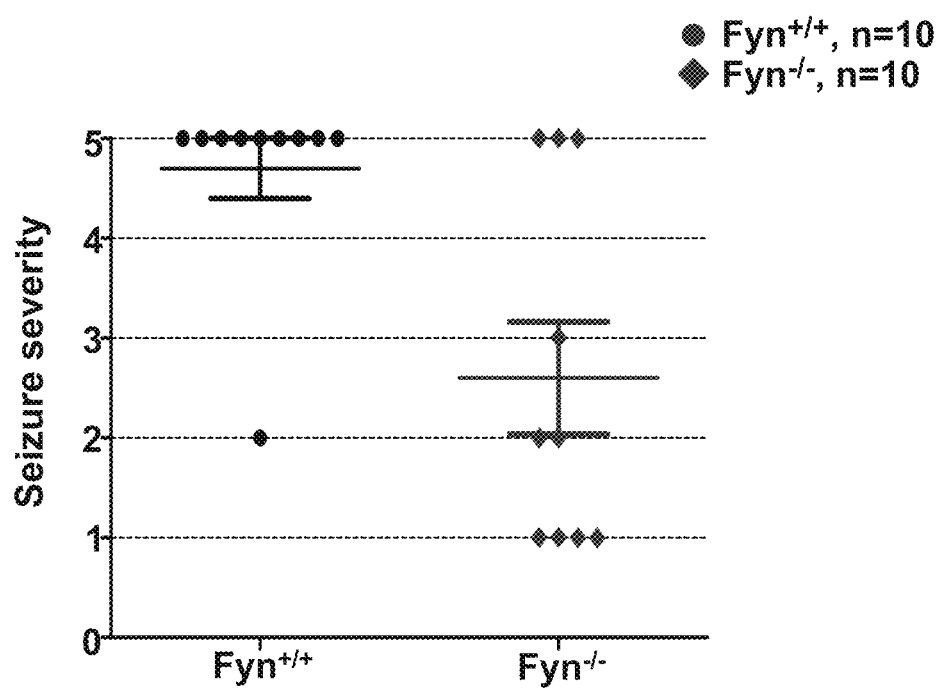
FIG. 2 is a graphical representation of a comparison of seizure severity and its duration, and mortality rate in fyn$^{+/+}$ and fyn$^{-/-}$ mice in single high dose (SHD, FIGS. 2A-2C) and repeated low dose (RLD, FIGS. 2D-2H) of kainite treatments. Each dot in FIG. 2A represents individual animal. The fyn$^{-/-}$ mice showed a significant reduction in seizure severity compared to the fyn$^{+/+}$ mice (**$p<0.01$, Mann-Whitney, n=10 for each group).
FIG. 2B shows the survival and mortality rate in fyn$^{+/-}$ and fyn$^{-/-}$ mice (*$p<0.05$, Fisher's exact test). Of the total 40% mortality, about 20% was observed after the diazepam treatment in the fyn$^{-/-}$ mice.
FIG. 2C shows the latency to convulsive seizures (CS) onset, following a single high dose (SHD) of kainate, was significantly increased in fyn$^{-/-}$ when compared to fyn$^{+/+}$ mice (*$p<0.05$, Mann-Whitney).
FIG. 2D shows the comparison of the time course of behavioral SE between the groups during 2 h established SE after mice reached first stage ≥3 seizure (*$p<0.0001$, two-way ANOVA between 1 and 2072 degrees of freedom, F=839.67, n=36 for each group).
In FIG. 2E, each dot represents individual animal (*$p<0.0001$, Mann-Whitney). In Figures F-H the fyn$^{-/-}$ mice showed a significant reduction in the duration of CS (F, ***$p<0.001$, Mann-Whitney), and there was no significant difference in the latency to the onset of CS. In fyn$^{-/-}$ mice, 22% mortality was observed (8% during the SE and 14% post-diazepam), while in the fyn$^{+/+}$ mice 10% of the mice died during the SE, but none died after the diazepam treatment (G, not significant, Fisher's exact test).
FIG. 2H shows there were no significant differences in the average numbers of RLD of kainate injections (5 mg/kg per injection at 30 min intervals) given to the fyn$^{+/+}$ and fyn$^{-/-}$ mice to achieve stage ≥3 seizure.
Figure 2B:
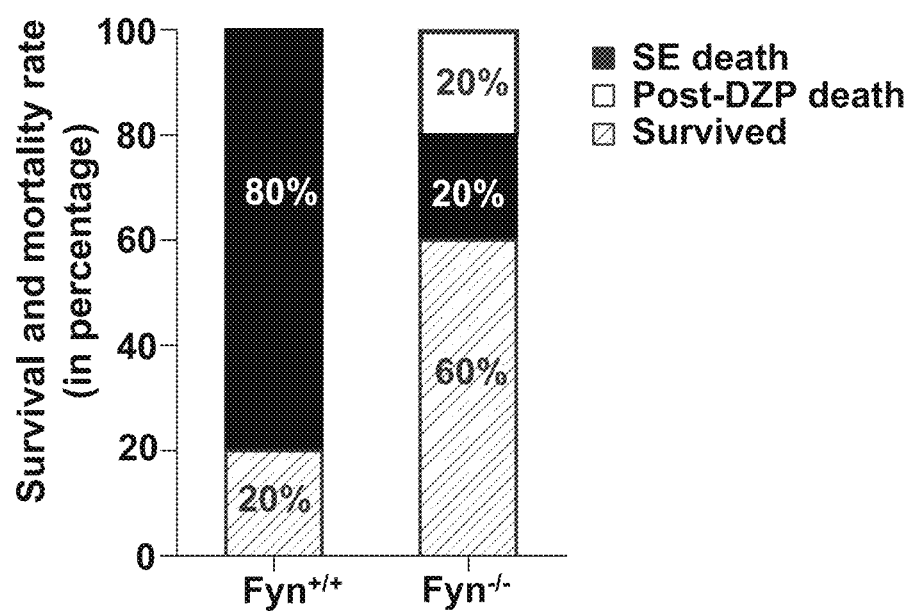
Figure 2C:
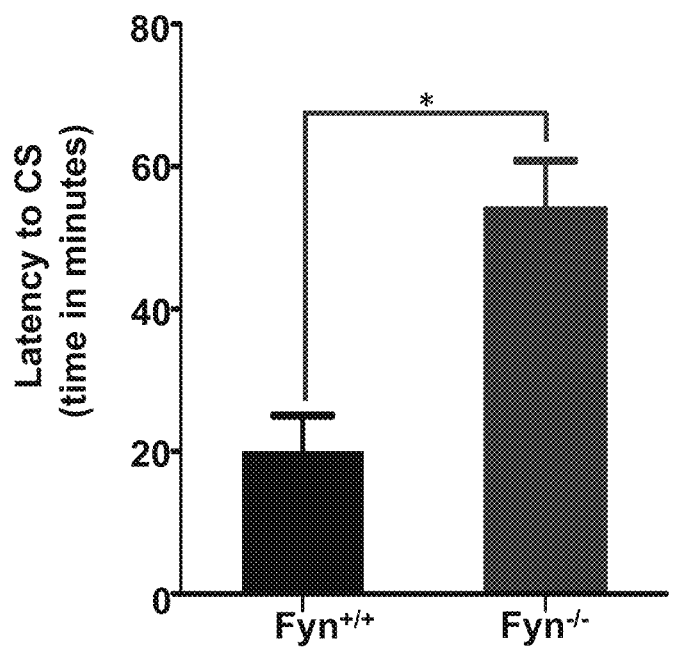

Having observed a significant reduction in SE severity with saracatinib treatment, we tested further whether Fyn kinase has a role in the mechanism of seizure onset. We used fyn$^{-/-}$ and the wildtype control mice for SE induction. First, we used a SHD of kainate (25 mg/kg) for both fyn$^{-/-}$ and fyn$^{+/+}$ mice. Interestingly, unlike the vast majority of C57BL/6J mice, the fyn$^{+/+}$ hybrid mice did not show a progressive seizure pattern from stage 1 to 5, instead the majority of them (90%) directly reached stage 5 seizures in <20 min of kainate administration, and 80% of them died during SE (FIGS. 2A and 2B). In contrast, fyn$^{-/-}$ mice showed fewer episodes of stage 5 seizures in 30% of the mice, but mortality rate was 40% (FIG. 2B) even after diazepam administration. Animals that had severe SE, during the 2 h of established SE, excessive salivation was observed more frequently in fyn$^{+/+}$ mice than in fyn$^{-/-}$ mice. Another interesting observation was their sensitivity to diazepam treatment. Both fyn$^{+/+}$ and fyn$^{-/-}$ mice took longer time to recover from diazepam treatment (almost 12 h) compared to C57BL/6J mice with the same dose (10 mg/kg) and they recovered in <3 h after diazepam treatment.

Figure 2D:
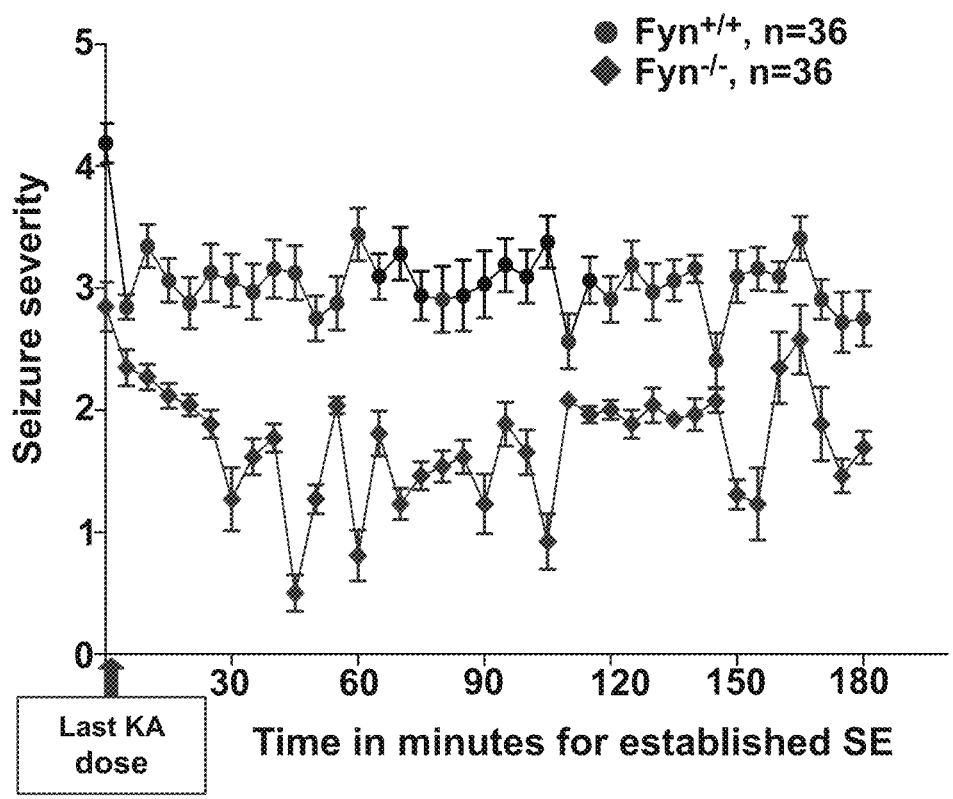
Figure 2E:
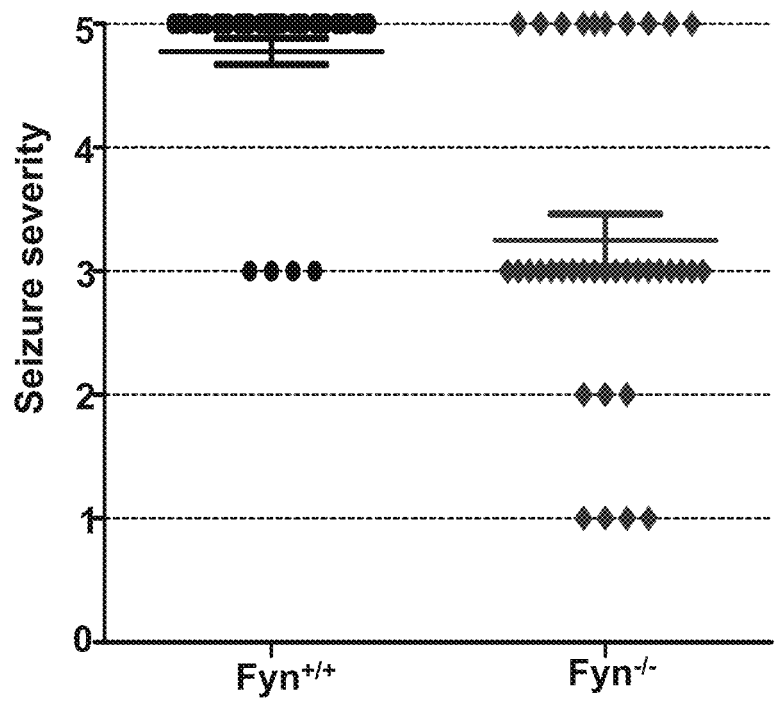
Figure 2F:
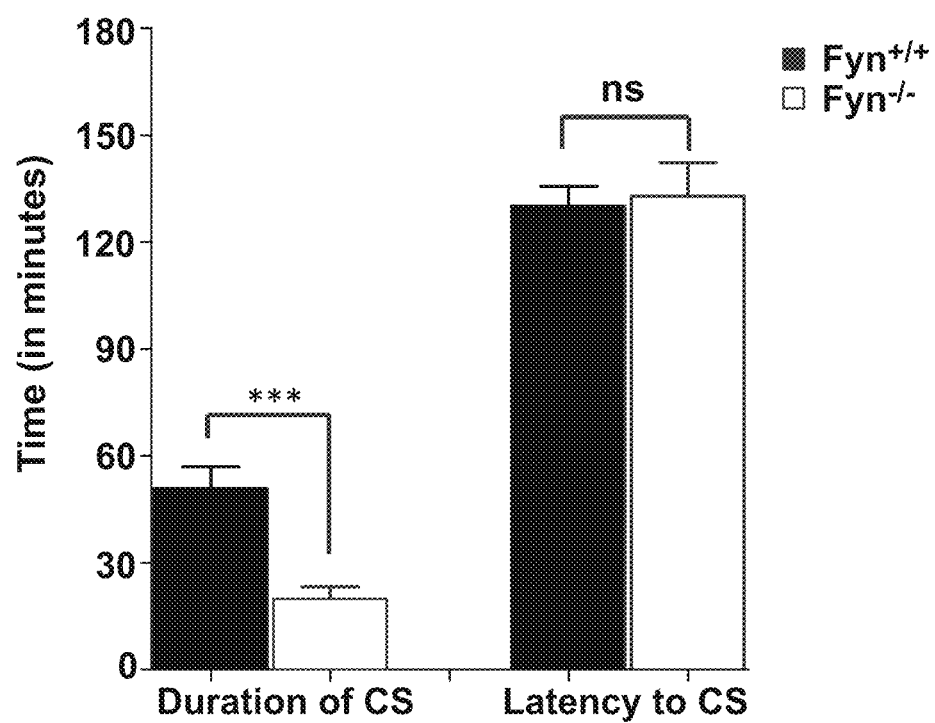
Figure 2G:
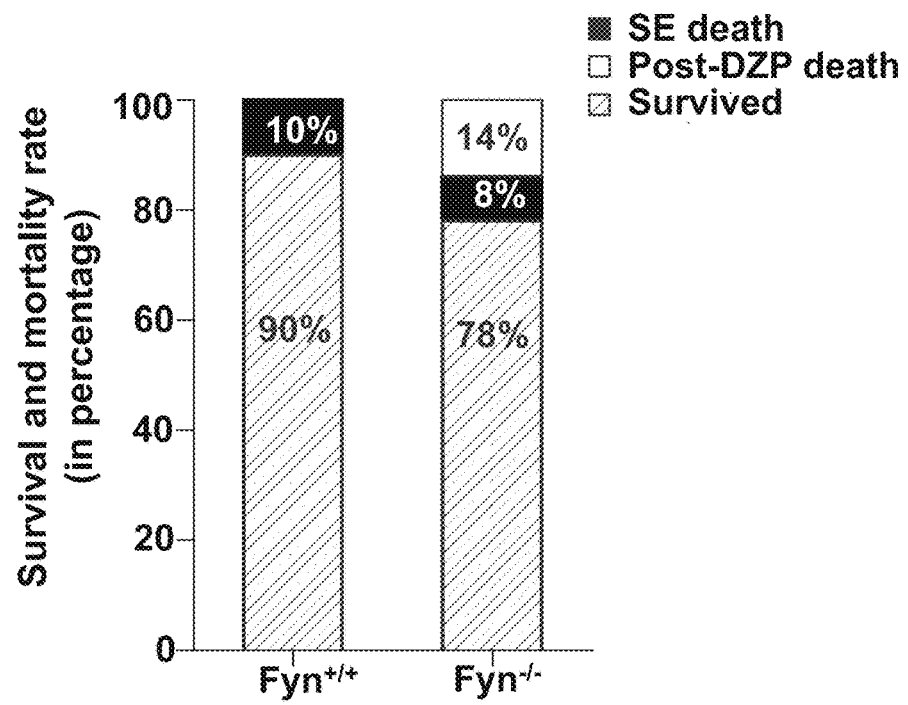
Figure 2H:
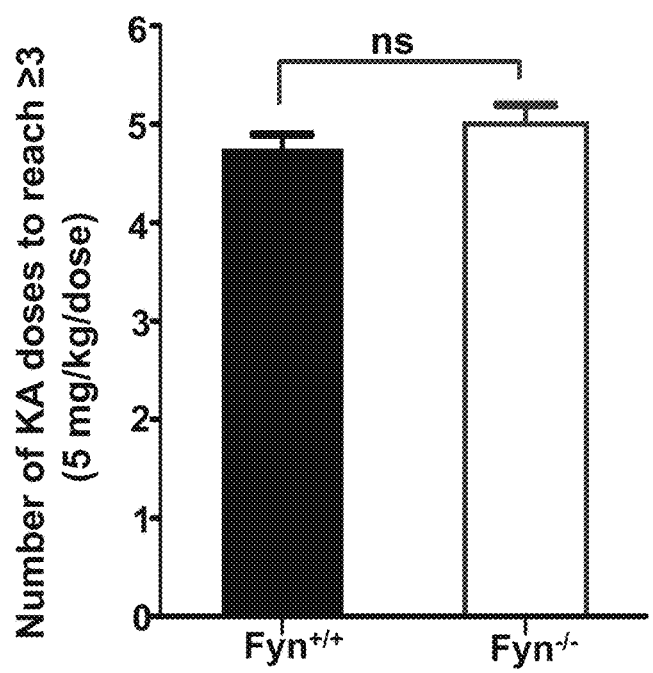

Since there was increased mortality rate in both fyn$^{+/+}$ and fyn$^{-/-}$ mice with SHD of kainate, we used RLD of kainate method to reduce mortality and to understand seizure progression during SE. We pooled the SE behavioral data from all time-points in non-telemetric groups and compared between the fyn$^{+/+}$ and fyn$^{-/-}$ mice. Both groups received similar numbers of RLD of kainate, therefore there was no significant difference in the total amount of kainate administered between the groups to reach convulsive seizures (FIG. 2H). Also, there was no significant difference between the groups in latency to the first onset of convulsive seizure (FIG. 2F), but there was a significant reduction in the seizure severity (FIGS. 2D and 2E). Interestingly, the mortality rate in fyn$^{-/-}$ mice was higher than fyn$^{+/+}$ mice (22% vs. 10%; FIG. 2G) with the RLD method of SE induction with kainate, which was unexpected. Out of 22% mortality in the fyn$^{-/-}$, 14% was after diazepam treatment.

Figure 3C:
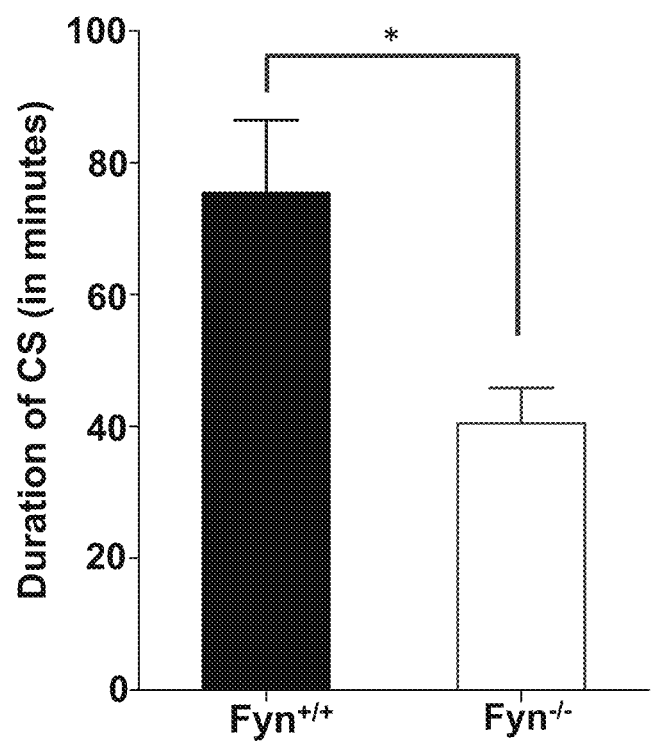
FIG. 3C shows the duration of CS for EEG seizures (stage ≥3) during the 2 h established SE was significantly lower in the fyn$^{-/-}$ mice when compared to the fyn$^{+/+}$ mice (*$p<0.05$, Mann-Whitney test, n=6 for each group).
Figure 3D:
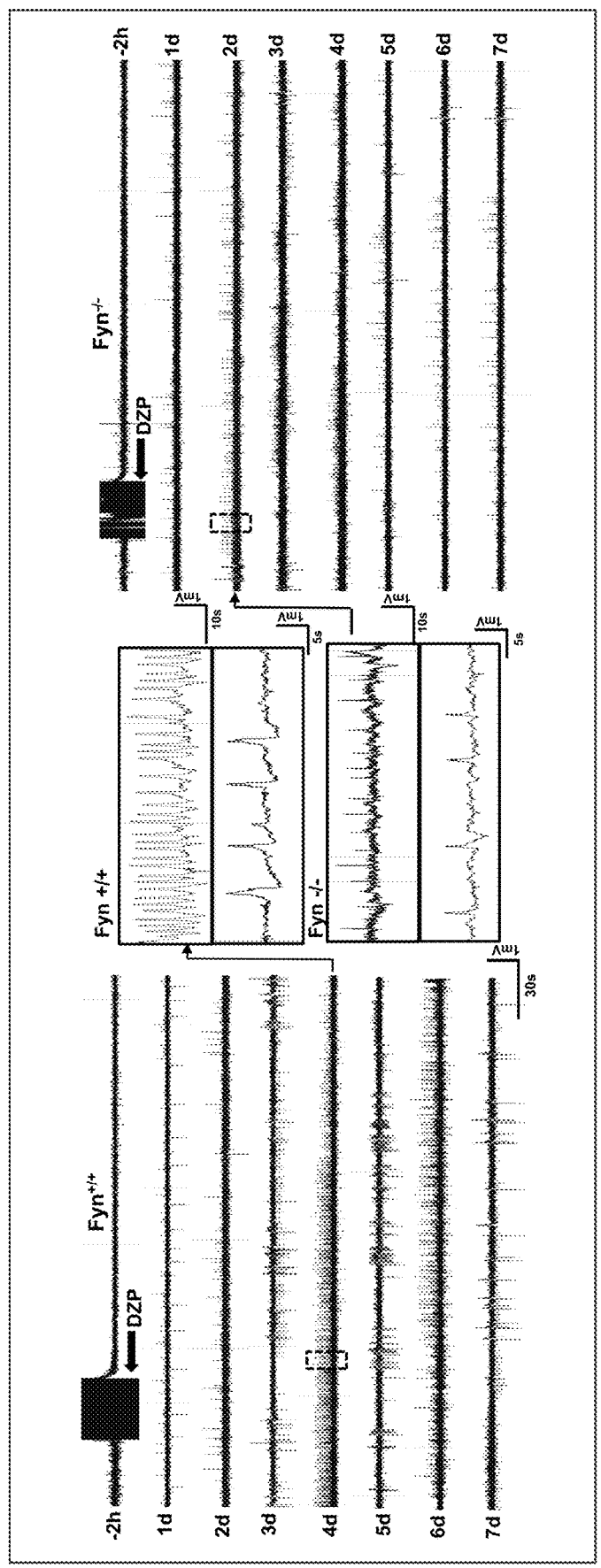
FIGS. 3D and 3E show representative EEG traces and epileptiform spikes during the first 7d post-SE (FIG. 3D), and a typical spontaneous NCS episode with associated power bands (FIG. 3E).
Figure 3E:
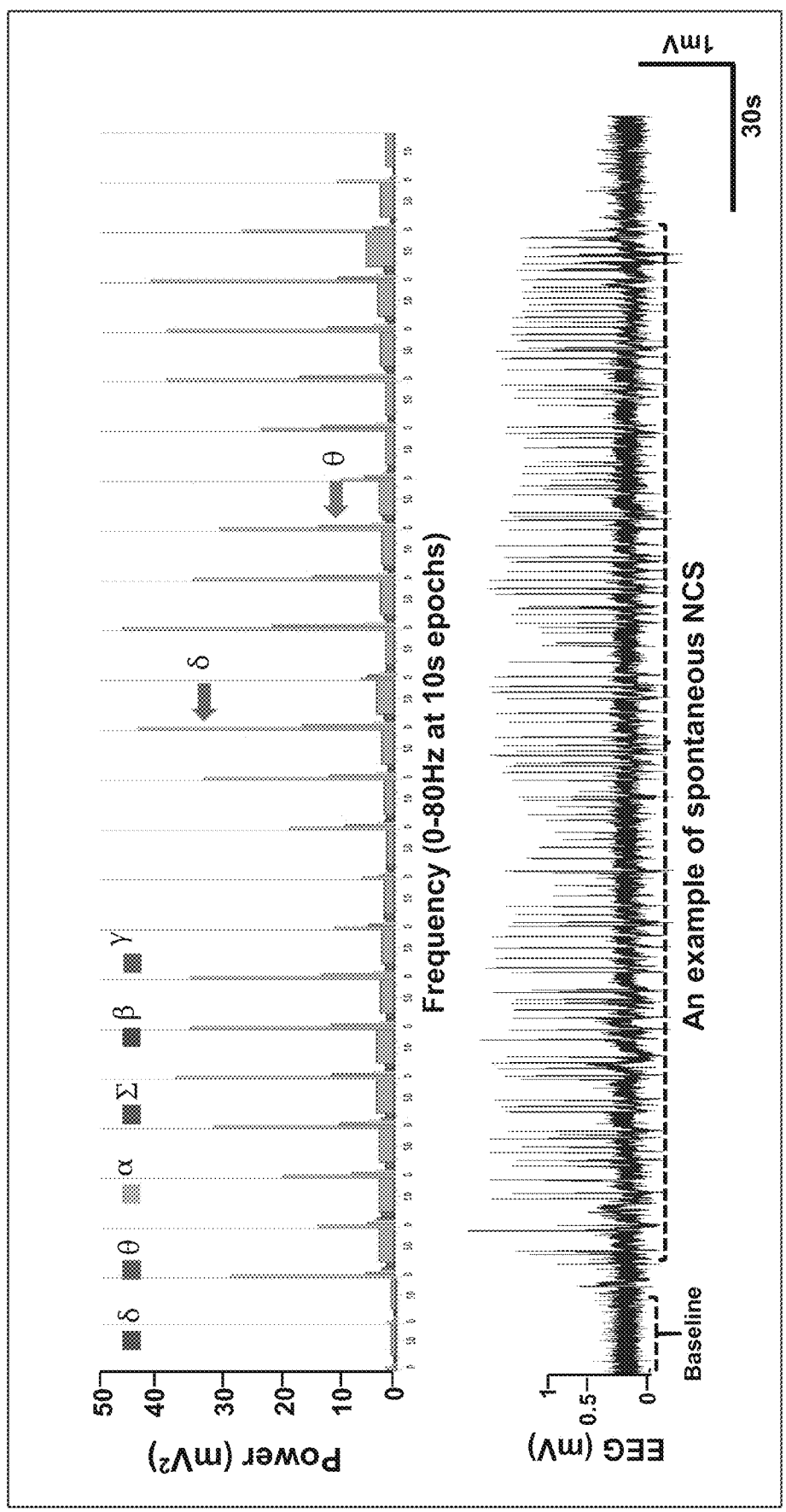
Figure 3F:
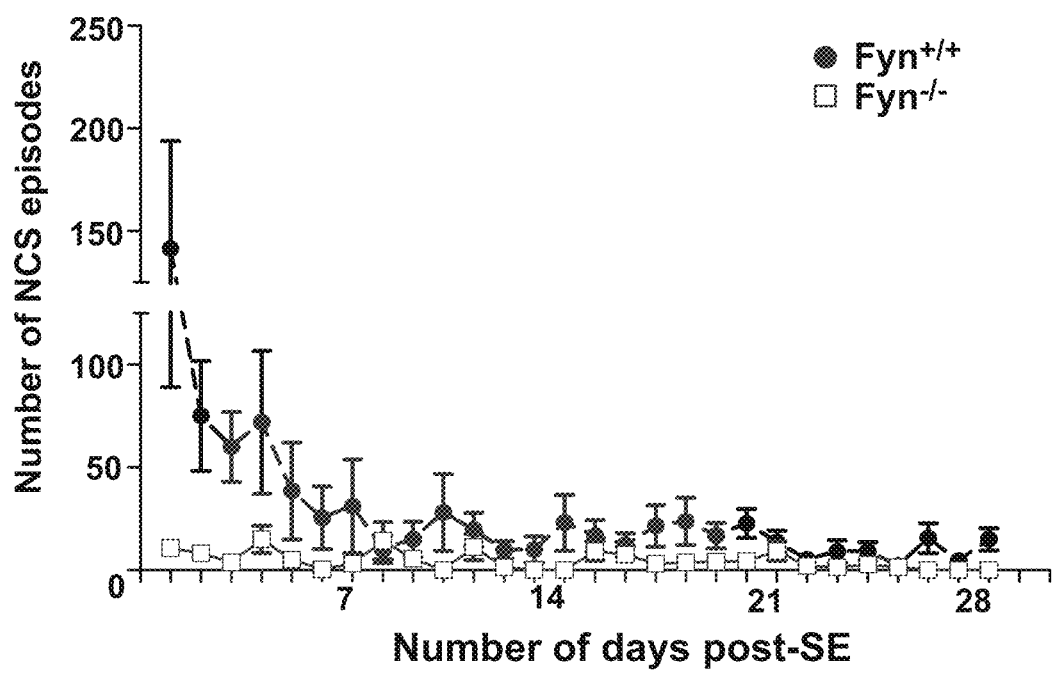
FIGS. 3F and 3G show the comparison of NCS frequencies between the fyn$^{-/-}$ and fyn$^{+/+}$ mice during 28d post-SE (F, *$p<0.0001$, two-way ANOVA between 1 and 140 degrees of freedom, F=35.17, n=6 per group; G, $p=0.0016$, *$p<0.001$, Mann-Whitney).
Figure 3G:
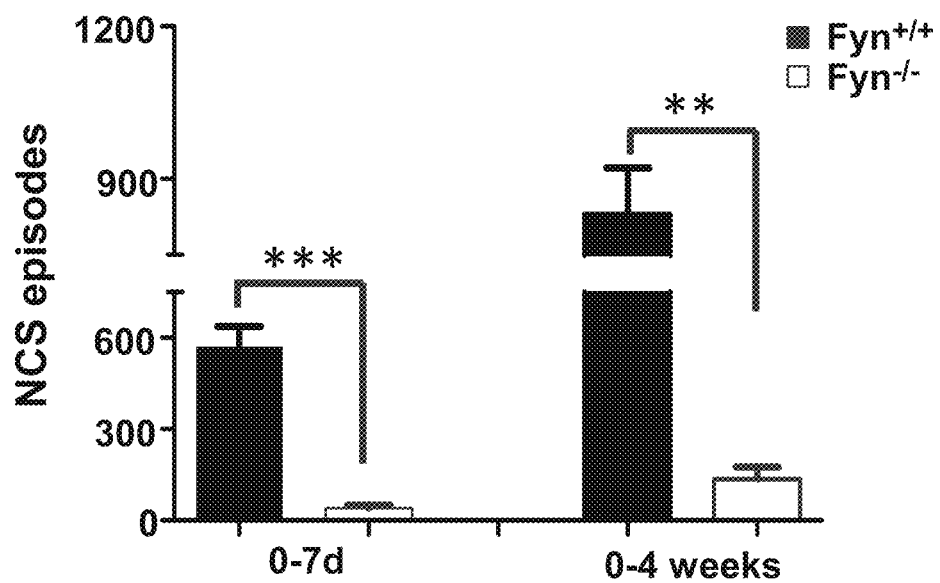
Figure 3H:
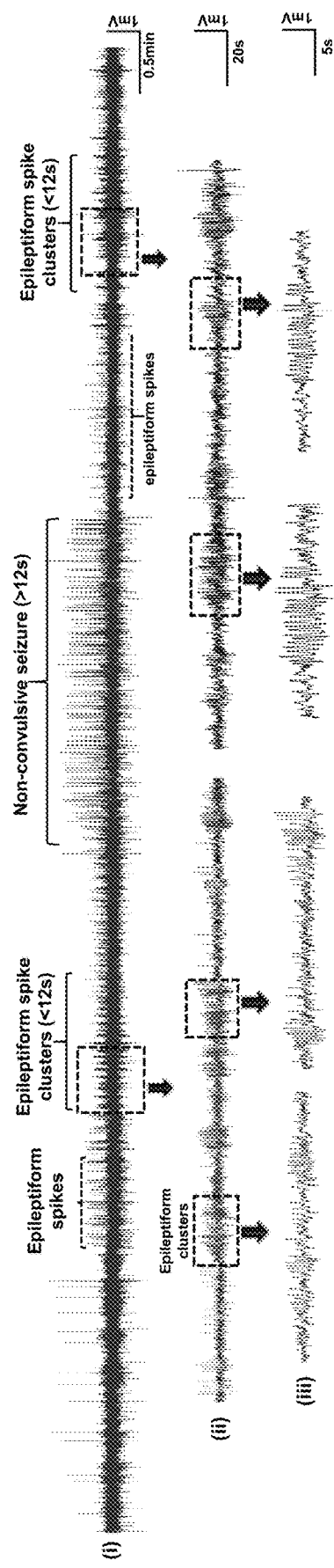
FIG. 3H shows an example of spike trains with spike clusters (<12s), a typical NCS episode (>12 sec), and isolated epileptiform spikes.
Figure 3I:
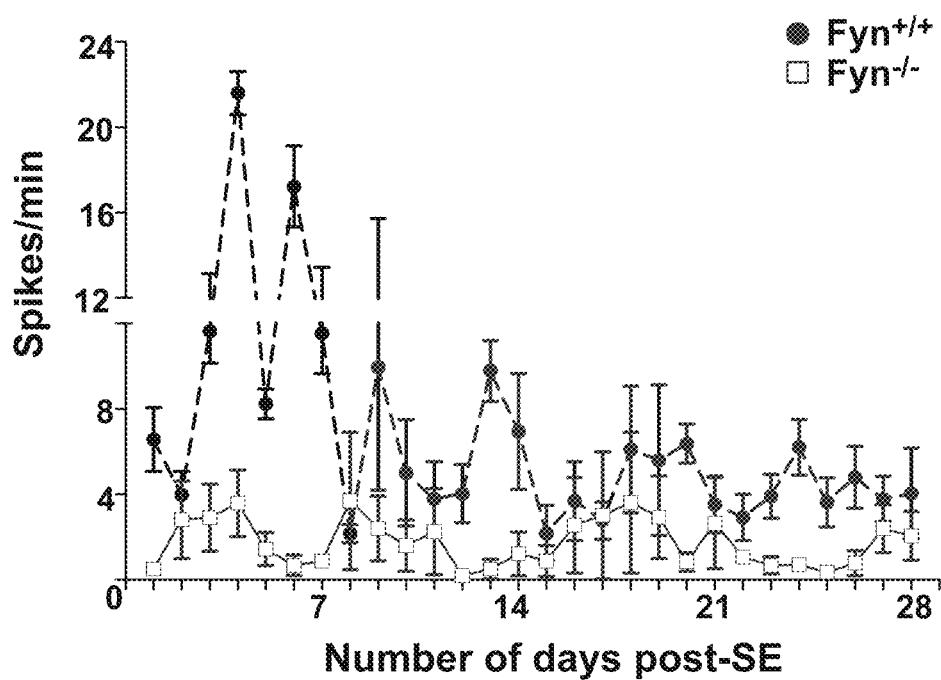
FIGS. 3I and 3J show the comparison of epileptiform frequencies between the fyn$^{-/-}$ and fyn$^{+/+}$ mice during 28d post-SE.
Figure 3J:
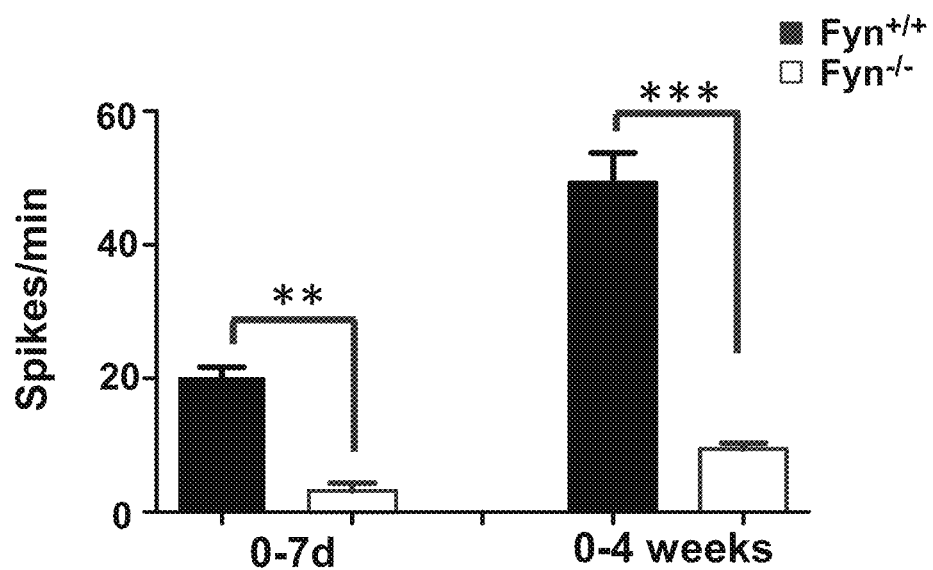

The telemetry implanted mice were subjected to continuous (24/7) video-EEG monitoring to quantify epileptiform spikes and spontaneous seizures frequency during the first four weeks of post-SE. Prior to kainate administration, none of the mice showed epileptiform spike or seizure during the first 10d post-surgery. A representative EEG traces during the SE (FIG. 3A) and post-SE between fyn$^{+/+}$ and fyn$^{-/-}$ mice (FIG. 3D) are shown. Increased delta and theta powers, and decreased gamma power were correlated with the epileptiform spike characteristics on EEG in NCS (FIG. 3E). During the SE, there was about 50% reduction in the duration of CS in the fyn$^{-/-}$ mice when compared to the fyn$^{+/+}$ mice (FIG. 3C). Unlike the C57BL/6J mice reported in our publication (Puttachary et al., 2015b), the number of spontaneous CS were very few (average 5 episodes) in the fyn$^{+/+}$ and spontaneous CS were completely absent in the fyn mice. Therefore, we quantified electrographic NCS and the epileptiform spike frequency in both groups as described previously in our publication (Puttachary et al., 2015b). We considered spike trains and the epileptiform spikes within seizure clusters (<12s duration) to determine the epileptiform spike frequency. An example of an electrographic NCS, the spike train, and spike clusters is illustrated (FIG. 3H). During the 28d post-SE, both spontaneous electrographic NCS and the epileptiform spikes frequencies were significantly reduced in fyn$^{-/-}$ when compared to fyn$^{+/+}$ mice (FIGS. 3F, 3G, 3I, and 3J).

Example 4

SE Significantly Increased Both Fyn and Phosphorylated Src Kinase Levels in the Hippocampus of fyn$^{+/+}$ Mice, but not in Fyn$^{-/-}$ Mice
Materials and Methods The same lines of mice as used in Example 2 were also used for this example. Saracatinib and vehicle was also prepared in the same way as in Example 2. Diazepam was also administered as in Example 2. SE quantification was also performed as in Example 2.

The primary antibodies used in the study and their concentrations are as follows: Fyn (mouse monoclonal, 1:300 for immunohistochemistry (IHC) and 1:800 for Western blot (WB), PKCδ (rabbit polyclonal, 1:300 for IHC 1:1000 for WB), pPKCδ-507 (goat polyclonal, 1:1000 for WB) and lamin-B (goat polyclonal; 1:500 for WB) were all purchased from Santa Cruz, Calif., USA; pSrc-416 (rabbit polyclonal; 1:1000 for WB) and caspase-3 and cleaved caspase-3 (rabbit polyclonal, 1:1000 for WB) were purchased from Cell Signaling, MA, USA; 4-HNE (rabbit polyclonal, 1:300 for IHC and 1:1000 for WB), gp91$^{phox}$ (rabbit polyclonal, 1:400 for IHC and 1:1000 for WB); 3-NT (mouse monoclonal, 1:1400 for WB), IBA1 (goat polyclonal, 1:500 for IHC) and β-actin (rabbit polyclonal, 1:10,000 for WB) were purchased from Abcam, Mass., USA; NeuN (rabbit polyclonal, 1:400 for IHC, EMD Millipore, USA); Fluoro-Jade B was purchased from Histochem Inc., Jefferson, Ark., USA. The secondary antibodies used for IHC were tagged with either a fluorescent dye (CY3 conjugated 1:200 or FITC conjugated 1:80) or biotin (1:500). They were purchased from Jackson ImmunoResearch laboratories, PA, USA. All the primary and secondary antibodies were prepared in 2.5% donkey (neutral species) serum to prevent cross reactivity, 0.25% sodium azide and 0.1% triton in 0.1M PBS. Streptavidin conjugates (reacts with Biotin-SP-conjugated antibodies and Biotin-SP-conjugated ChromePure proteins) were diluted in PBS alone. For WB, IRDye 680LT and 800CW donkey anti-goat or anti-mouse or anti-rabbit secondary antibodies were used at the dilution of 1:10,000. They were purchased from LI-COR Biosciences, NE, USA.

Eighty-eight animals (n=12 each from fyn$^{+/+}$ and fyn$^{-/-}$ per time-point for kainate, and 8 animals each from fyn$^{+/+}$ and fyn$^{-/-}$ without kainate served as naïve control for all time-points) were administered with a RLD of kainate and euthanized at 4 h, 24 h, and 7d time-points.

Animals were euthanized at 4 h, 24 h and 7d post-SE. The brains were isolated and processed for IHC, WB, and qRT-PCR studies. The serum samples were used for cytokine assay. Serum was collected using the standard 'serum preparation protocol' from ThermoFischer Scientific. All animals were euthanized with an overdose of pentobarbital sodium (100 mg/kg, i.p.).

Figure 4A:
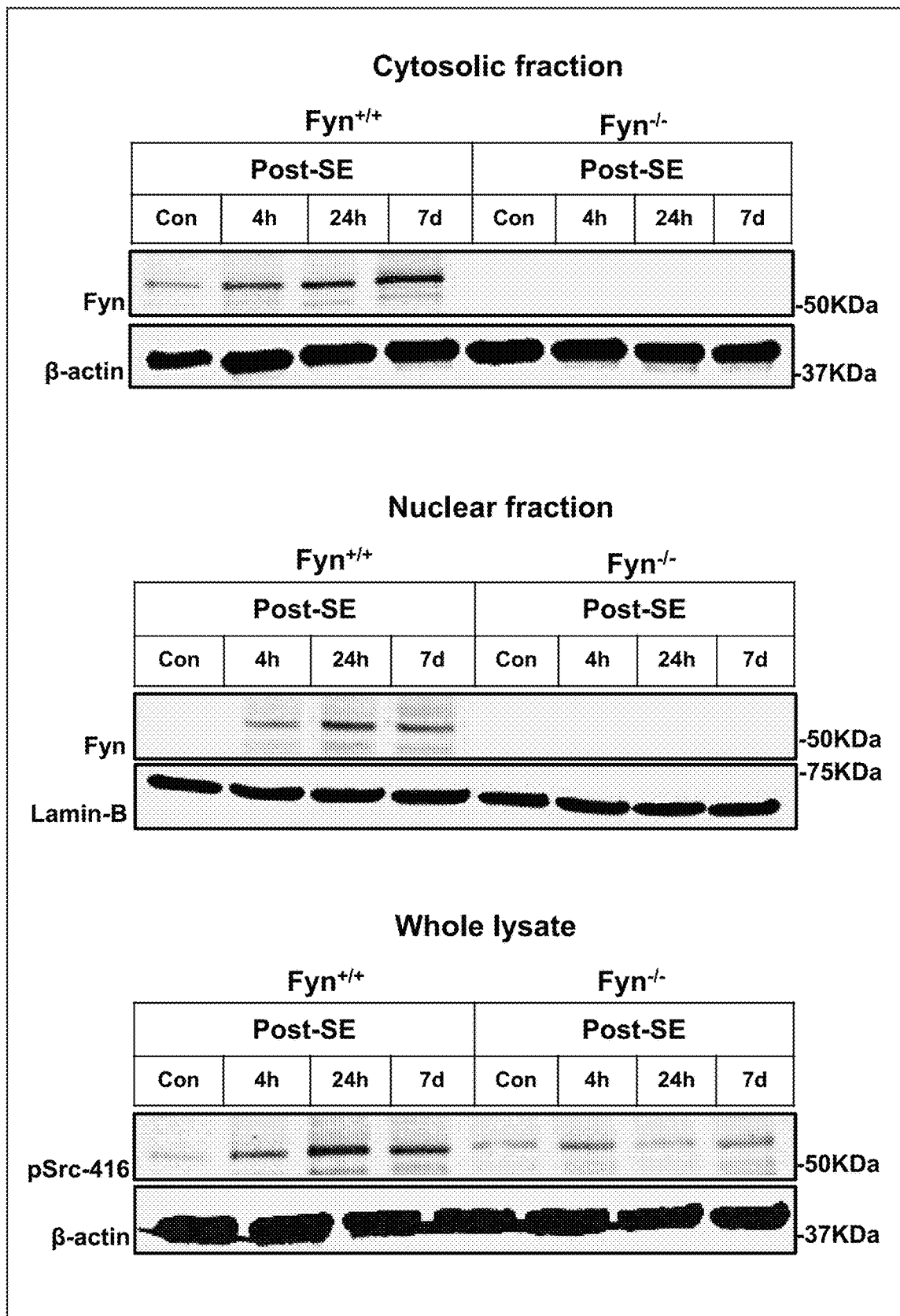
FIGS. 4A-4D show Western blot analysis of Fyn and pSrc-416 at 4 h, 24 h, and 7d post-SE. The cytosolic and nuclear Fyn proteins were absent in the fyn$^{-/-}$ mice, while they were significantly increased at 24 h and 7d post-SE in fyn$^{+/+}$ mice when compared to the naïve control. The pSrc-416 levels also increased significantly in the fyn$^{+/+}$ mice at all time points, but no significant differences were observed in the pSrc-416 levels in the fyn$^{-/-}$ compared to the control (FIG. 4D). However, when compared between the groups, it was reduced in the fyn$^{-/-}$ mice at 24 h and 7d post-SE (D) *$p<0.05$, $p<0.01$, *$p<0.001$; n=5-6.
Figure 4B:
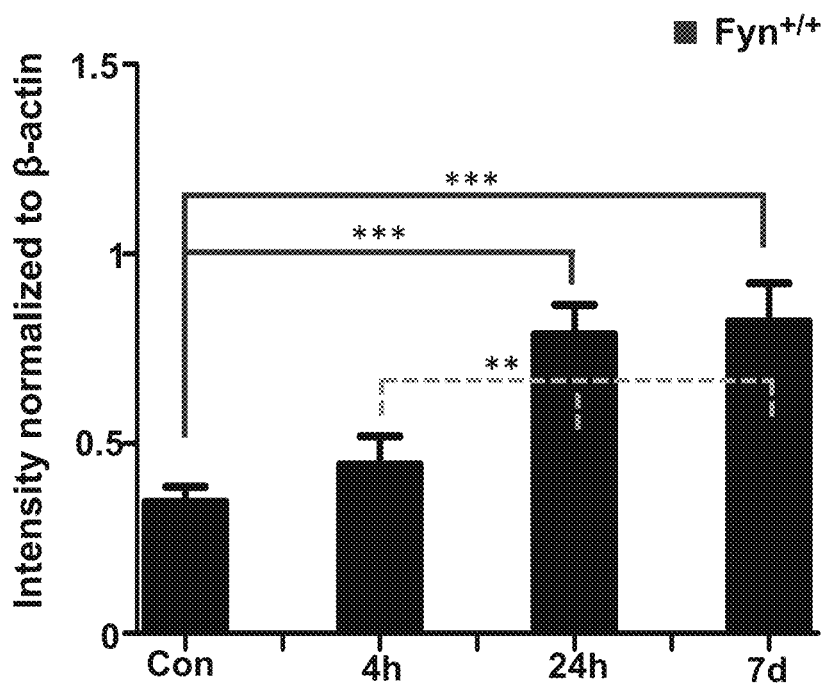
Figure 4C:
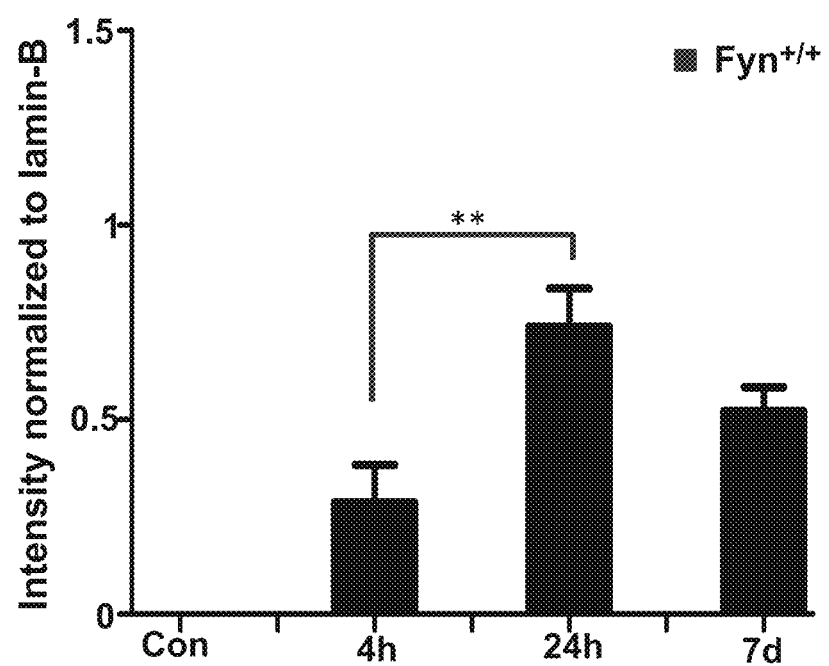
Figure 4D:
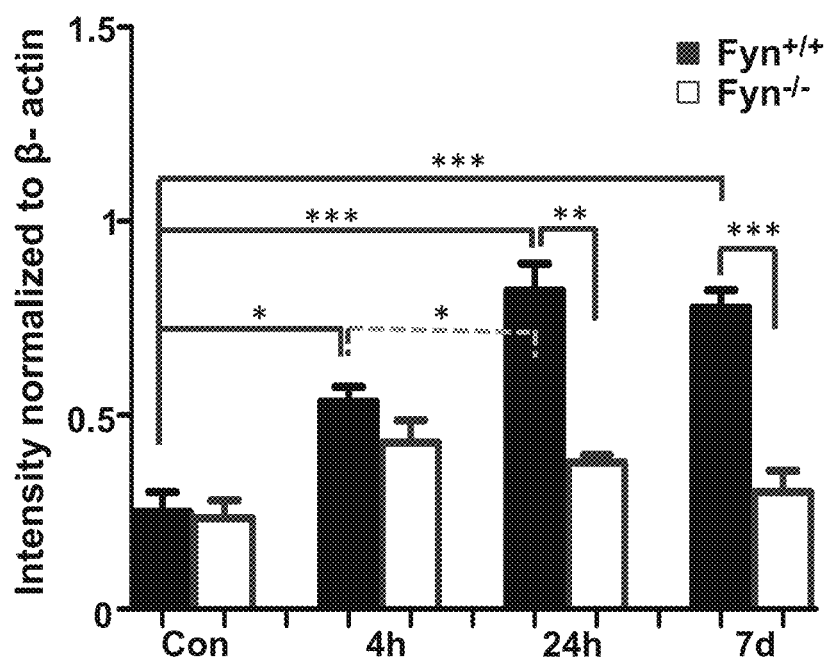

For Western blotting, the hippocampal tissues were dissected from both fyn$^{+/+}$ and fyn$^{-/-}$ animals at 4 h, 24 h and 7d time points immediately after euthanasia and were snap frozen in liquid nitrogen. The tissues were homogenized and lysed in RIPA buffer containing 1% protease and phosphatase inhibitors (Thermo-Scientific, USA). For cell fractionation and protein extraction from cytoplasm or nucleus, we used the kit and standard protocol from Thermo Scientific (NE-PER™ Nuclear and Cytoplasmic extraction reagents; catalog number 78833). The hippocampal tissues were homogenized in 200 µl of cytoplasmic extraction reagent I (CER I). The samples were vortexed vigorously for 15 seconds to suspend the pellet followed by incubation in ice for 10 min. After incubation, 11 µl of cytoplasmic extraction reagent II (CER II) was added followed by repeated vortexing and ice incubation steps. The samples were then centrifuged at 16,000×g for 5 min. The supernatant (cytoplasmic extract) was collected and the pellet was re-suspended in 100 µl of ice-cold nuclear extraction reagent (NER) followed by repeated vortexing for 15 seconds and ice incubation for 10 min for the total of 40 min. The samples were then centrifuged at 16,000×g for 10 min. The supernatant (nuclear extract) was collected and stored in −80° C. for later analysis. The protein concentration from tissue lysates were determined using the Bradford assay kit (Biorad, USA). Equal amounts of protein (40 µg) was loaded in the wells of precast gels along with the molecular weight marker. The gels were run at 100V for 1-2 h at RT until the bromophenol dye reached at least 0.5 cm from the bottom of the plate. The proteins were transferred onto the nitrocellulose membrane and the transfer sandwich was placed into a mini transfer blot unit (Biorad, USA) at 4° C. overnight at 25V for 14 h according to the manufacturer's instructions. Next day, the membrane was washed with PBS and 0.05% tween 20 (PBS-T) for 1 h followed by blocking with Fluorescent Western Blot blocking buffer (to avoid non-specific binding) (Rockland Immunochemicals, PA, USA) in PBS with 0.05% tween 20 at RT. After the blocking step, the blots were washed twice for 15 min each with PBS-T and probed with primary antibodies of interest overnight at 4° C. The following day, the membrane was incubated with IR-680 or IR-800 dyes (1:10000, LiCor, USA) followed by further washes with PBS-T as described earlier. The β-actin was used as a loading control for cytosolic fractions and lamin-B for nuclear fractions. Fluorescent Western Blotting blocking buffer with 0.05% tween 20 was used as a diluent for both primary and secondary antibodies. The bands were identified using Odyssey IR imaging system and were quantified using imageJ software and normalized with the β-actin.
Results To understand the molecular mechanism of microglial activation mediated by the Fyn kinase during epileptogenesis, we tested the levels of Fyn and phosphorylated Src (pSrc-416) in the hippocampus at 4 h, 24 h, and 7d post-SE. The Western blot analysis revealed a significant increase in both Fyn and pSrc-416 levels at all the time points in the hippocampus of fyn$^{+/+}$ mice, except the cytosolic Fyn at 4 h, when compared with naïve control (FIGS. 4A-4D). As expected, total Fyn levels were not detected in fyn$^{-/-}$ mice, however, pSrc-416 levels were detected, but there were no significant differences between naïve control and SE groups. At 24 h and 7d post-SE, the pSrc-416 levels were significantly lower in fyn$^{-/-}$ mice when compared to fyn$^{+/+}$ mice (FIG. 4D). This may suggest that other members of the SFK may have a minor role in epileptogenesis. Further analysis of the fractionated samples revealed a significant increase in Fyn levels in both the cytoplasmic and nuclear fractions at all the time points in fyn$^{+/+}$ mice when compared to naïve control (FIGS. 4A-4C).

Example 5

Fyn Selectively Upregulated in the Microglia and Hilar Neurons of the Dentate Gyrus in Fyn$^{+/+}$ Mice During Post-SE Materials and Methods The same animals used in Example 4 were used here. Saracatinib and vehicle was also prepared in the same way as in Example 2. Diazepam was also administered as in Example 2. SE quantification was also performed as in Example 2.

For perfusion, we used 4% paraformaldehyde (PFA) solution (Acros Organics, USA) in 0.1M phosphate buffer saline (PBS) at pH 7.2. Antibodies used were the same as in Example 4.

For IHC, mice were transcardially perfused with 4% PFA in 0.1M PBS (4% PFA in 0.1M PBS) under terminal anesthesia. The tissues were collected and post-fixed in the same solution for 4 h at 4° C. After 4 h, they were cryopreserved in 25% sucrose solution for 3-4 days at 4° C. (Cosgrave et al., 2008). The tissues were then embedded in gelatin (15% type A gelatin, 7.5% sucrose, and 0.1% sodium azide in PBS, Sigma, Mo., USA), wrapped in the cling film, and stored overnight at 4° C. The gelatin-embedded tissue blocks were prepared by snap-freezing in the liquid nitrogen, using iso-pentane, and were then stored in −20° C. prior to cryosectioning (Beamer et al., 2012; Cosgrave et al., 2008). The coronal brain sections, 15 m thickness, from the tissue block were cut using CryoStar NX70 cryostat (specimen head temperature −20° C.; blade temperature −16° C.; trim section thickness 30 m; Thermo Scientific, MA, USA). The sections were collected on chrome alum gelatin (Pfaltz and Bauer, Conn., USA) coated slides. The details of brain section sampling method, to represent different regions of the hippocampus (rostral to caudal) on a slide, has been described in our previous publication (Puttachary et al., 2016a). The sections were then either processed for IHC immediately or were stored in −20° C. for later use. Prior to IHC, antigen retrieval was performed on the brain sections using citrate buffer (10 mM citric acid, 0.05% tween 20, pH 6.0) for 20 min at 95-100° C. The sections were washed with 0.1M PBS for an hour at room temperature (RT) followed by incubation with 10% donkey serum in PBS. The sections were then incubated with primary antibodies of interest (Fyn, PKCδ, 4-HNE, gp91$^{Phox}$ and IBA1) overnight at 4° C. (48 h for NeuN). All new batch of primary antibodies were titrated to determine the optimum concentration. In addition to neutralizing IgG antibodies against primaries, primary antibody omission step was run as a negative control. Next day, the sections were washed with PBS for an hour at RT and probed with appropriate secondary antibodies (FITC or CY3 conjugated, or biotinylated), for an hour, at RT followed by subsequent washing with PBS and then treated with streptavidin CY3 (only biotinylated ones) for an hour. The sections were washed in PBS, and finally with water to remove salt crystals and coverslipped with vectashield containing 4′,6-diamidino-2-phenylindole (DAPI) to stain nuclei. To observe the extent of neurodegeneration in the hippocampus, we did FJB-NeuN double staining. The brain sections were first stained with NeuN followed by FJB staining as described earlier (Puttachary et al., 2016b; Rao et al., 2006; Todorovic et al., 2012). For FJB staining, the sections were incubated in 0.006% potassium permanganate solution for 5-10 min with slow shaking. They were thoroughly washed twice with distilled water for a minute. The slides were submerged in 0.0003% FJB-0.1% acetic acid solution for 10 min in dark followed by 3 washes for one minute each. The slides were air-dried in the dark at RT, cleared with xylene and then mounted with surgipath acrytol (Surgipath, Leica Biosystems, Ill.).

For imaging, we used Axiovert 200M Zeiss inverted fluorescence microscope equipped with Hamamatsu camera (Zeiss, Deutschland, Germany). Images were captured using HCImage live 4 software (Hamamatsu Corporation, Sewickley, Pa.). The software has the capability to measure a large number of parameters related to size, shape, intensity, and position. All the images were taken at 20× magnification at 2s exposure. Image J was used to quantify the cells from a known area (in square microns) (Schneider et al., 2012). Bilateral cell counts were done from minimum of 4 sections per animal as described in our previous publications (Beamer et al., 2012; Cosgrave et al., 2008, 2010a and 2010b; Puttachary et al., 2016a and 2016b). The areas of cell counting for all sections on a slide and from all the groups were kept constant. The NeuN positive cells with FJB staining were counted to determine neurodegeneration. IBA1 positive cells with Fyn/PKCd in the nucleus and/or cytoplasm alone were quantified to determine microgliosis. The DAPI staining was used to mark nuclei. Since there is no consensus on reliable and reproducible markers for reactive microglia, we considered the area of cell body, the number of branches, and the junctions to distinguish reactive microglia (also referred by some as M1-type microglia) from the resting or alternative type microglia (often referred by some as M2-type) (Andersson et al., 1991; Block, 2014; Torres-Platas et al., 2014; Walker and Lue, 2015). Initially, we derived these parameters from the resting microglia in the control brain section from a known area (e.g. CA3 region) to compare with reactive microglia derived from a similar area in the kainate treated groups at various timepoints. To consider a reactive microglia as positive for Fyn or PKCd in the cytoplasm or in the nucleus, we first set the threshold for cytoplasm and nucleus separately. The percentage of reactive microglia were derived from the total number of IBA1 positive cells. We further calculated the percentage of nuclear Fyn or PKCd positive reactive microglia from the total Fyn/PKCd positive reactive microglia.

Results

Figure 4E:
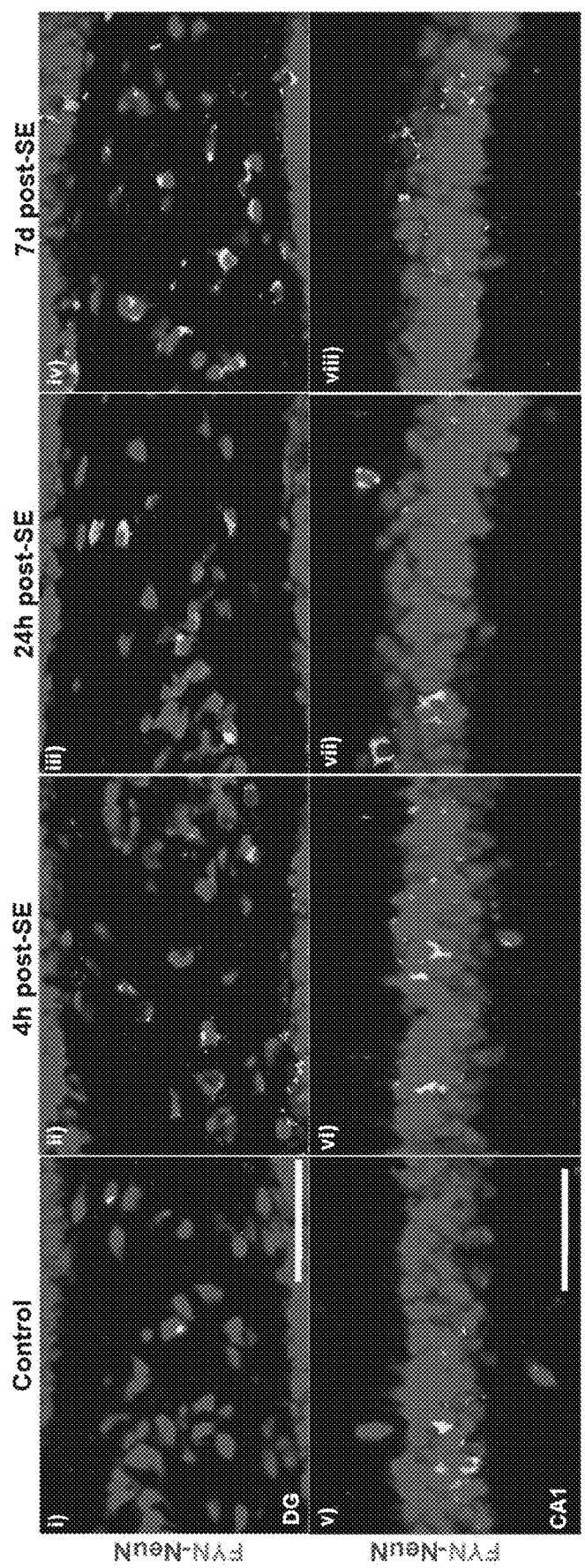
FIG. 4E shows immuno-histochemistry (IHC) images of the hilus of dentate gyrus demonstrating Fyn (yellow) co-localization in neurons in fyn$^{+/+}$ mice.
Figure 4F:
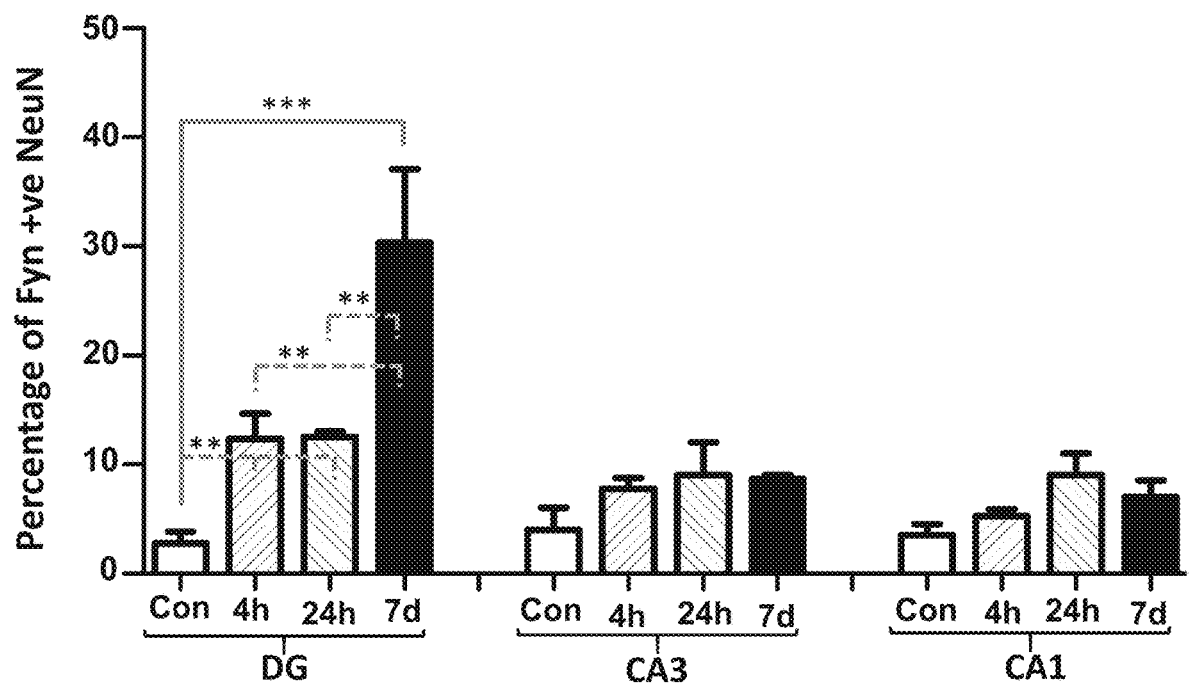
FIG. 4F shows that Fyn expression was significantly increased in the hilus of dentate gyrus (DG) at all the time points when compared to the control. No significant difference was observed in CA1 and CA3 regions ($p<0.01$, *$p<0.001$).
Figure 4G:
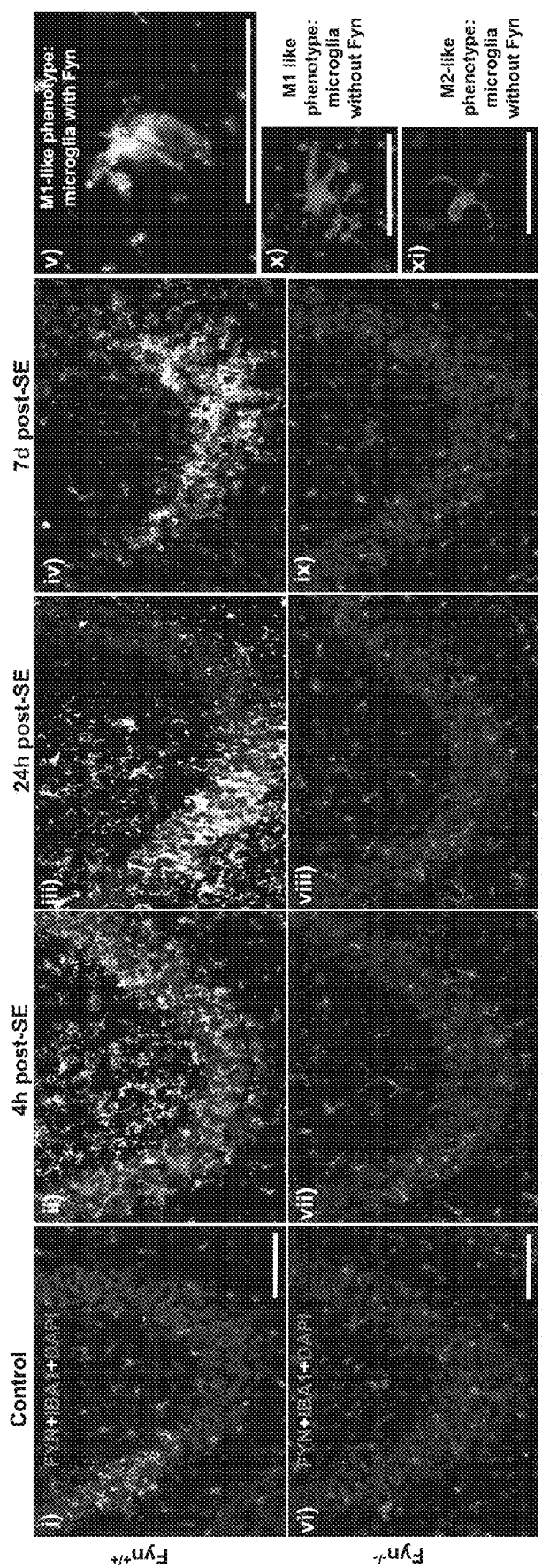
FIGS. 4G-4I show IHC images from CA3 region of the hippocampus showing Fyn immunoreactivity (green) at different time points (red, IBA1 for microglia; yellow/green, Fyn; blue, DAPI for nucleus). A representative high-power view images (FIG. 4G-v, x, xi) of the microglia (red) that resembled M1/M2-like phenotype with or without Fyn (green/yellow) at 24 h post-SE from the fyn$^{+/+}$ and fyn$^{-/-}$ are shown. The Images in the FIG. 4H represents Fyn immunoreactivity in the cytoplasm (i-iv) and its nuclear translocation (FIG. 4H, vi-green and viii-yellow) in the M1-like microglia (red). In the fyn$^{+/+}$ mice, at all time points, the microglia had M1-like phenotype with a large cell body (hypertrophied) and thick cytoplasmic processes (e.g.
Figure 4H:
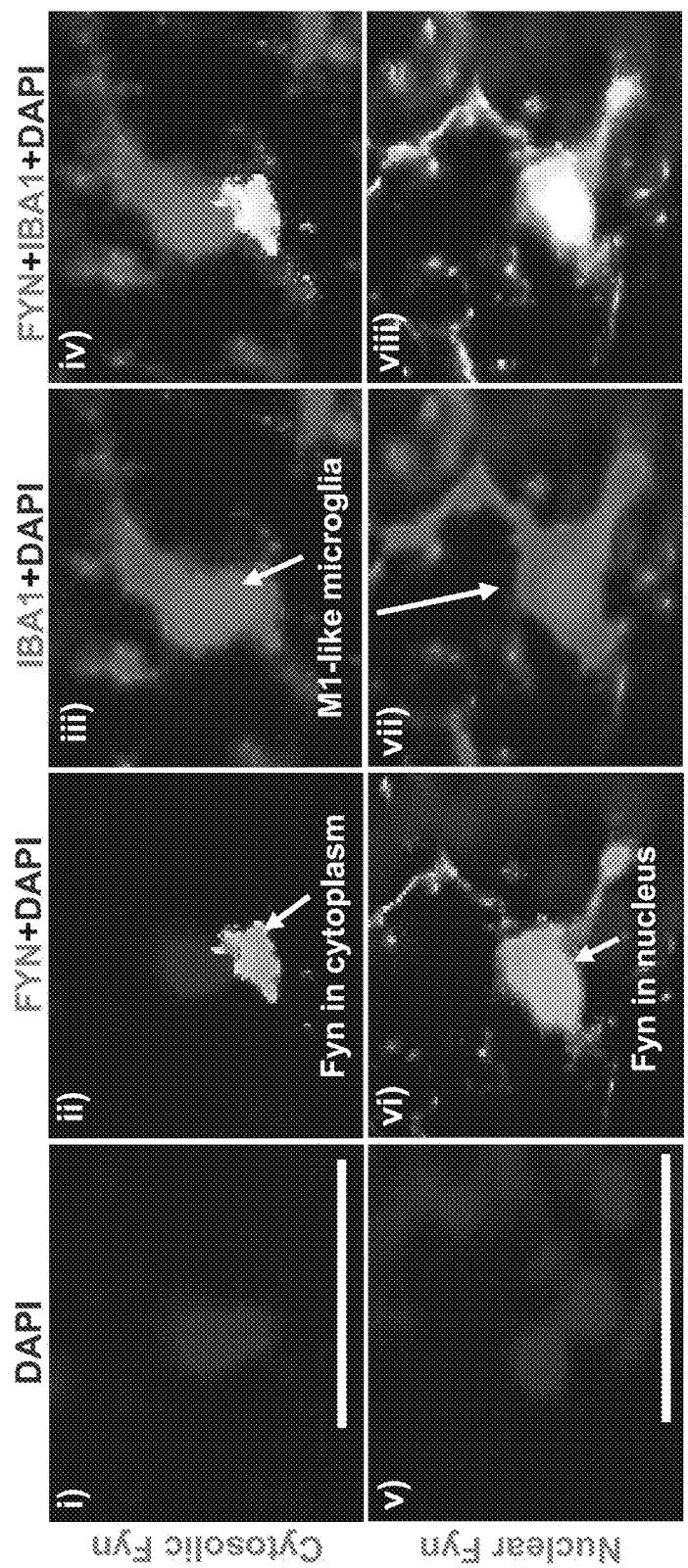
Figure 4I:
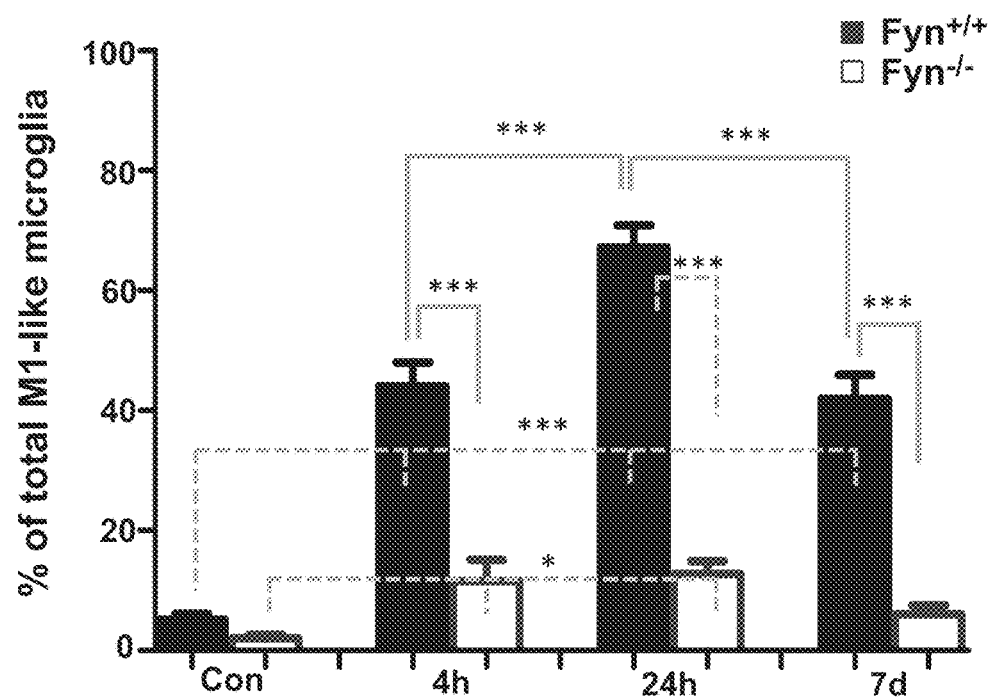
Figure 4J:
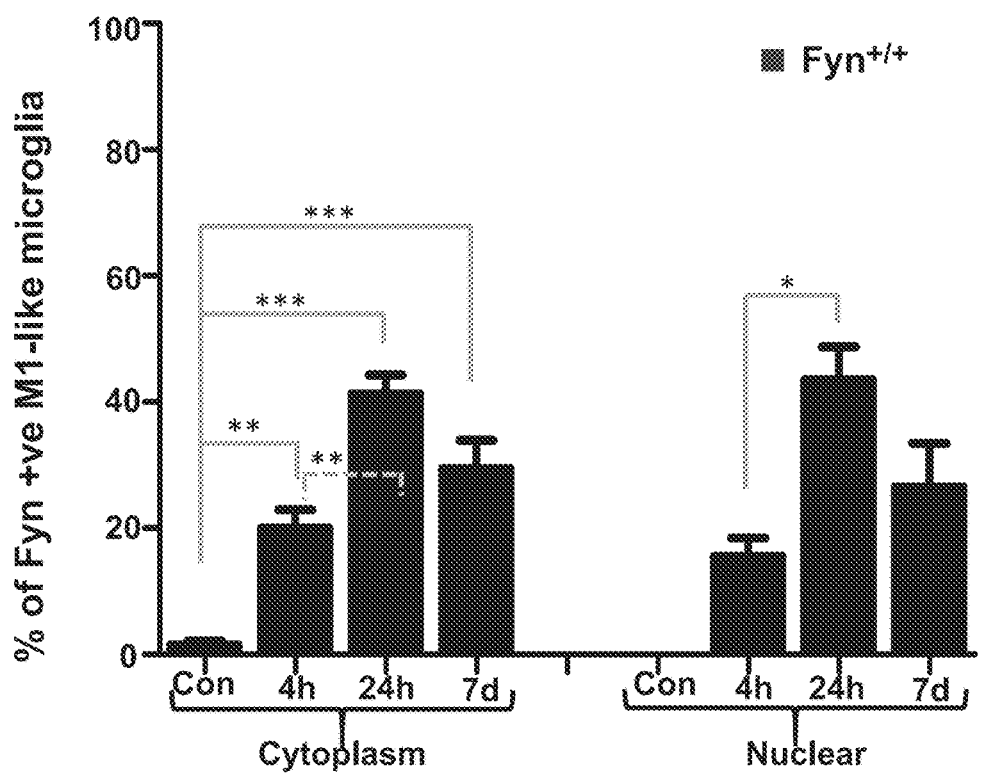
FIG. 4J shows Fyn was not detected in $fyn^{-/-}$ mice. In $fyn^{+/+}$ mice, there was a significant increase in both cytosolic and nuclear Fyn positive M1-like microglia at all the time points when compared to the control. One-way ANOVA, *$p<0.05$, $p<0.01$, *$p<0.001$; n=5-6. Scale bar, all 100 µm.
Figure 9A:
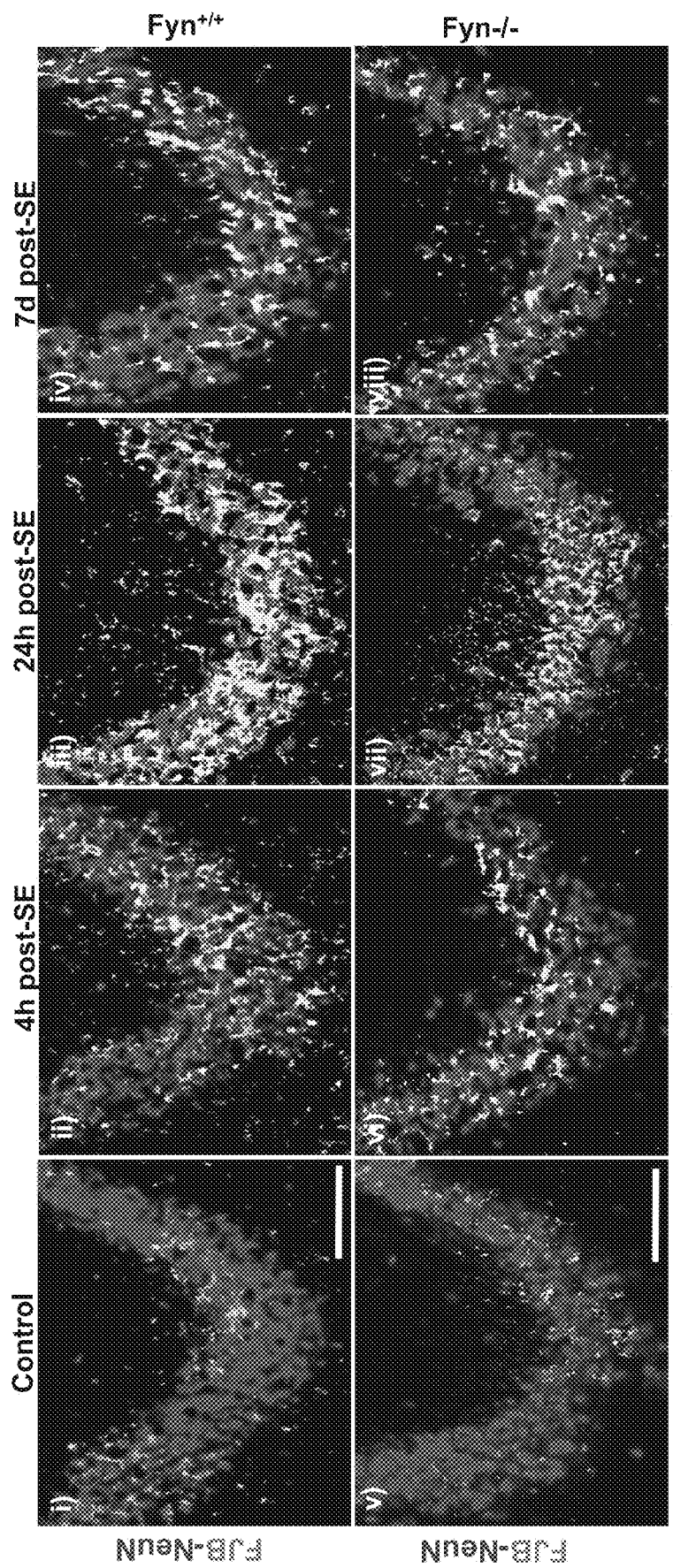
FIG. 9 is a pictorial and graphical representation of neurodegeneration. FJB-NeuN co-staining in CA3 region of hippocampus. FJB positive cells (yellow) were observed in the neurons (red) of the pyramidal cell layer of CA3 in both $fyn^{+/+}$ and $fyn^{-/-}$ mice at all time points. The maximum neurodegeneration was observed in CA3 and hilus in both the groups at 24 h post-SE (FIG. 9A, iii and vii, and FIG. 9B). A significant difference in the number of FJB positive cells was observed in the DG and in other areas of hippocampus at all time points in $fyn^{+/+}$ and $fyn^{-/-}$ when compared to their respective controls. High number of FJB positive cells were observed at 24 h post-SE in $fyn^{+/+}$ in CA3 (FIG. 9A, iii) but they were reduced at 7d post-SE. Similar results were observed in $fyn^{-/-}$ where the neurodegeneration was diminished at 7d post-SE compared to other time points. In $fyn^{-/-}$ mice, there was increased neurodegeneration in pyramidal layer of CA3 (FIG. 9A, viii) but this was significantly lower compared to $fyn^{+/+}$ mice. Overall, neurodegeneration was reduced in $fyn^{-/-}$ compared to $fyn^{+/+}$ at all time points, especially at 24 h and 7d post-SE, in all areas of hippocampus. One-way ANOVA, *$p<0.05$, $p<0.01$, *$p<0.001$; n=5-6. Scale bar, all 100 µm.
Figure 9B:
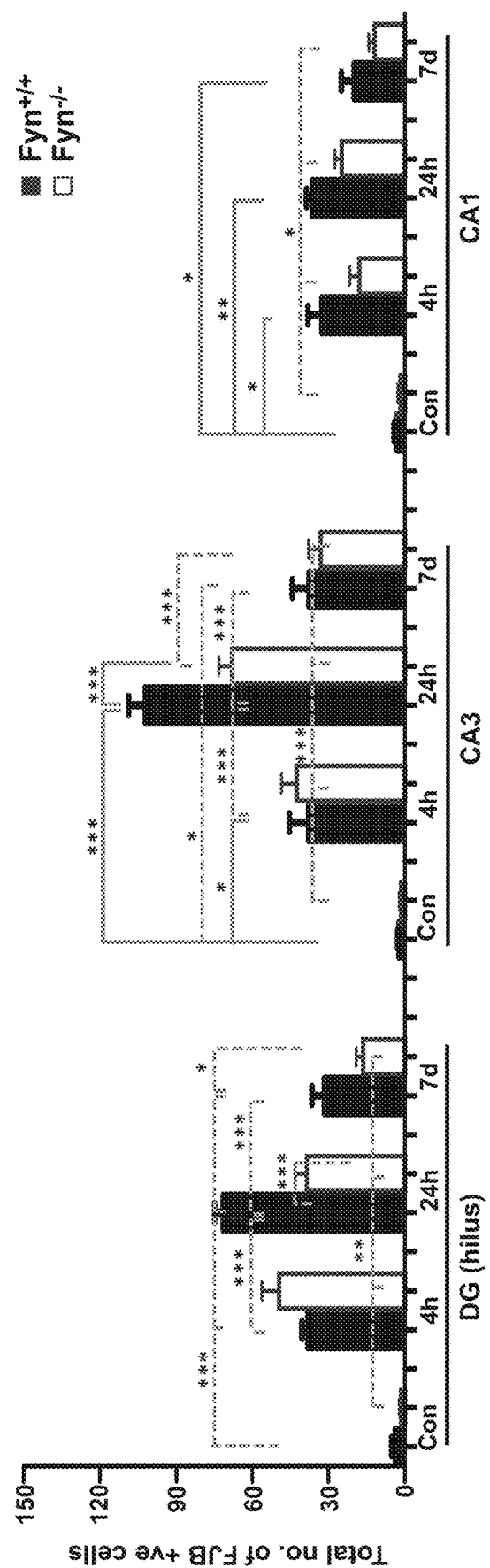

IHC of brain sections, double stained for neuron (NeuN) or microglia marker (IBA1) and Fyn, revealed a pattern of Fyn staining in neurons, and in the cytoplasm and nuclei of reactive microglia in the hippocampus and dentate gyrus (FIGS. 4E-4J). The pyramidal neurons in CA1 and CA3 regions of the hippocampus did not show increase in Fyn staining at any time point tested during the post-SE. However, the Fyn positive neurons in the hilus of dentate gyrus were significantly increased at all the time-points when compared to the control (FIGS. 4E and 4F). Interestingly, we also observed an increase in the number of FJB positive neurons in the hilus at these time points in fyn mice (FIG. 9B). Moreover, a significant increase in reactive microglia was also observed at 4 h, 24 h, and 7d in fyn$^{+/+}$ mice when compared to naïve control (FIGS. 4G and 4I). At 24 h and 7d, intense Fyn positive microglia were found in CA1 (not shown), CA3 (FIG. 4G), and the dentate gyrus (not shown). The vast majority of these microglia resembled M1-like phenotype with thick cytoplasmic process and often multinucleated with a large cell body. In these cell types, the Fyn was localized in the nucleus (FIGS. 4G, 4H, and 4J). In contrast, the fyn$^{-/-}$ mice did not show any Fyn staining, and the vast majority of microglia had M2-like phenotype or alternatively activated type morphology with a small soma and thin cytoplasmic processes (FIG. 4G). However, there was a significant increase in reactive type microglia at 4 h and 24 h, and a marginal increase at 7d post-SE in the fyn$^{-/-}$ mice was observed when compared with the naïve control (FIG. 4I). A similar pattern of Fyn staining in microglia was detected in other parts of the brain such as the entorhinal cortex, thalamus, and amygdala (data not shown).

Example 6

Figure 5A:
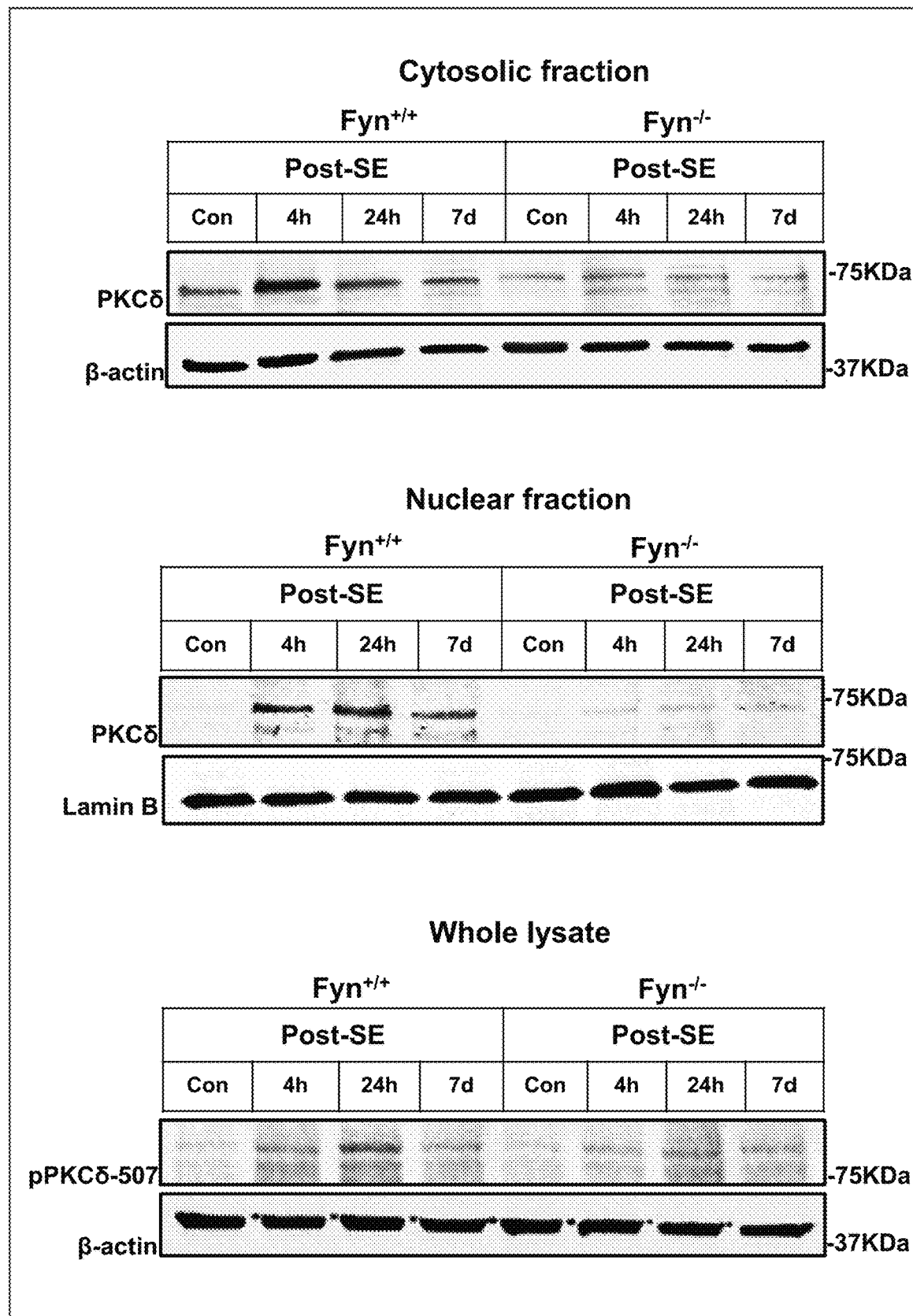
FIGS. 5A-5D are the Western blot analyses showing a significant increase in both the cytosolic and nuclear PKCδ levels, and also pPKCδ, in $fyn^{+/+}$ at all the time points compared to the control. The cytosolic PKCδ levels were relatively decreased at 7d post-SE, but the nuclear PKCd levels remained at the same levels at all the time points. In $fyn^{-/-}$ mice, the cytosolic PKCδ levels were increased significantly at all time points, while pPKCδ-507 levels were increased significantly at 24 h and 7d when compared to the control. However, their levels were significantly lower than the levels observed in $fyn^{+/+}$ mice (*$p<0.05$, $p<0.01$, *$p<0.001$). Nuclear translocation of PKCδ in $fyn^{-/-}$ was marginally increased, but this increase was much lower when compared to $fyn^{+/+}$ mice.
Figure 5B:
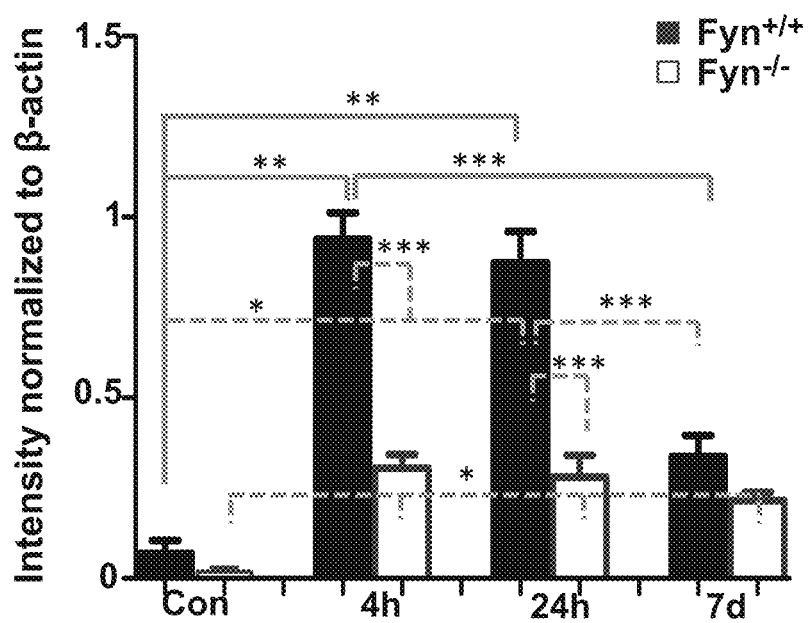
Figure 5C:
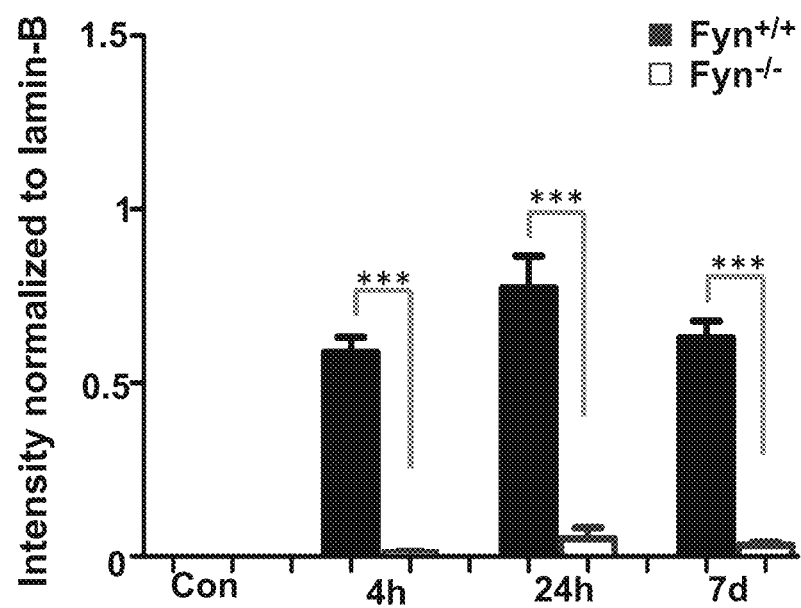
Figure 5D:
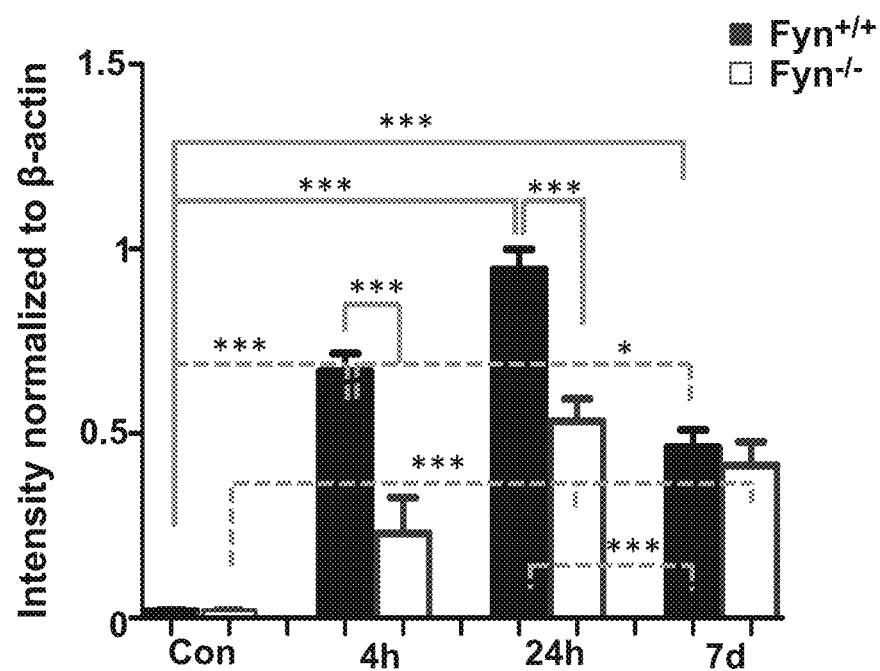
Figure 5E:
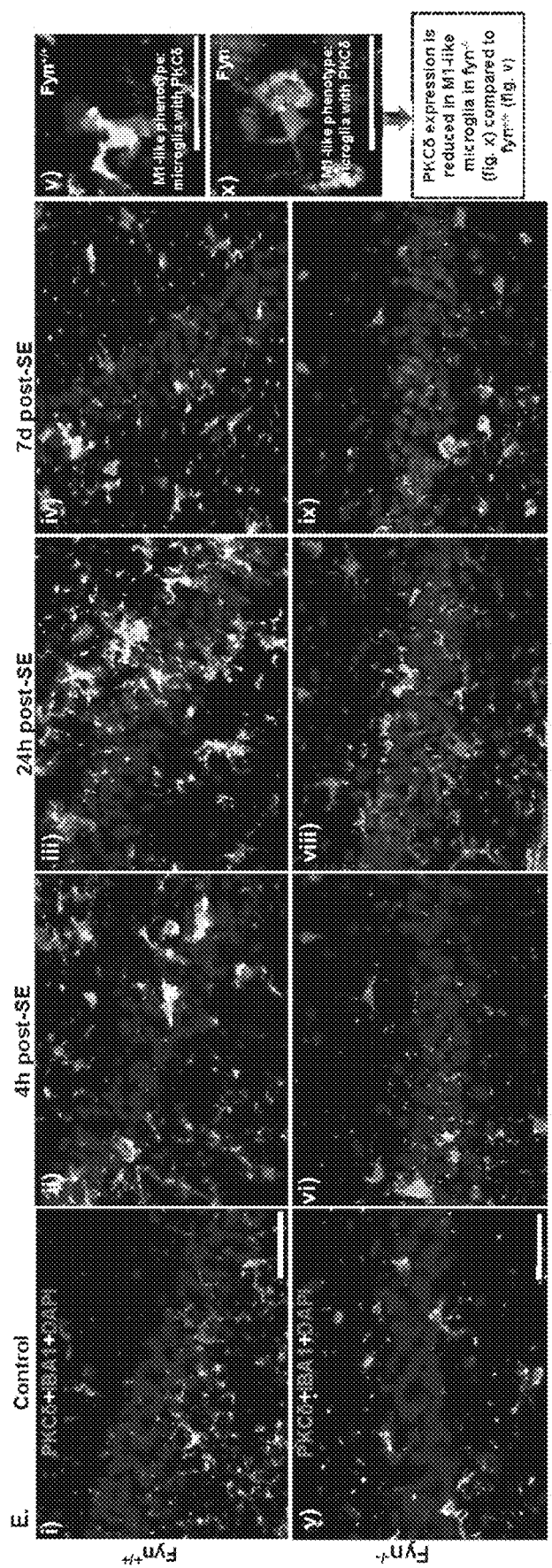
FIGS. 5E and 5F are IHC images of CA1 region of the hippocampus showing PKCδ (green or yellow) immunoreactivity in the M1-like microglia (red). In the $fyn^{+/+}$ mice, there were significant increase in the numbers of both cytoplasmic and nuclear PKCδ immunoreactive microglia at all time points when compared to the control. In $fyn^{-/-}$ mice, there was a significant reduction in their numbers, at all time points, in both the nuclei and cytoplasm (and also the intensity of staining) of the M1-like microglia when compared to $fyn^{+/+}$ mice (*$p<0.01$, $p<0.01$, *$p<0.001$). A high-power view of the images shows intense PKCδ staining in the nucleus and cytoplasm of M1-like microglia in $fyn^{+/+}$ and $fyn^{-/-}$ (FIG. 5E-v, -x). One-way ANOVA, *$p<0.05$, $p<0.01$, *$p<0.001$; n=5-6. Scale bar, 100 µm.
Figure 5F:
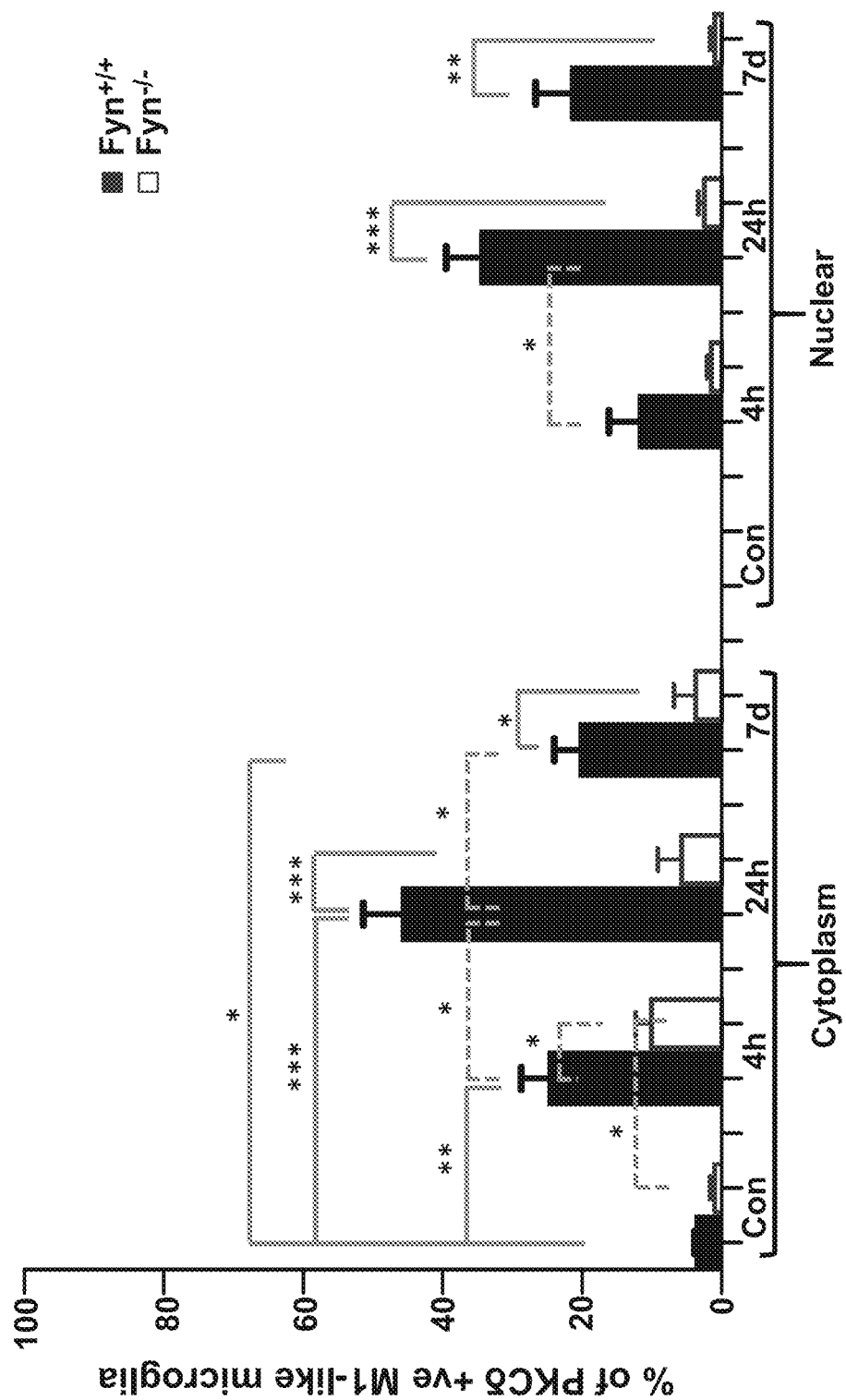

SE Significantly Increased Naïve and Phosphorylated PKCδ Levels in the Hippocampus of Fyn$^{+/+}$ Mice when Compared to fyn$^{-/-}$ Mice
Materials and Methods The same animals used in Example 4 were used here. Western blots were performed as in Example 4 and IHC as in Example 5. Saracatinib and vehicle was also prepared in the same way as in Example 2. Diazepam was also administered as in Example 2. SE quantification was also performed as in Example 2.
Results It was known that phosphorylated SFK (pSrc-416) activates PKCδ and translocates to the nucleus of microglia in cell culture and animal models of PD (Panicker et al., 2015; Saminathan et al., 2011). Therefore, we speculated that a similar mechanism may exist in the kainate model of epileptogenesis. In the fyn$^{+/+}$ mice, the Western blot analysis of proteins from the hippocampus revealed a significant increase in both the naïve full-length PKCδ and phosphorylated PKCδ (pPKCd-507) at 4 h, 24 h, and 7d post-SE when compared with the control (FIGS. 5A-5D). Since pSrc-416 levels were detected in fyn$^{-/-}$ mice, we also observed an increase in the levels of both full-length PKCδ and pPKCδ-507 at all time points. Further analysis of the nuclear fractions from the hippocampus, revealed a significant increase in PKCδ levels in the fyn$^{+/+}$ mice, but not in the fyn$^{-/-}$ mice (FIG. 5C). In concurrence with the Western blot results, IHC of the brain sections revealed a significant increase in both the numbers of PKCδ positive microglia as well as increase in intensity of staining in the nuclei of the reactive microglia in the hippocampus at 4 h, 24 h, and 7d time points (FIGS. 5E and 5F) in the fyn$^{+/+}$ mice. In the fyn$^{-/-}$ mice, there was a marginal increase in microglial cytoplasmic PKCδ over time, but there was no significant increase in the nuclear PKCδ (FIGS. 5E and 5F). In the hilus of dentate gyrus, we observed a transient increase in the PKCδ staining in neurons (data not shown).

Example 7

SE Significantly Increased Caspase-3 and Cleaved Caspase-3 Levels in the Hippocampus of Fyn$^{+/+}$ Mice when Compared to Fyn$^{-/-}$ Mice.
Materials and Methods The same animals used in Example 4 were used here. Western blots were performed as in Example 4 and IHC as in Example 5. Saracatinib and vehicle was also prepared in the same way as in Example 2. Diazepam was also administered as in Example 2. SE quantification was also performed as in Example 2.

Results

Figure 6A:
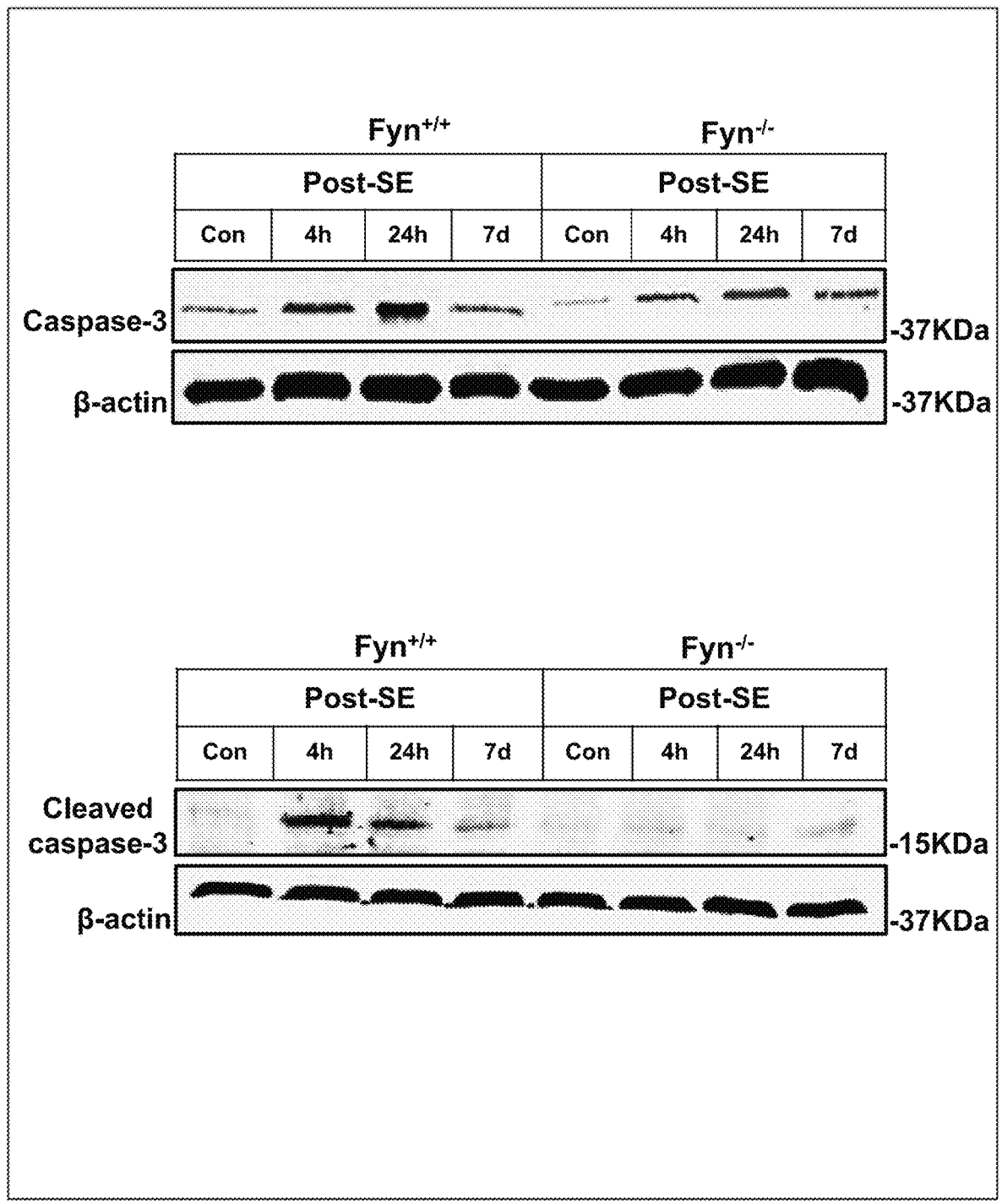
FIG. 6A shows that the caspase-3 levels were significantly increased at all time points in both groups.
Figure 6B:
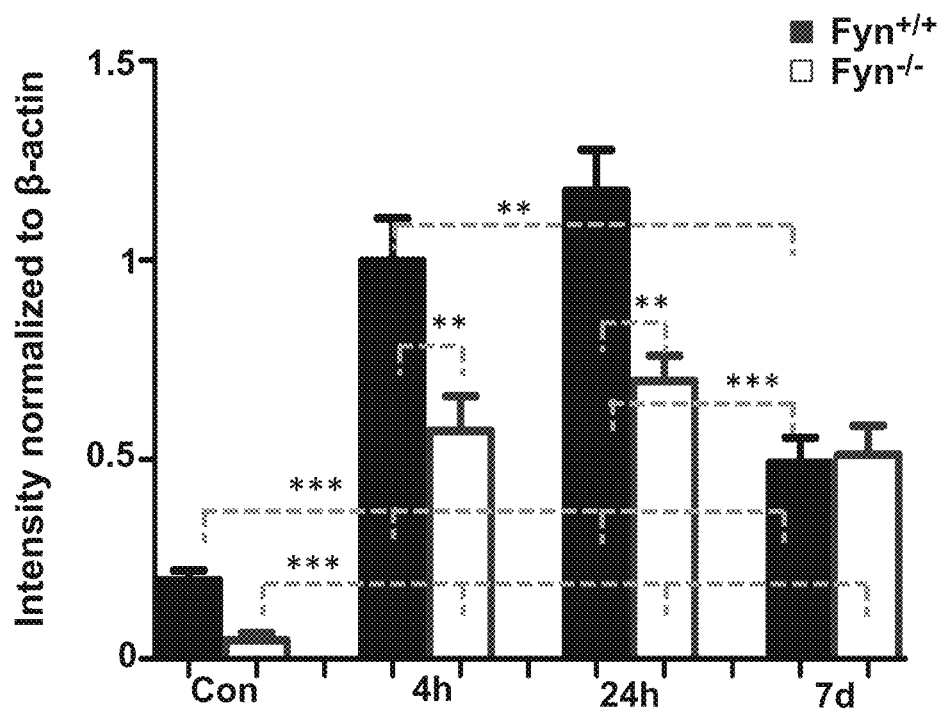
FIG. 6B shows that at 4 h and 24 h, the caspase-3 levels were significantly lower in $fyn^{-/-}$ in contrast to the $fyn^{+/+}$ mice.
Figure 6C:
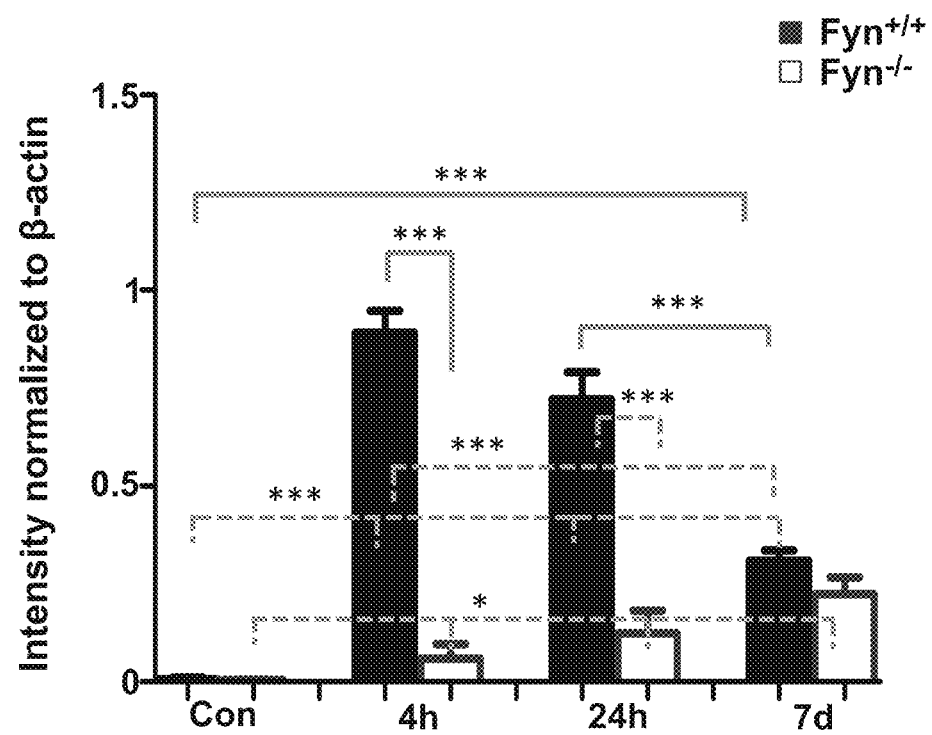
FIG. 6C shows the cleaved caspase-3 levels also significantly increased at all time points in $fyn^{+/+}$ when compared to the control, and when compared to the $fyn^{-/-}$ mice, except at 7d post-SE. In $fyn^{-/-}$ mice, cleaved caspase-3 levels also increased over time compared to the control, but their levels were significantly lower in $fyn^{+/+}$ mice at 4 h and 24 h time points. One-way ANOVA, *$p<0.05$, $p<0.01$, *$p<0.001$; n=5-6.

The PKCδ is cleaved by caspase-3 to cause neuronal death (Kaul et al., 2003; Kato et al., 2009; Kitazawa et al., 2005), therefore we tested the caspase-3 and cleaved caspase-3 levels in the hippocampus. There was an increase in the caspase-3 and cleaved caspase-3 levels at all time points in both fyn$^{+/+}$ and fyn$^{-/-}$ mice groups when compared with the respective controls (FIGS. 6A-6C). However, in the fyn$^{-/-}$ mice, the caspase-3 and cleaved caspase-3 levels were significantly lower at 4 h and 24 h post-SE when compared with the fyn$^{+/+}$ mice (FIGS. 6A-6C).

Example 8

Key Proinflammatory Cytokines Profile During Epileptogenesis in Fyn$^{+/+}$ and Fyn$^{-/-}$ Mice
Materials and Methods The same animals used in Example 4 were used here. Saracatinib and vehicle was also prepared in the same way as in Example 2. Diazepam was also administered as in Example 2. SE quantification was also performed as in Example 2.

For qRT-PCR, high capacity cDNA reverse transcription kit was purchased from Thermo Fisher Scientific, MA, USA; SYBR Green Master Mix was purchased from Applied Biosystems, CA, USA and the QuantiTect primer assays were purchased from Qiagen, Calif., USA. We used bead-based multiplex assay (Milliplex mouse cytokine kit from Millipore Mass., USA) to determine serum cytokine levels. Analytes such as anti-mouse IL-6 functional grade biotin (Cat. No. 36-7062-85) and anti-mouse IL-12 biotin (Cat. No. 13-7123-85) were purchased from Affymetrix eBioscience, CA, USA. Appropriate neutralizing IgGs for all primary antibodies were purchased from the same source as the primary antibodies.

RNA was extracted using the trizol chloroform (ThermoFisher Scientific) extraction method as described previously (Cosgrave et al., 2008; Seo et al., 2014). One microgram of RNA was used for reverse transcription using High Capacity cDNA Reverse Transcription Kit (Applied Biosystems, CA) yielding high quality single stranded cDNA. Quantitative RT-PCR was performed for the following genes using SYBR Green Mastermix (Applied Biosystems, CA, USA) with pre-validated qPCR primers. Primers for IL-1β, iNOS, and TNF-α were purchased from QuantiTect Primer Assay (Qiagen, USA). The house keeping gene, 18S rRNA (Qiagen, M D, USA), was used in all qPCR experiments for normalization. No-template controls (NTCs) and dissociation curves were obtained for all experiments to exclude cross-contamination. The fold change in the mRNA expression was determined using cycle threshold (Ct) values for the genes of interest and also for the housekeeping genes.

Cytokine levels were assessed from the serum using Luminex assay kit as described previously (Panicker et al., 2015). A five-fold dilution of serum was made with 0.1M PBS containing BSA. 40 μL of diluted serum was then added to the equal amount of primary antibodies, conjugated to magnetic microspheres, followed by overnight incubation at 4° C. in a clear bottom black 96-well plate. After incubation, each well was triple-washed using a magnetic washer and then incubated for an hour with secondary antibodies followed by three secondary washes. The samples were incubated for 30 min with streptavidin/phycoerythrin followed by two additional washes. All assays were done in duplicates and previously known positive control and a negative control without primary antibodies were used simultaneously with the test samples. A Bioplex reader was used to read the 96-well plates. A standard curve of all the cytokines was prepared using standard cytokines (Peprotech).

Results

Figure 7A:
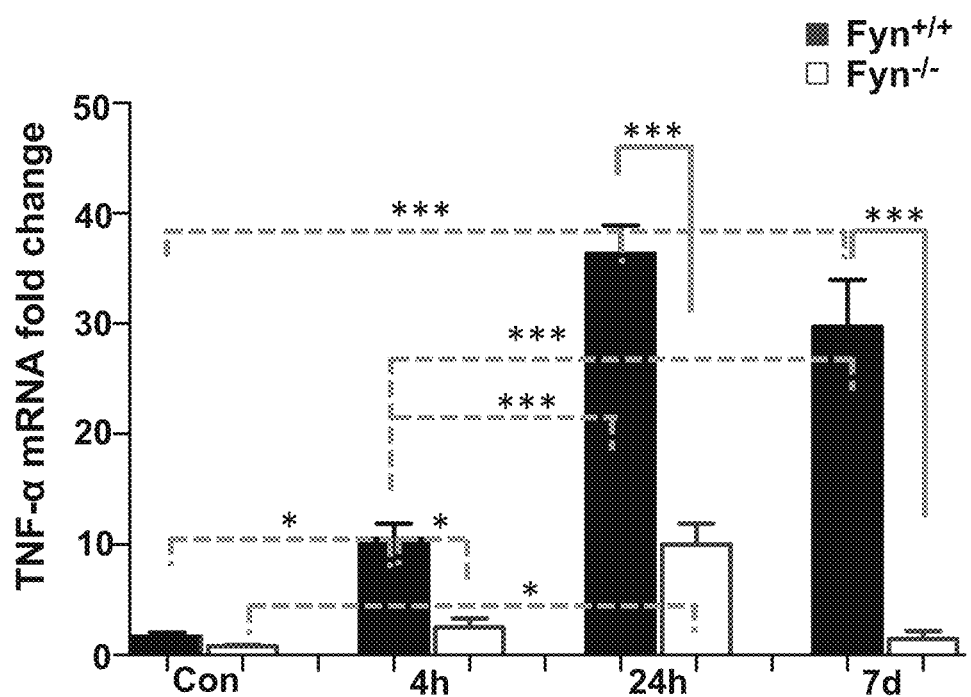
FIGS. 7A-7C show that in $fyn^{+/+}$ mice, the TNF-αmRNA levels were significantly increased at all the time points, while the IL-13 mRNA levels were increased at 24 h and 7d post-SE when compared to the controls. In $fyn^{-/-}$ mice, the TNF-α mRNA levels were significantly reduced at all time points, and IL-10 levels at 24 h post-SE when compared to the $fyn^{+/+}$ mice. *$p<0.05$, $p<0.01$, *$p<0.001$; n=5-6. The iNOS mRNA levels were increased at all time points in $fyn^{+/+}$ mice when compared to the control, especially at 4 h post-SE, while its levels did not change significantly in $fyn^{-/-}$ mice when compared to the control. However, there was a significant reduction in mRNA levels at 7d post-SE when compared between $fyn^{+/+}$ and $fyn^{-/-}$ mice.
Figure 7B:
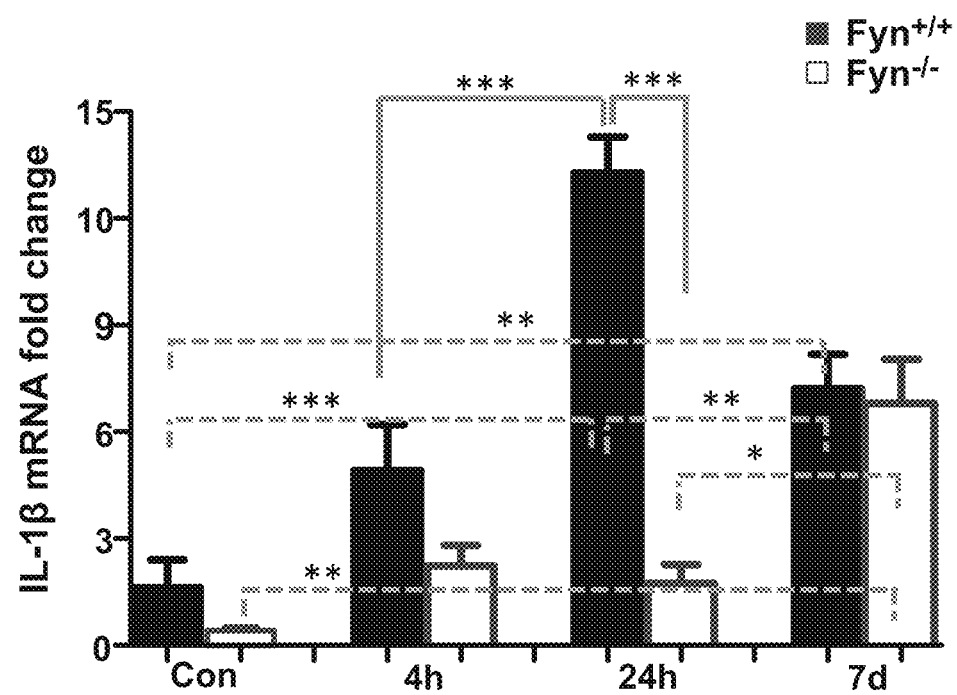
Figure 7C:
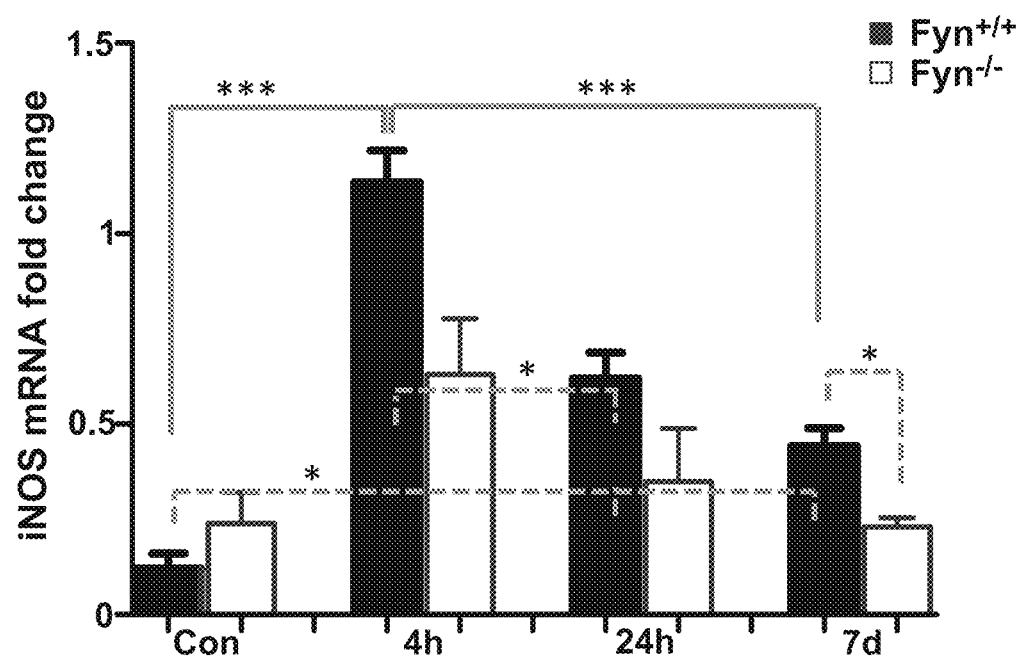

It has been demonstrated that PKCδ translocation to the nucleus initiates transcription of proinflammatory cytokines and iNOS in M1-like microglia (Bujor et al., 2011; Gordon et al., 2016). Since we found the PKCδ translocation to the nucleus in microglia, which also had M1-like phenotype (large cell body, thick cytoplasmic process), we further investigated whether it has an effect on proinflammatory cytokines in the hippocampus and serum. We utilized quantitative RT-PCR for mRNA assay for the hippocampus and multiplex cytokine assay for the serum. We found an increase in the TNF-α, IL-13, and iNOS mRNA levels in the $fyn^{+/+}$ mice when compared to the control at 4 h, 24 h, and 7d time points (FIGS. 7A-7C). In the $fyn^{-/-}$ mice, the IL-1b mRNA was significantly increased at 7d, and TNF-α mRNA at 24 h post-SE, however iNOS mRNA expression levels did not change significantly (FIGS. 7A-7C). However, when compared between the groups, the TNF-α expression was significantly higher at all the time points, while the IL-1β at 24 h and the iNOS at 7d post-SE.

Figure 7D:
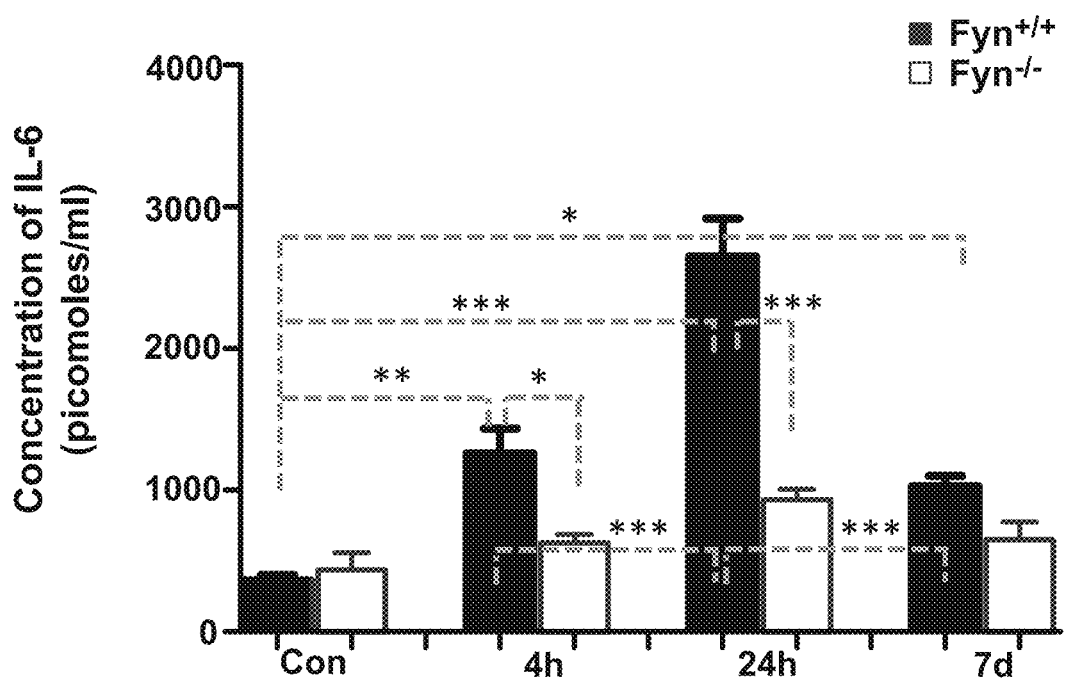
FIGS. 7D and 7E show the serum IL-6 and IL-12 levels were significantly higher, except IL-12 at 7d post-SE, in $fyn^{-/-}$ mice when compared to the controls at all time points. In $fyn^{-/-}$ mice, the IL-6 levels were marginally increased at 24 h, while the IL-12 levels were significantly higher at all time points when compared to the controls. When their levels were compared between the groups at various time points, there was a reduction in the IL-6 levels at 4 h and 24 h post-SE, but there were no significant differences in IL-12 levels between the groups. One-way ANOVA, *$p<0.05$, $p<0.01$, *$p<0.001$. n=5-6.
Figure 7E:
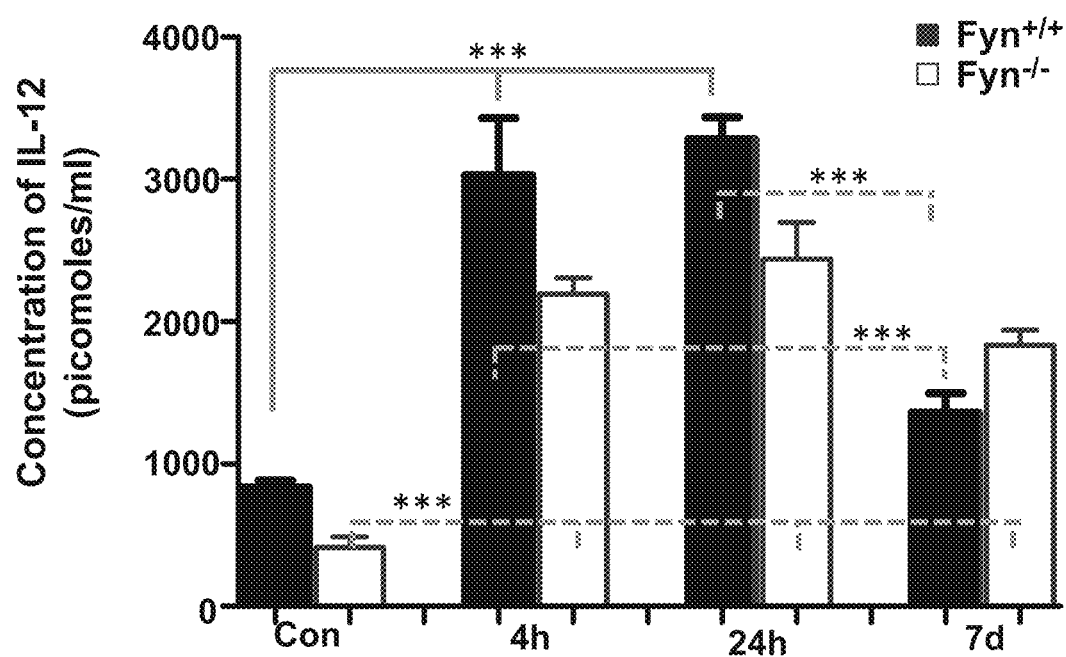

Multiplex cytokine assay of the serum revealed a significant increase of both IL-6 and IL-12 levels at all the time points in the $fyn^{+/+}$ mice when compared with the control (FIGS. 7D-7E). Interestingly, in the $fyn^{-/-}$ mice, the IL-12 levels were upregulated at all time points, but the IL-6 levels were only marginally increased at 24 h post-SE (FIGS. 7D-7E). When their levels were compared between the groups, IL-6 levels, but not IL-12, were significantly reduced in the $fyn^{-/-}$ mice when compared to the $fyn^{+/+}$ mice at 4 h and 24 h post-SE (FIGS. 7D-7E). Other cytokines mRNA or proteins levels were undetectable at all three time points.

Example 9

Nitro-Oxidative Stress Markers in the Hippocampus During Epileptogenesis in $Fyn^{+/+}$ and $Fyn^{-/-}$ Mice Materials and Methods The same animals used in Example 4 were used here. Western blots were performed as in Example 4 and IHC as in Example 5. Saracatinib and vehicle was also prepared in the same way as in Example 2. Diazepam was also administered as in Example 2. SE quantification was also performed as in Example 2.

Results

Figure 8A:
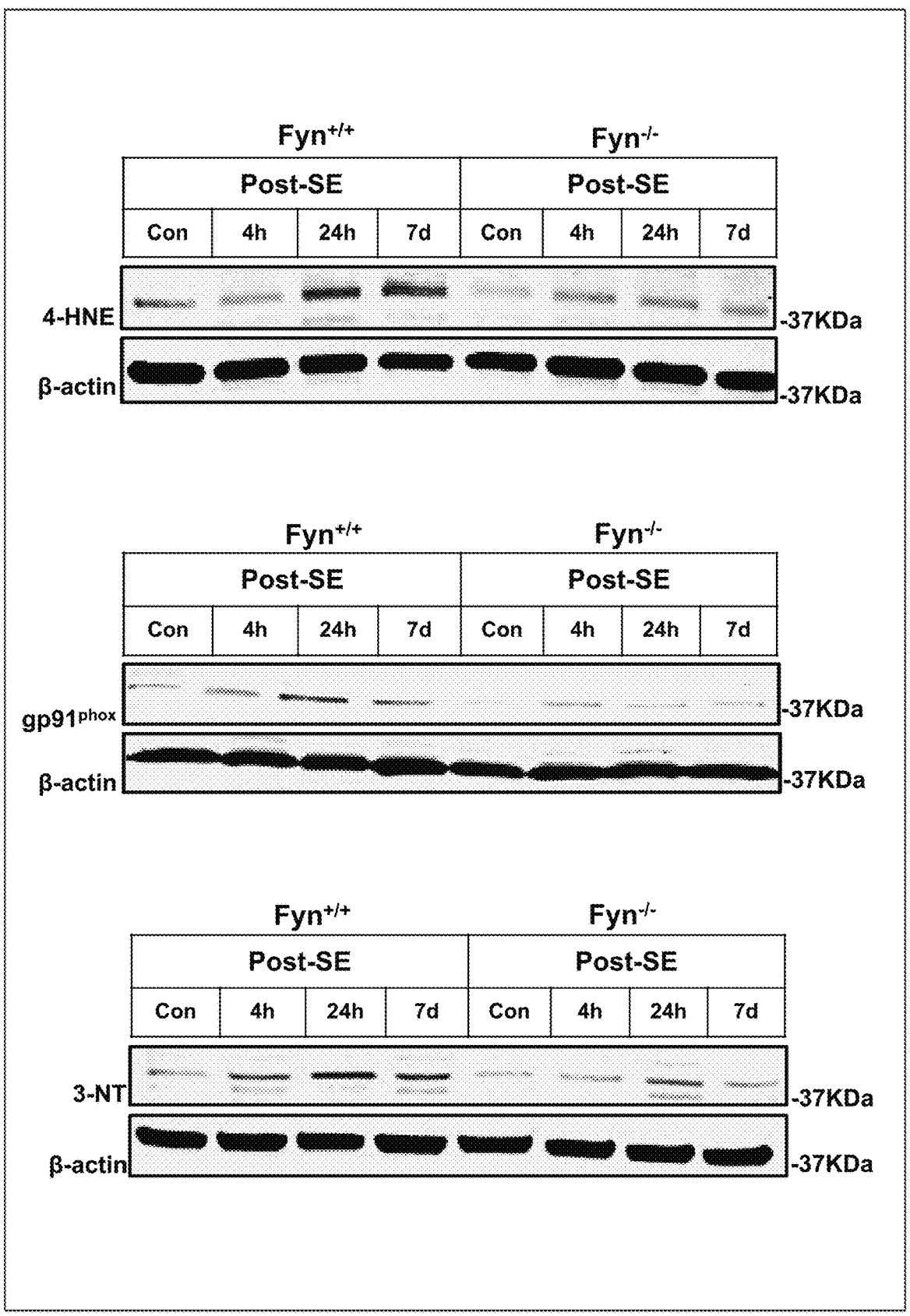
FIGS. 8A-8D show increased levels 4-HNE and gp91$^{phox}$ were observed in the hippocampus at all the time points, in both groups (except at 7d for 4-HNE in $fyn^{-/-}$), when compared to their respective controls. The 3-NT levels were also increased at all the time points in both $fyn^{-/-}$ and $fyn^{+/+}$ mice when compared to their respective controls. At 24 h and 7d post-SE, 4-HNE, gp91$^{phox}$ and 3-NT levels were significantly reduced in $fyn^{-/-}$ mice in contrast to $fyn^{+/+}$ mice. *$p<0.05$, $p<0.01$, *$p<0.001$; n=5-6.
Figure 8B:
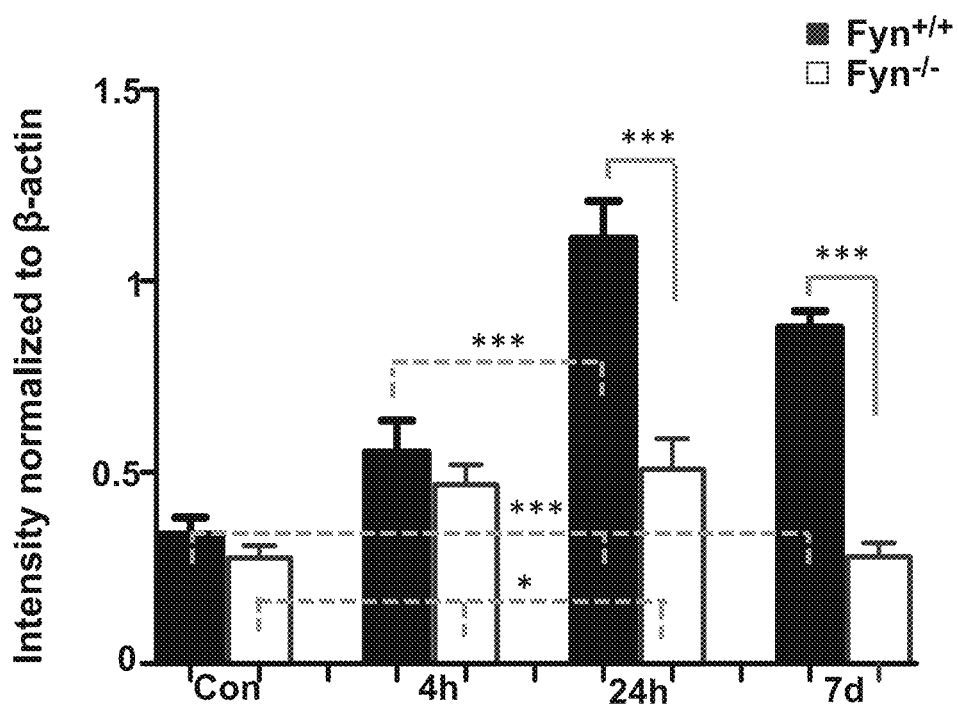
Figure 8C:
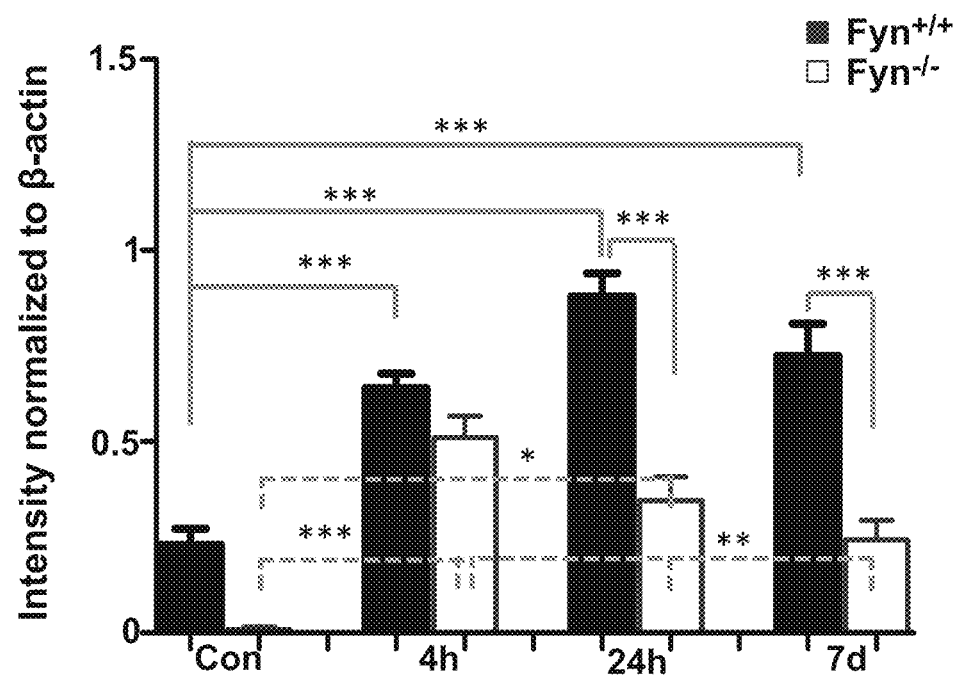
Figure 8D:
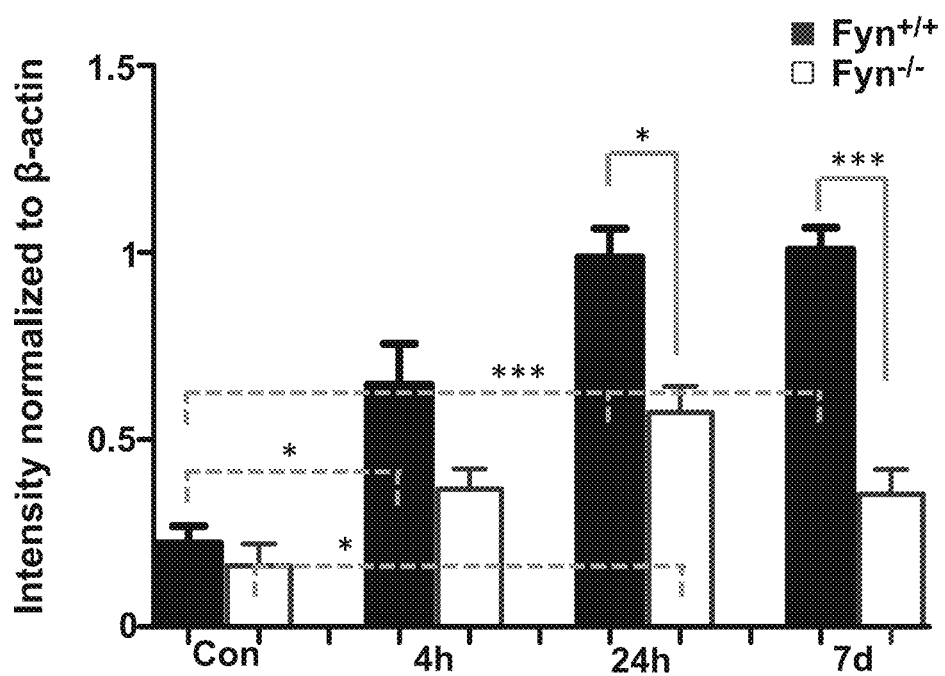
Figure 8E:
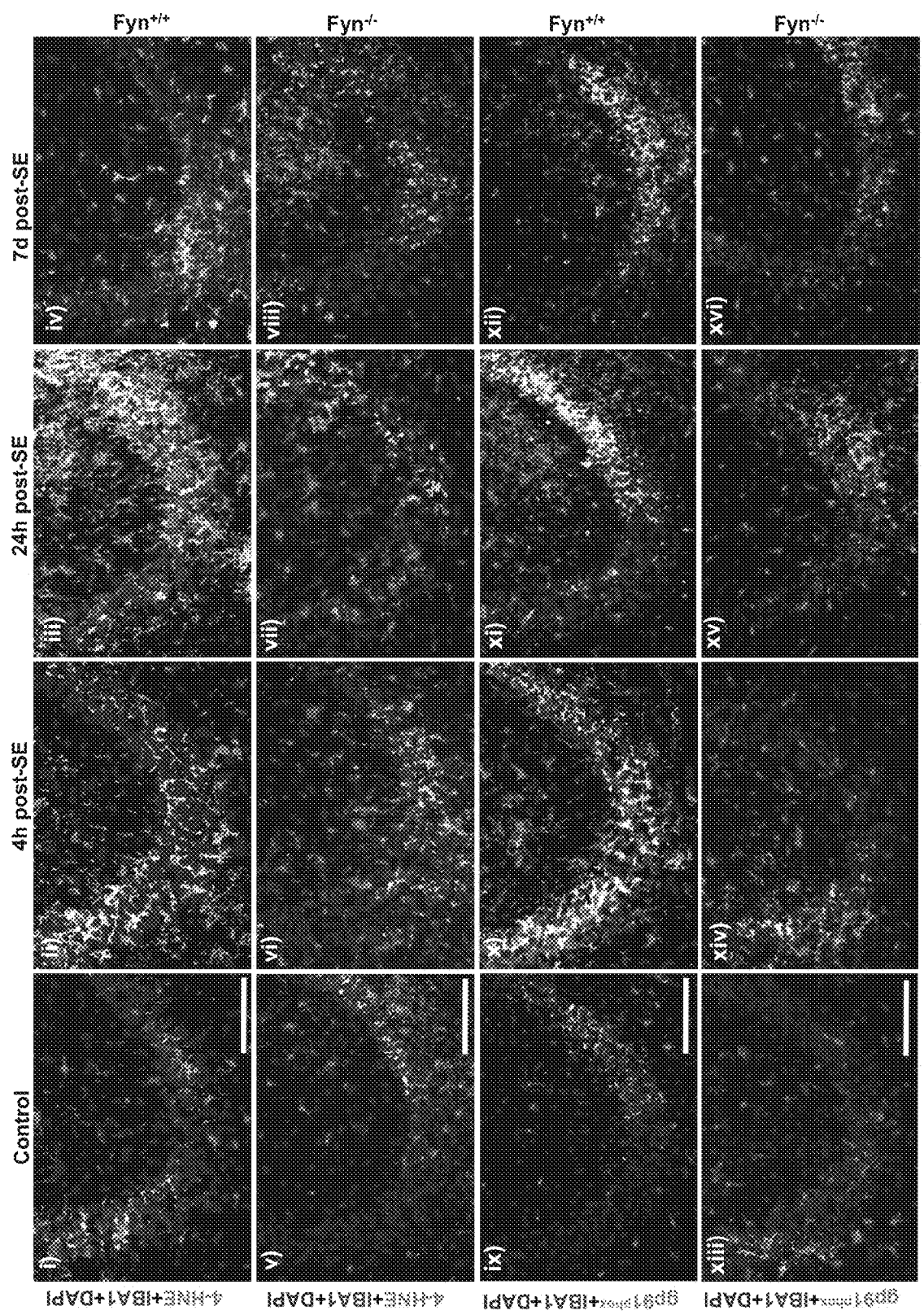
FIG. 8E shows IHC images of CA3 region of the hippocampus showing the 4-HNE and gp91$^{phox}$ immunoreactive cells (IBA1 (red) and DAPI (blue) in all panels; 4-HNE (green/yellow) in panels i) to viii) and gp91$^{phox}$ (green/yellow) in panels ix) to xvi) in FIG. 8E). Scale bar, all 100 µm.
Figure 8F:
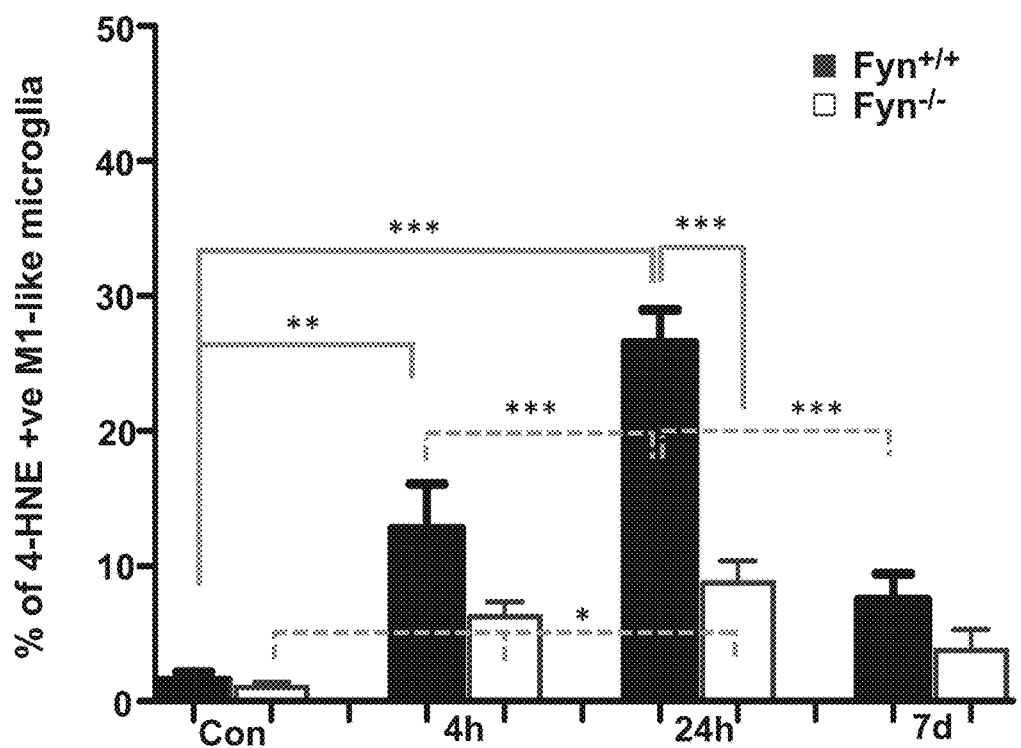
FIGS. 8F and 8G show cell quantification. The IBA1 positive microglial processes that were in close proximity to the pyramidal cell membranes in the CA3 region were counted. The 4-HNE and gp91$^{phox}$ immunopositive cells were increased at all time points in $fyn^{+/+}$ mice compared to the control. The maximum increase was observed at 24 h post-SE. A significant reduction was observed in the gp91$^{phox}$ positive microglia, but not the 4-HNE, at 7d post-SE in $fyn^{-/-}$ when compared to $fyn^{+/+}$ mice. In $fyn^{-/-}$ mice, there was a significant increase in both 4-HNE and gp91$^{Phox}$ positive cells at all time point, except at 7d, compared to controls. One-way ANOVA, *$p<0.05$, $p<0.01$, *$p<0.001$; n=5-6. Scale bar, all 100 m.
Figure 8G:
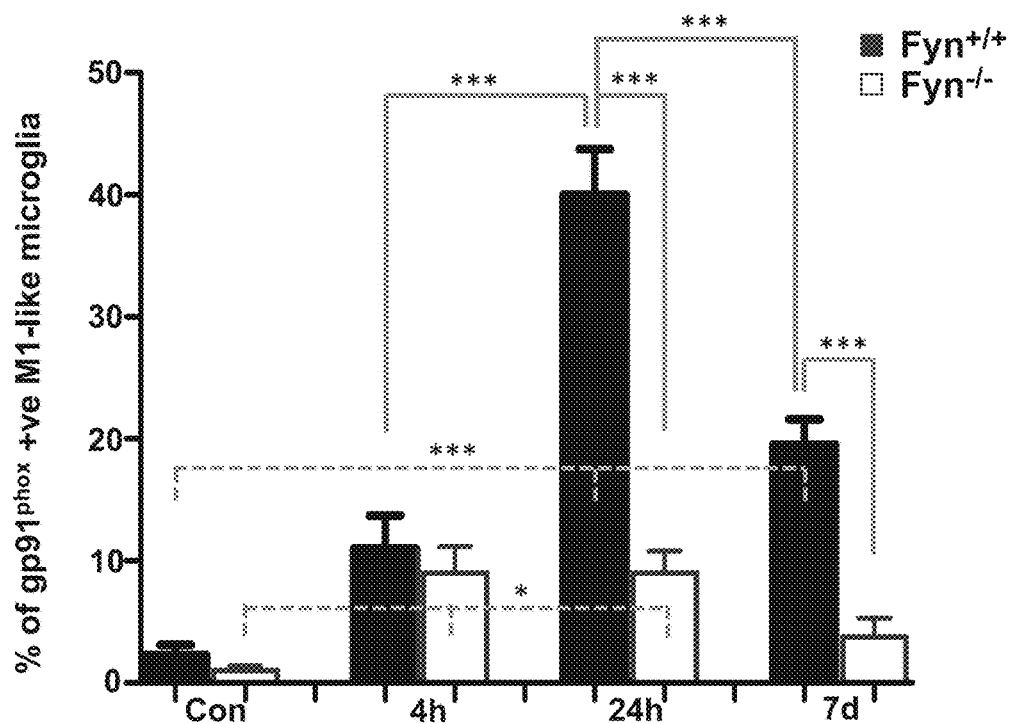

The phosphorylated PKCδ activates p47$^{phox}$, the cytosolic subunit of NOX2, which forms a functional complex with the membrane associated gp91$^{phox}$ to activate NOX2 signaling pathway and drives ROS and RNS production (Bedard and Krause, 2007; Fontayne et al., 2002). In this study, we quantified nitro-oxidative stress markers; gp91$^{phox}$, 4-HNE, and 3-NT levels from the hippocampus by employing IHC and WB methods. The 4-HNE levels were significantly increased at 24 h and 7d in the $fyn^{+/+}$ mice, while gp91$^{phox}$ and 3-NT levels were upregulated in both $fyn^{+/+}$ and $fyn^{-/-}$ mice at all time points when compared with their respective controls (FIGS. 8A-8D). All three markers were significantly decreased at 24 h and 7d post-SE in the $fyn^{-/-}$ mice when compared with the $fyn^{+/+}$ mice. At cellular level, their expression was predominantly in the microglia (FIG. 8E), however, neurons and a few astrocytes were also immunoreactive to these markers (data not shown). When compared between the groups at 24 h and 7d post-SE, we observed a large number of gp91$^{phox}$ containing reactive microglia in the hippocampus in the $fyn^{+/+}$ mice (FIG. 8E). Their numbers significantly reduced in the $fyn^{-/-}$ mice (FIG. 8G). Likewise, the numbers of 4-HNE and 3-NT positive neurons were also changed between the groups in the entorhinal cortex, amygdala, and the thalamus (data not shown).

Example 10

The FJB Positive Neurons Increased in the Hippocampus During Epileptogenesis in Both $Fyn^{+/+}$ and $Fyn^{-/-}$ Mice Materials and Methods The same animals used in Example 4 were used here. Western blots were performed as in Example 4 and IHC as in Example 5. Saracatinib and vehicle was also prepared in the same way as in Example 2. Diazepam was also administered as in Example 2. SE quantification was also performed as in Example 2.

Results

Having observed increased levels of nitro-oxidative stress markers, proinflammatory cytokines, cleaved caspase-3, and increased expression of Fyn and PKCδ levels in microglia of the hippocampus during epileptogenesis, we were interested to find out the extent of neurodegeneration in the hippocampus. We confirmed this by staining the brain sections with FJB and NeuN. There were significantly more numbers of degenerating neurons in the hippocampus at all time points in both groups when compared to their respective controls (FIGS. 9A and 9B). This suggest that Fyn alone has little impact on neurodegeneration during epileptogenesis. Although the numbers of FJB positive neurons decreased at 7d post-SE in both groups, overall they were significantly lower in $fyn^{-/-}$ mice at 24 h post-SE in CA3 region of the hippocampus and the dentate gyrus when compared with the $fyn^{+/+}$ mice (FIG. 9B).

Example 11

The Saracatinib Post-Treatment in the Rat Kainate Model Prevented or Modified Epileptogenesis Materials and Methods Rats were used in the following example. The rats were treated as per the materials and methods of Examples 2-10 except for the following. Fourteen rats were used and implanted with telemetry device 10 days prior to the induction of SE, with RLD of kainate, as described previously (Puttachary et al., 2016b). The telemetry device used was CTA-F40 PhysioTel™ telemetry device (Data Science International, Minneapolis, USA) for video-EEG recording.

Results

Disabling the Fyn kinase function, either by pretreatment with saracatinib or fyn KO, prior to SE induction impacts the initial severity of SE and thus compromises the epileptogenic events. Therefore, we tested the effect of Fyn kinase inhibition with the saracatinib on epileptogenesis after the induction of SE in the rat kainate model of TLE. To mimic human TLE from translational view point, the rat kainate model is more suitable in terms of progressive nature of the disease since the frequency of spontaneous CS consistently increases over time in rats in contrast to the mouse kainate model (Puttachary et al., 2015b and 2016b). Therefore, we tested the saracatinib in the rat kainate model after terminating the behavioral SE with diazepam. The saracatinib (25 mg/kg, oral) was administered at 2 h post-diazepam and repeated twice daily for first three days followed by a single dose daily for the next four days during the first week of post-SE period. The treatment regimen was chosen based on increase in Fyn and PKCδ levels during the first week of post-SE in the mouse model.

Figure 10A:
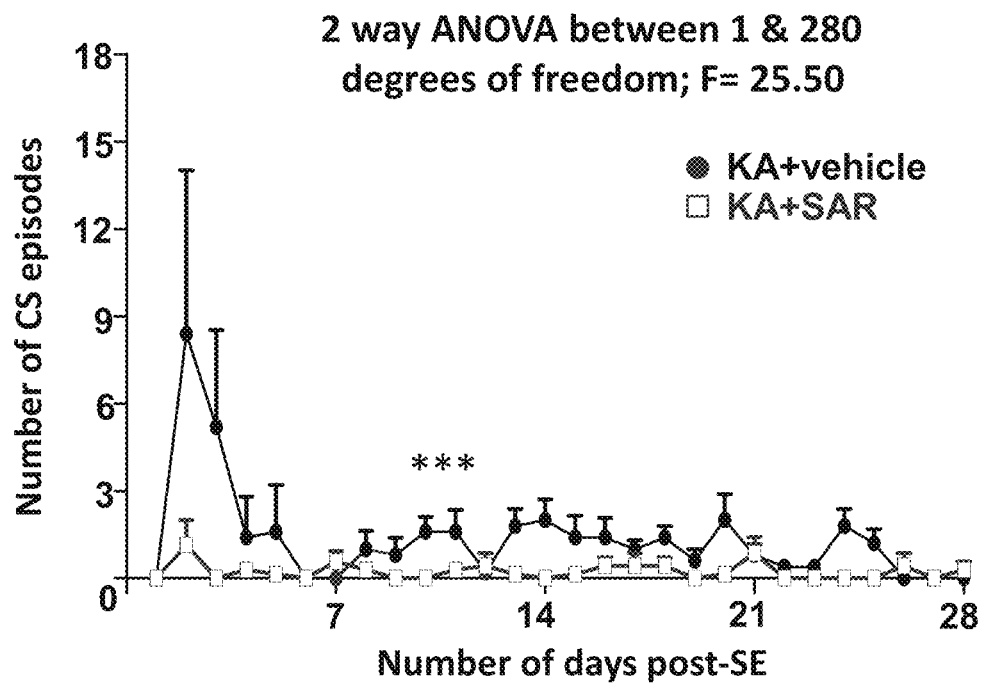
FIGS. 10A and 10B shows the comparison between the numbers of spontaneous CS between the vehicle and SAR treated groups during the four weeks of study. There was a significant reduction in the number of seizure episodes in the SAR treated group when compared to the vehicle control (FIG. 10A, ***$p<0.0001$, two-way ANOVA between 1 and 280 degrees of freedom, $F=25.50$, $n=7$ for each group.
Figure 10B:
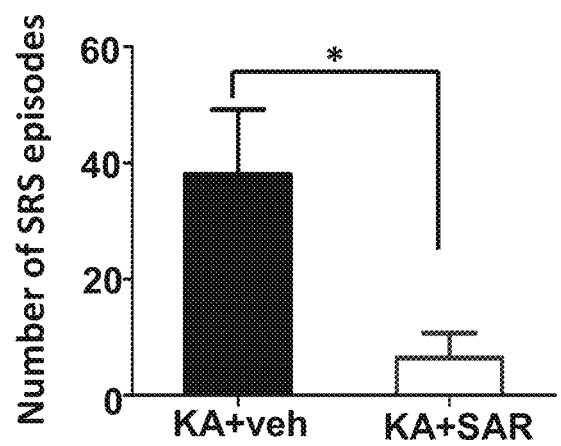
Figure 10C:
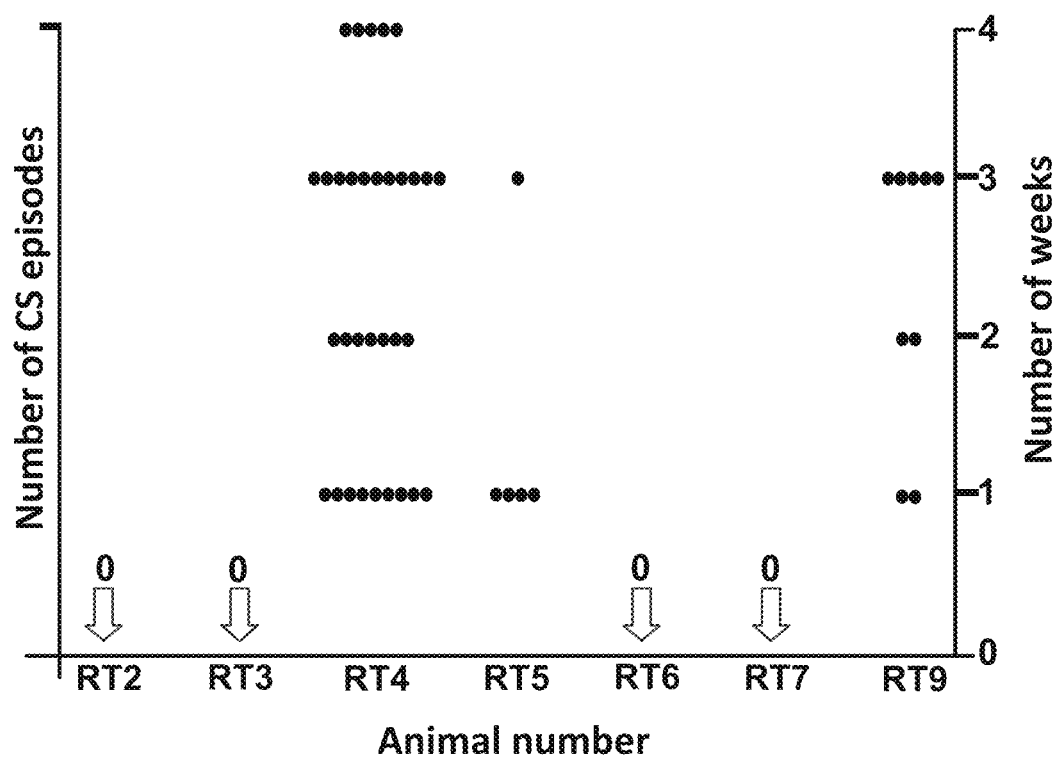
FIG. 10C shows that out of seven SAR treated rats, four did not develop epilepsy. Each dot represents the number of spontaneous CS episodes for the three rats that developed epilepsy.
Figure 10D:
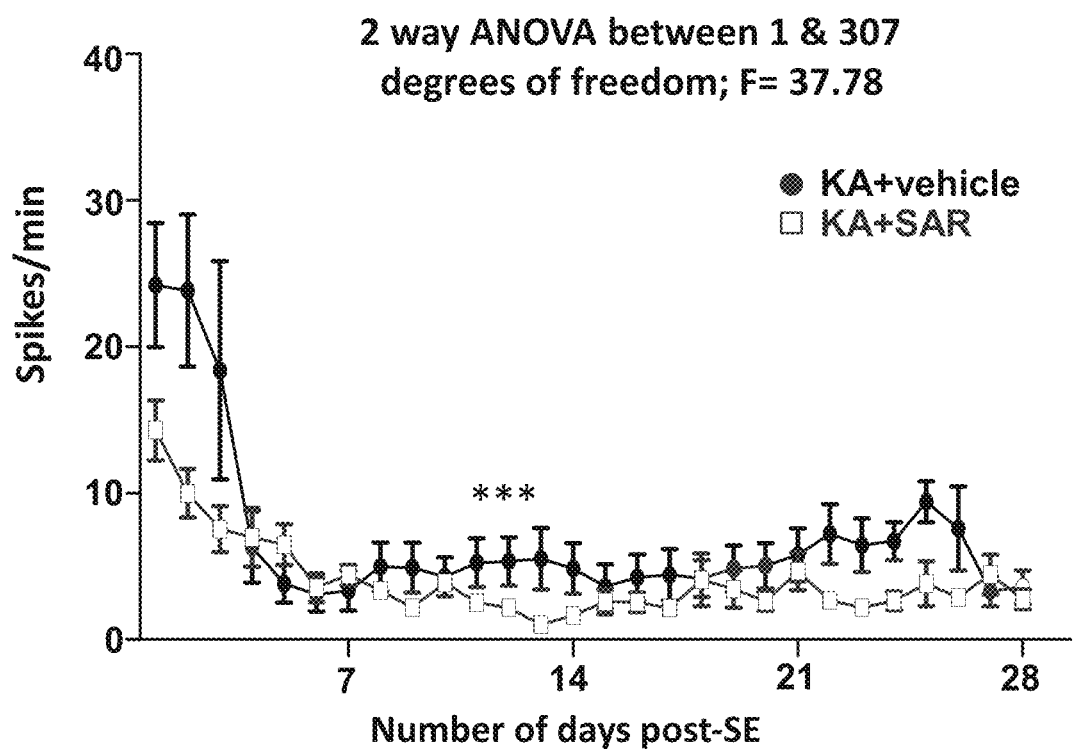
FIGS. 10D and 10E show the comparison of epileptiform frequencies between the SAR and vehicle control rats during 28d post-SE. SAR treatment significantly reduced epileptiform spiking frequency compared to vehicle control (FIG. 10D, *$p<0.0001$, two-way ANOVA between 1 and 307 degrees of freedom, $F=37.78$.
Figure 10E:
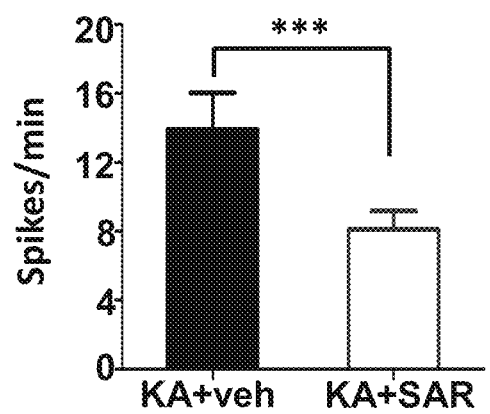
Figure 10F:
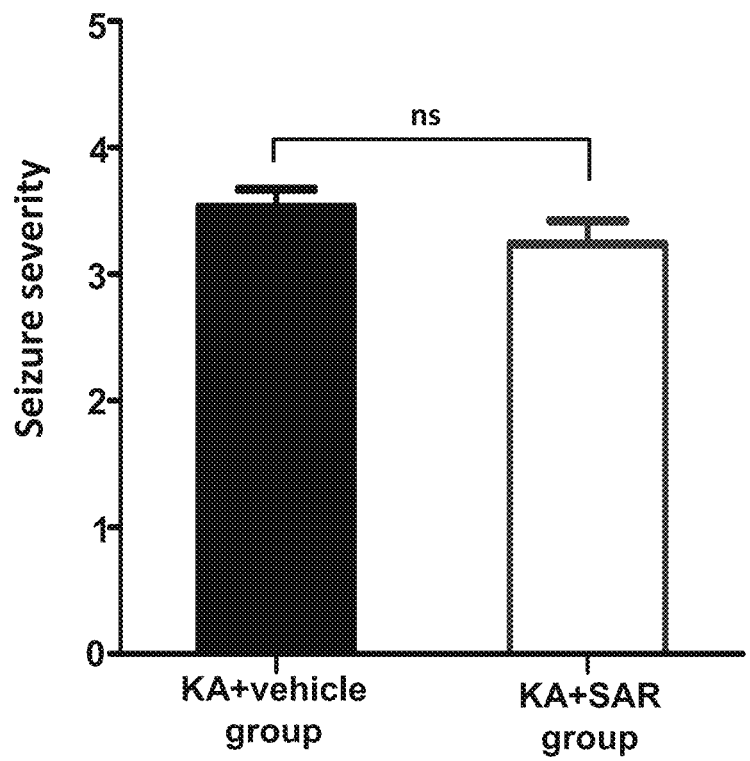
FIG. 10F shows there was no significant difference in the initial SE severity between the SAR and vehicle treated groups.
Figure 11:
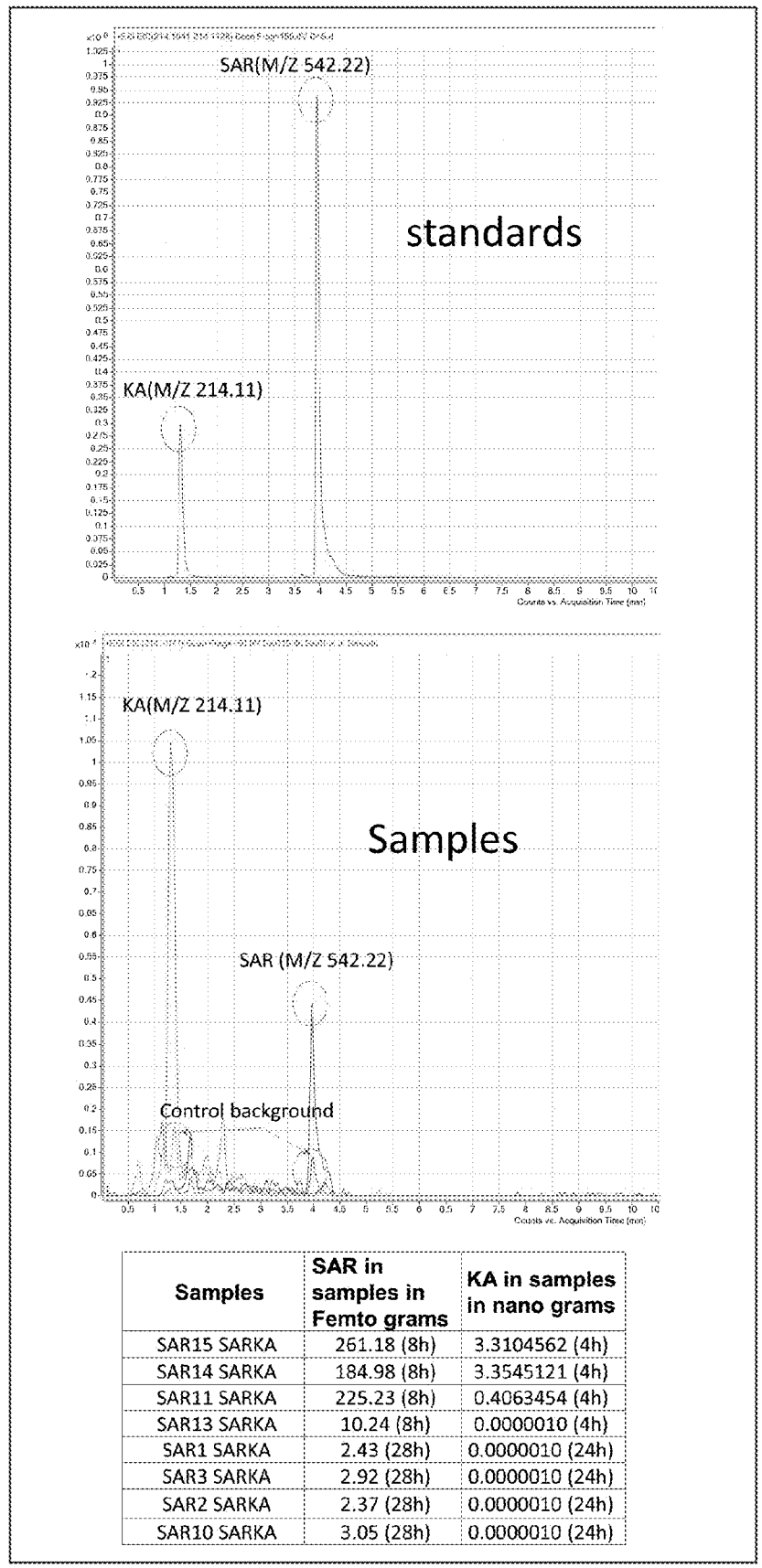
FIG. 11 is a graphical representation of the LC-MS method to determine the drug concentration in brain samples from SAR and KA treated mice.
Figure 12:
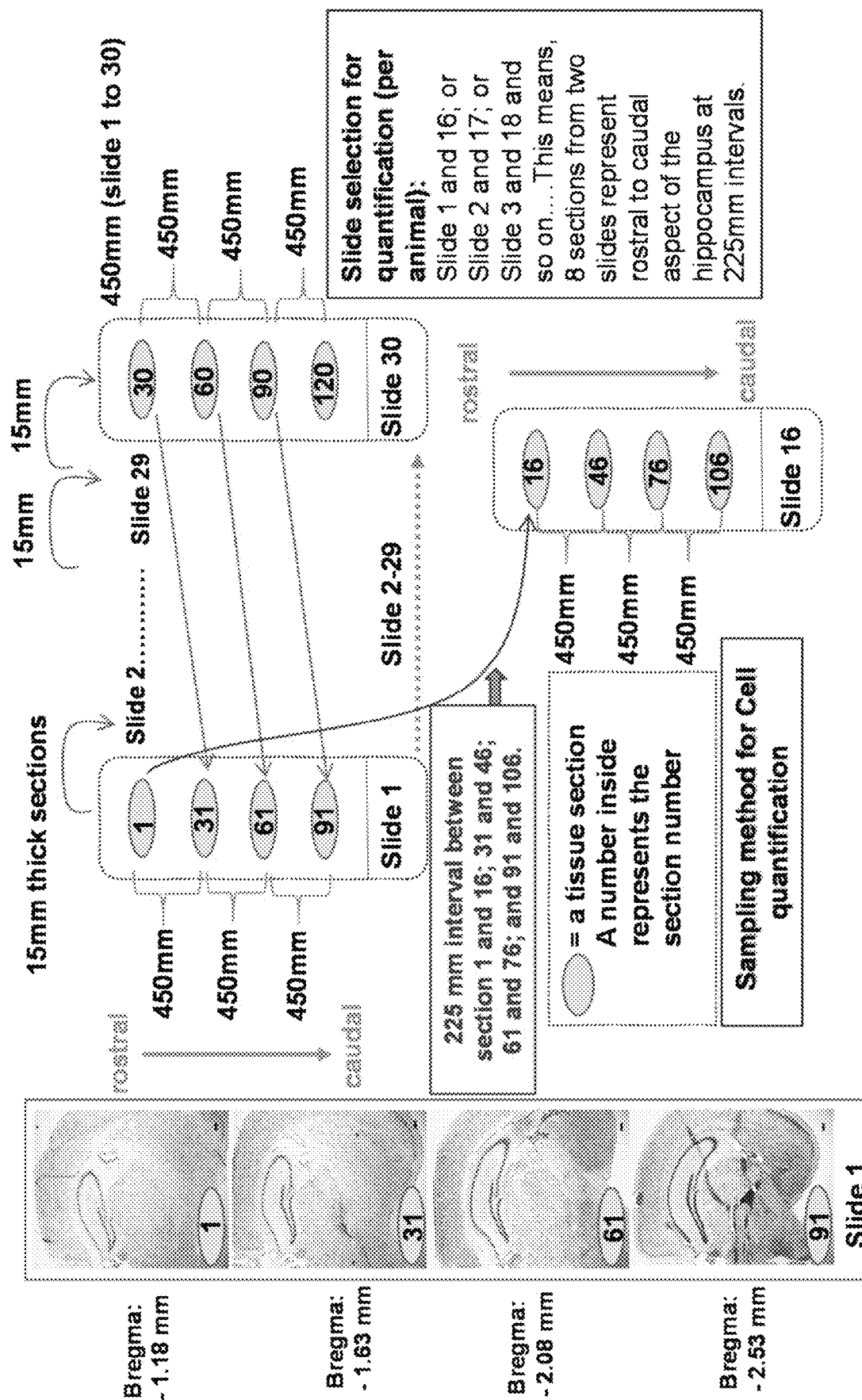
FIG. 12 is a pictorial representation of the method to sample the coronal brain sections, at 225 m intervals, to represent the hippocampus from rostral to caudal for cell quantification

Interestingly, four out of seven rats treated with the saracatinib did not develop epilepsy, and in two rats the number of spontaneous CS were <10 in a month in contrast to >24 seizure episodes in the vehicle treated group. However, one rat did not respond to saracatinib treatment (FIG. 10C). All the 7 rats treated with the vehicle became epileptic and had >24 spontaneous CS in a month long continuous video-EEG study. The number of spontaneous CS and epileptiform spike counts were also significantly reduced in the saracatinib treated rats when compared with the vehicle treated group (FIGS. 10A, 10B, 10D, and 10E). It is also important to note that there was no significant difference in the initial SE severity between the saracatinib and the vehicle treated groups (FIG. 10F).

Example 13

Figure 13A:
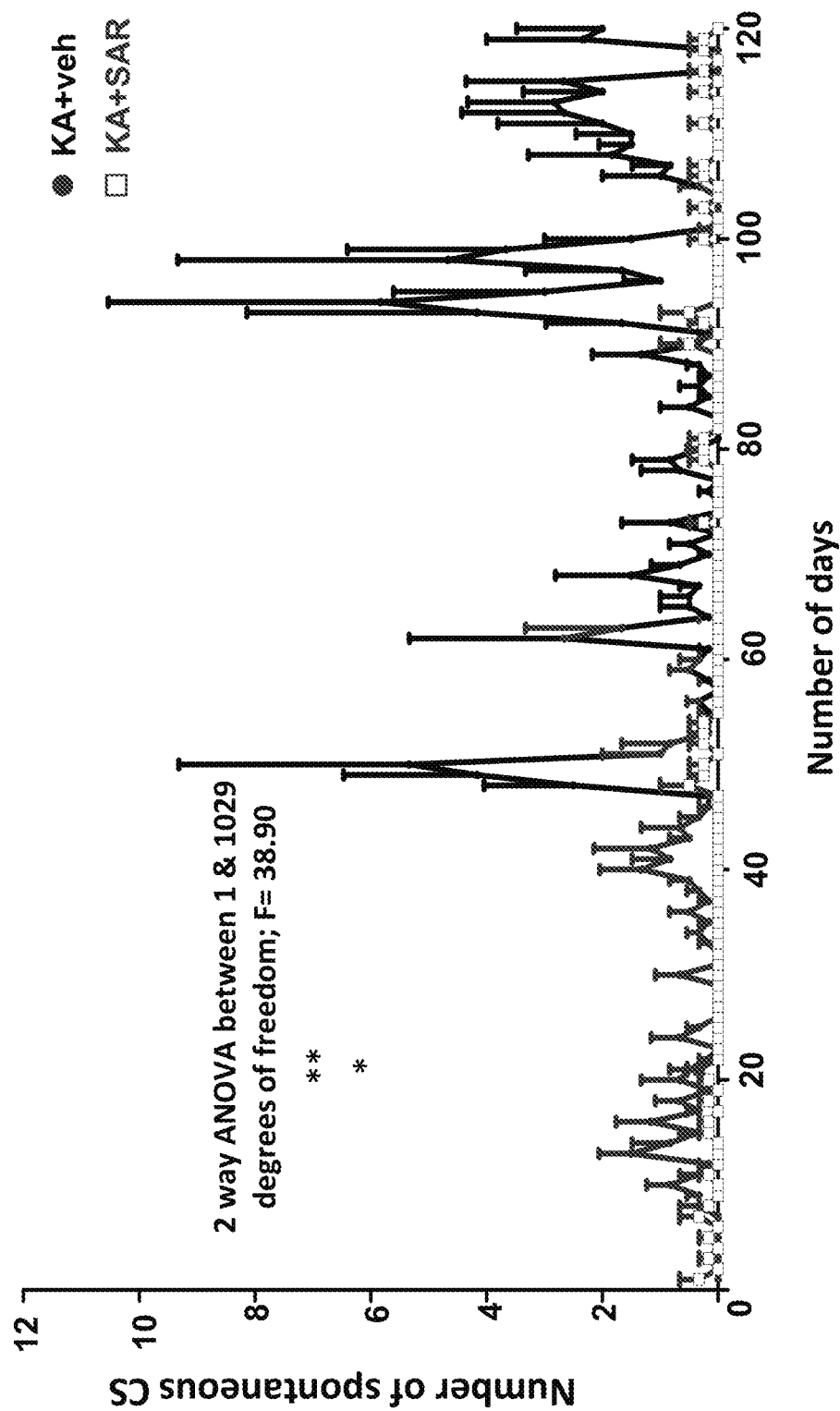
FIG. 13A represents seizures in days.
Figure 13B:
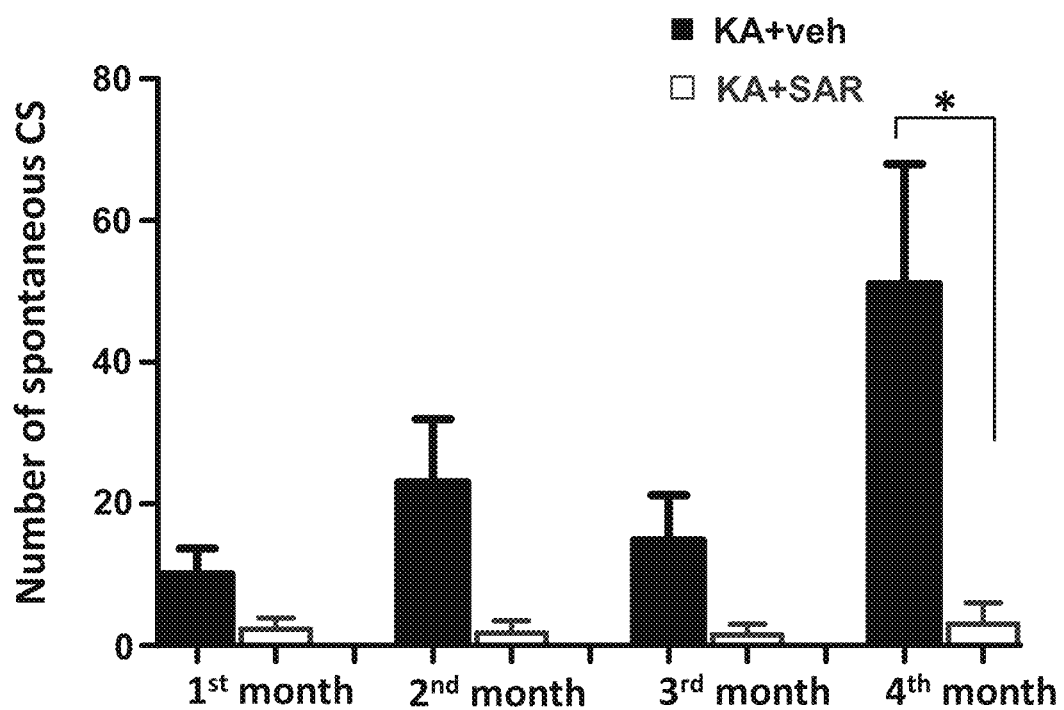
FIG. 13B represents pooled data per month.

Saracatinib Post-Treatment Significantly Reduced Spontaneous Convulsive Seizures in the Rat Kainate Model of Epilepsy: 4 Months Study
Materials and Methods Fifteen rats (n=8 for control and 7 for SAR) were studied over the course of four months. Treatments and methods used in Example 12 were followed for this Example except for the extended time and the SAR/vehicle was administered 2 h after stopping the seizures (SE) with diazepam. The SAR was given at 25 mg/kg, oral twice daily for three days followed by daily for next four days. The drug was NOT administered after 7-day time point.
Results The saracatinib completely prevented the development of epilepsy in four out of seven rats, it significantly reduced seizures in the other animals (one animal did not respond). In the vehicle treated rats, the spontaneous seizures progressively increased over time as expected. FIG. 13A shows the seizures in days, and FIG. 13B shows pooled seizures data per month. Overall, the results suggest that saracatinib is antiepileptogenic in some rats and in other, it can significantly suppress seizures in long term.

What is claimed is:

1. A method of treating a subject in need thereof for temporal lobe epilepsy comprising:
    administering to said subject an effective amount of saracatinib (AZD0503), or a pharmaceutically acceptable salt, or solvate thereof, that inhibits Fyn tyrosine kinase activity and wherein said subject is suffering from chronic and recurrent seizures.

2. The method of claim 1, wherein the saracatinib is administered intravenously, intramuscularly, subcutaneously, intraorbitally, intracapsularly, intraperitoneally, intrarectally, or intracisternally to said subject.

3. The method of claim 1, wherein said administration is orally.

4. The method of claim 1 wherein said subject is a human.

5. The method of claim 1 wherein said saracatinib is selected from the group consisting of saracatinib free base, saracatinib difumarate, and/or a combination thereof.

6. The method of claim 1 wherein said saracatinib is saracatinib free base.

7. The method of claim 1 wherein said saracatinib is saracatinib difumarate.

8. The method of claim 1 wherein said saracatinib is N-(5-chloro-1,3-benzodioxol-4-yl)-7-[2-(4-methylpiperazin-1-yl)ethoxy]-5-(oxan-4-yloxy)quinazolin-4-amine or a salt thereof.

9. The method of claim 1 wherein said saracatinib administration further comprises a pharmaceutically acceptable carrier.

10. The method of claim 1 further comprising the step of administering a second epilepsy treating compound.

11. The method of claim 10 wherein said second epilepsy treating compound is a second Src tyrosine kinase inhibitor.

12. The method of claim 10 wherein said second epilepsy treating compound is one or more of the following: phenytoin, carbamazepine, clonazepam, ethosuximide, valproic acid, barbiturates, felbamate, gabapentin, lamotrigine, oxcarbazepine, tiagabine, topiramate, vigabartrin, zonisamide and levetiracetam.

* * * * *